US009398955B2

(12) United States Patent
Boyden et al.

(10) Patent No.: US 9,398,955 B2
(45) Date of Patent: *Jul. 26, 2016

(54) ARTIFICIAL JOINT COMPONENTS INCLUDING MECHANIZED SYNOVIAL FLUID DEFLECTING STRUCTURES AND PARTICLE RETAINING STRUCTURES

(71) Applicant: Elwha LLC, Bellevue, WA (US)

(72) Inventors: Edward S. Boyden, Chestnut Hill, MA (US); Gregory J. Della Rocca, Columbia, MO (US); Daniel Hawkins, Pleasanton, CA (US); Roderick A. Hyde, Redmond, WA (US); Robert Langer, Newton, MA (US); Eric C. Leuthardt, St. Louis, MO (US); Terence Myckatyn, St. Louis, MO (US); Parag Jitendra Parikh, St. Louis, MO (US); Dennis J. Rivet, Chesapeake, VA (US); Joshua S. Shimony, St. Louis, MO (US); Michael A. Smith, Phoenix, AZ (US); Clarence T. Tegreene, Mercer Island, WA (US)

(73) Assignee: Elwha LLC, Bellevue, WA (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/285,968

(22) Filed: May 23, 2014

(65) Prior Publication Data
US 2014/0257498 A1   Sep. 11, 2014

Related U.S. Application Data

(63) Continuation of application No. 13/659,020, filed on Oct. 24, 2012, now Pat. No. 8,845,740, which is a continuation-in-part of application No. 13/628,442, filed on Sep. 27, 2012, now Pat. No. 8,828,081, which is a continuation-in-part of application No. 13/629,918, filed on Sep. 28, 2012, now Pat. No. 8,795,378.

(51) Int. Cl.
*A61F 2/30* (2006.01)
*A61F 2/32* (2006.01)
(Continued)

(52) U.S. Cl.
CPC ... *A61F 2/30* (2013.01); *A61F 2/32* (2013.01); *A61F 2/38* (2013.01); *A61F 2/40* (2013.01);
(Continued)

(58) Field of Classification Search
CPC ................................. A61F 2/28; A61F 2/38
See application file for complete search history.

(56) References Cited

U.S. PATENT DOCUMENTS

| 4,731,088 | A | 3/1988 | Collier |
|---|---|---|---|
| 5,378,228 | A | 1/1995 | Schmalzried et al. |

(Continued)

FOREIGN PATENT DOCUMENTS

| WO | WO 2008/044229 A1 | 4/2008 |
|---|---|---|
| WO | WO 2008/057565 A2 | 5/2008 |

OTHER PUBLICATIONS

U.S. Appl. No. 14/284,713, Boyden et al.
(Continued)

*Primary Examiner* — Jason-Dennis Stewart
(74) *Attorney, Agent, or Firm* — Advent, LLP; Daniel J. Honz

(57) ABSTRACT

Prosthetic artificial joints are described, including hip, knee and shoulder joints. In some embodiments, an artificial joint prosthesis includes: a bone-facing surface of a artificial joint prosthesis, the bone-facing surface configured to face a bone-prosthesis interface in vivo; a non-contact surface of the artificial joint prosthesis, the non-contact surface adjacent to the bone-facing surface of the artificial joint prosthesis; at least one fluid deflection structure positioned adjacent to the non-contact surface, the fluid deflection structure positioned to deflect synovial fluid away from the bone-prosthesis interface in vivo; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

33 Claims, 11 Drawing Sheets

(51) Int. Cl.
*A61F 2/38* (2006.01)
*A61F 2/40* (2006.01)
*A61F 2/48* (2006.01)
*A61F 2/34* (2006.01)
*A61F 2/36* (2006.01)

(52) U.S. Cl.
CPC ... *A61F 2/30742* (2013.01); *A61F 2002/30079* (2013.01); *A61F 2002/3082* (2013.01); *A61F 2002/30087* (2013.01); *A61F 2002/3092* (2013.01); *A61F 2002/30558* (2013.01); *A61F 2002/30673* (2013.01); *A61F 2002/30682* (2013.01); *A61F 2002/30683* (2013.01); *A61F 2002/3429* (2013.01); *A61F 2002/3631* (2013.01); *A61F 2002/482* (2013.01)

(56) References Cited

U.S. PATENT DOCUMENTS

| | | |
|---|---|---|
| 5,514,182 A | 5/1996 | Shea |
| 5,558,091 A | 9/1996 | Acker et al. |
| 5,571,195 A | 11/1996 | Johnson |
| 5,665,118 A | 9/1997 | LaSalle et al. |
| 5,769,093 A | 6/1998 | Bays |
| 5,879,404 A | 3/1999 | Bateman et al. |
| 5,879,406 A | 3/1999 | Lilley |
| 5,916,269 A | 6/1999 | Serbousek et al. |
| 6,132,470 A | 10/2000 | Berman |
| 6,368,354 B2 | 4/2002 | Burstein et al. |
| 6,432,141 B1 | 8/2002 | Stocks et al. |
| 6,569,202 B2 | 5/2003 | Whiteside |
| 6,599,321 B2 | 7/2003 | Hyde, Jr. |
| 6,761,741 B2 | 7/2004 | Iesaka |
| 7,144,427 B2 | 12/2006 | Southworth |
| 7,476,250 B1 | 1/2009 | Mansmann |
| 7,758,653 B2 | 7/2010 | Steinberg |
| 7,811,328 B2 | 10/2010 | Molz, IV et al. |
| 8,795,378 B2 | 8/2014 | Boyden et al. |
| 8,828,081 B2 | 9/2014 | Boyden et al. |
| 8,845,739 B2 | 9/2014 | Boyden et al. |
| 8,845,740 B2 | 9/2014 | Boyden et al. |
| 8,845,741 B2 | 9/2014 | Boyden et al. |
| 2002/0087213 A1 | 7/2002 | Bertram, III |
| 2003/0014122 A1 | 1/2003 | Whiteside |
| 2003/0130740 A1 | 7/2003 | Stocks et al. |
| 2003/0195633 A1 | 10/2003 | Hyde, Jr. |
| 2003/0229398 A1 | 12/2003 | Iesaka |
| 2003/0233149 A1 | 12/2003 | Hodorek |
| 2004/0068322 A1 | 4/2004 | Ferree |
| 2004/0111162 A1 | 6/2004 | Southworth |
| 2005/0055101 A1 | 3/2005 | Sifneos |
| 2005/0075719 A1 | 4/2005 | Bergheim |
| 2006/0149386 A1 | 7/2006 | Clarke et al. |
| 2008/0306324 A1 | 12/2008 | Bonutti et al. |
| 2009/0005867 A1 | 1/2009 | Lefranc et al. |
| 2010/0145464 A1 | 6/2010 | Sidhom |
| 2010/0222890 A1 | 9/2010 | Barnett et al. |
| 2010/0262160 A1 | 10/2010 | Boyden et al. |
| 2011/0116968 A1 | 5/2011 | Brunner et al. |
| 2012/0150310 A1 | 6/2012 | Taylor et al. |
| 2012/0191202 A1 | 7/2012 | Borowsky |
| 2014/0257496 A1 | 9/2014 | Boyden et al. |
| 2014/0257497 A1 | 9/2014 | Boyden et al. |
| 2014/0277519 A1 | 9/2014 | Boyden et al. |

OTHER PUBLICATIONS

U.S. Appl. No. 14/283,572, Boyden et al.
U.S. Appl. No. 14/282,811, Boyden et al.
Agarwal, Sanjeev; "Osteolysis—basic science, incidence and diagnosis"; Current Orthopaedics; 2004; pp. 220-231; vol. 18; Elsevier Ltd.
Anthony et al.; "Localised Endosteal Bone Lysis in Relation to the Femoral Components of Cemented Total Hip Arthroplasties"; The Journal of Bone and Joint Surgery; Nov. 1990; pp. 971-979; vol. 72-B, No. 6; British Editorial Society of Bone and Joint Surgery.
Bartlett et al.; "In vitro influence of stem surface finish and mantle conformity on pressure generation in cemented hip arthroplasty"; Acta Orthopaedica; 2009; pp. 139-143; vol. 80, No. 2; Informa Healthcare Ltd.
Bartlett et al.; "The femoral stem pump in cemented hip arthroplasty: An in vitro model"; Medical Engineering and Physics; 2008; pp. 1042-1048; vol. 30; Elsevier Ltd.
Bhattacharya et al.; "Propulsion and Trapping of Microparticles by Active Cilia Arrays"; Langmuir; 2012; pp. 3217-3226; vol. 28; American Chemical Society.
Chatterjee et al.; "Synthesis of Polyethylene Magnetic Nanoparticles"; European Cells and Materials; 2002; pp. 98-101; vol. 3, Suppl. 2.
Collier et al.; "Osteolysis After Total Knee Arthroplasty: Influence of Tibial Baseplate Surface Finish and Sterilization of Polyethylene Insert, Findings at Five to Ten Years Postoperatively"; The Journal of Bone and Joint Surgery; Dec. 2005; pp. 2702-2708; vol. 87-A, No. 12.
Fahlgren et al.; "Fluid pressure and flow as a cause of bone resorption"; Acta Orthopaedica; 2010; pp. 508-516; vol. 81, No. 4.
Keawboonchuay et al.; "Maximum Power Generation in a Piezoelectric Pulse Generator"; IEEE Transactions on Plasma Science; Feb. 2003; pp. 123-128; vol. 31, No. 1; IEEE.
Killeya, Matthew; "First practical plastic magnets created"; New Scientist; Aug. 30, 2004; pp. 1-3.
Linden, Joel; "Longer life for artificial joints"; Nature; Jul. 12, 2012; pp. 179-180; vol. 487; Macmillan Publishers Limited.
Manley et al.; "Osteolysis: A Disease of Access to Fixation Interfaces"; Clinical Orthopaedics and Related Research; 2002; pp. 129-137; No. 405; Lippincott Williams & Wilkins, Inc.
Mediero et al.; "Adenosine $A_{2A}$ Receptor Activation Prevents Wear Particle-Induced Osteolysis"; Science Translational Medicine; May 23, 2012; pp. 1-10 plus cover page; vol. 4, 135ra65; American Association for the Advancement of Science.
Millan et al.; "Magnetic polymer nanocomposites"; Chapter 17 in Polymer Nanocomposites, Mai and Yu, eds.; 2006; pp. 440-484 and two cover pages; CRC Press, Woodhead Publishing Limited.
PCT International Search Report; International App. No. PCT/US13/60573; Feb. 5, 2014; pp. 1-4.
PCT International Search Report; International App. No. PCT/US13/60568; Feb. 5, 2014; pp. 1-4.
PCT International Search Report; International Application No. PCT/US13/60577; Dec. 12, 2013; pp. 1-2.
Smith et al.; "Failure rates of stemmed metal-on-metal hip replacements: analysis of data from the National Joint Registry of England and Wales"; The Lancet; Mar. 31, 2012; pp. 1199-1204; vol. 379.
Van Engen, Willem; "Artificial cilia for microfluidics exploring the use of a horizontally micro-structured ferromagnetic PDMS composite"; Master's Thesis, Eindhoven University of Technology; 2008; pp. 1-70; Eindhoven, Netherlands.
Wang et al.; "Novel magnetic polyethylene nanocomposites produced by supported nanometre magnetic Ziegler-Natta catalyst"; Polymer International; 2000; pp. 184-188; vol. 49; Society of Chemical Industry.
Xie, Jing; "A Systematic Review on Performance of the Vanguard® Complete Knee System"; Form No. BOI0500.0, REV083111; Jun. 30, 2011; pp. 1-11 and one additional page; Biomet Inc., Warsaw, Indiana.

ARTIFICIAL JOINT COMPONENTS INCLUDING MECHANIZED SYNOVIAL FLUID DEFLECTING STRUCTURES AND PARTICLE RETAINING STRUCTURES

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

The present application constitutes a continuation of U.S. patent application Ser. No. 13/659,020, entitled ARTIFICIAL JOINT COMPONENTS INCLUDING MECHANIZED SYNOVIAL FLUID DEFLECTING STRUCTURES AND PARTICLE RETAINING STRUCTURES, naming Edward S. Borden; Gregory J. Della Rocca; Daniel Hawkins; Roderick A. Hyde; Robert Longer; Eric C. Leuthardt; Terence Myckatyn; Parag Jitendra Parikh; Dennis J. Rivet; Joshua S. Shimony; Michael A. Smith; and Clarence T. Tegreene as inventors, filed 24 Oct. 2012, which is currently co-pending or is an application of which a currently co-pending application is entitled to the benefit of the filing date, and which is a continuation-in-part of U.S. patent application Ser. No. 13/628,442, entitled ARTIFICIAL JOINT COMPONENTS INCLUDING SYNOVIAL FLUID DEFLECTING STRUCTURES, naming Edward S. Boyden; Gregory J. Della Rocca; Daniel Hawkins; Roderick A. Hyde; Robert Langer; Eric C. Leuthardt; Terence Myckatyn; Parag Jitendra Parikh; Dennis J. Rivet; Joshua S. Shimony; Michael A. Smith; and Clarence T. Tegreene as inventors, filed 27 Sep. 2012, which is a continuation-in-part of U.S. patent application Ser. No. 13/629,918, entitled ARTIFICIAL JOINT COMPONENTS INCLUDING SYNOVIAL FLUID DEFLECTING STRUCTURES AND PARTICLE RETAINING STRUCTURES, naming Edward S. Boyden; Gregory J. Della Rocca; Daniel Hawkins; Roderick A. Hyde; Robert Langer; Eric C. Leuthardt; Terence Myckatyn; Parag Jitendra Parikh; Dennis J. Rivet; Joshua S. Shimony; Michael A. Smith; and Clarence T. Tegreene as inventors, filed 28 Sep. 2012.

RELATED APPLICATIONS

U.S. patent application Ser. No. 13/658,982, entitled ARTIFICIAL JOINT COMPONENTS INCLUDING MECHANIZED SYNOVIAL FLUID DEFLECTING STRUCTURES, naming Edward S. Boyden; Gregory J. Della Rocca; Daniel Hawkins; Roderick A. Hyde; Robert Langer; Eric C. Leuthardt; Terence Myckatyn; Parag Jitendra Parikh; Dennis J, Rivet; Joshua S. Shimony; Michael A. Smith; and Clarence T. Tegreene as inventors, filed 24 Oct. 2012, is related to the present application.

U.S. patent application Ser. No. 13/675,068, entitled ARTIFICIAL JOINT COMPONENTS INCLUDING INTEGRAL MAGNETIC FIELDS CONFIGURED TO DEFLECT WEAR DEBRIS PARTICLES, naming Edward S. Boyden; Gregory J. Della Rocca; Daniel Hawkins; Roderick A. Hyde; Robert Langer; Eric C. Leuthardt; Terence Myckatyn; Parag Jitendra Parikh; Dennis J. Rivet; Joshua S. Shimony; Michael A. Smith; and Clarence T. Tegreene as inventors, filed 13 Nov. 2012, is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In one aspect, an artificial joint prosthesis includes, but is not limited to: a bone-facing surface of a artificial joint prosthesis, the bone-facing surface configured to face a bone-prosthesis interface in vivo; a non-contact surface of the artificial joint prosthesis, the non-contact surface adjacent to the bone-facing surface of the artificial joint prosthesis; at least one fluid deflection structure positioned adjacent to the non-contact surface, the fluid deflection structure positioned to deflect synovial fluid away from the bone-prosthesis interface in vivo; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

In one aspect, an artificial joint prosthesis includes, but is not limited to: a bone-facing surface of a artificial joint prosthesis, the bone-facing surface configured to face a bone-prosthesis interface in vivo; a non-load bearing surface of the artificial joint prosthesis, the non-load bearing surface adjacent to the bone-facing surface of the artificial joint prosthesis; at least one fluid deflection structure positioned adjacent to the non-load bearing surface; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

In one aspect, an artificial hip joint prosthesis includes, but is not limited to: a bone-facing surface of a hip joint prosthesis, the bone-facing surface configured to face a bone-prosthesis interface in vivo; a non-contact surface of the hip joint prosthesis, the non-contact surface adjacent to the bone-facing surface of the hip joint prosthesis; at least one fluid deflection structure positioned adjacent to the non-contact surface, the fluid deflection structure positioned to deflect synovial fluid away from the bone-prosthesis interface in vivo; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

In one aspect, an artificial knee joint prosthesis includes, but is not limited to: a bone-facing surface of a knee joint prosthesis, the bone-facing surface configured to face a bone-prosthesis interface in vivo; a non-contact surface of the knee joint prosthesis, the non-contact surface adjacent to the bone-facing surface of the knee joint prosthesis; at least one fluid deflection structure positioned adjacent to the non-contact surface, the fluid deflection structure positioned to deflect synovial fluid away from the bone-prosthesis interface in vivo; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

In one aspect, an artificial shoulder joint prosthesis includes, but is not limited to: a bone-facing surface of a shoulder joint prosthesis, the bone-facing surface configured to face a bone-prosthesis interface in vivo; a non-contact surface of the shoulder joint prosthesis, the non-contact surface adjacent to the bone-facing surface of the shoulder joint prosthesis; at least one fluid deflection structure positioned adjacent to the non-contact surface, the fluid deflection structure positioned to deflect synovial fluid away from the bone-prosthesis interface in vivo; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

In addition to the foregoing, other aspects of the artificial joint prostheses are described in the claims, drawings, and text forming a part of the disclosure set forth herein. The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
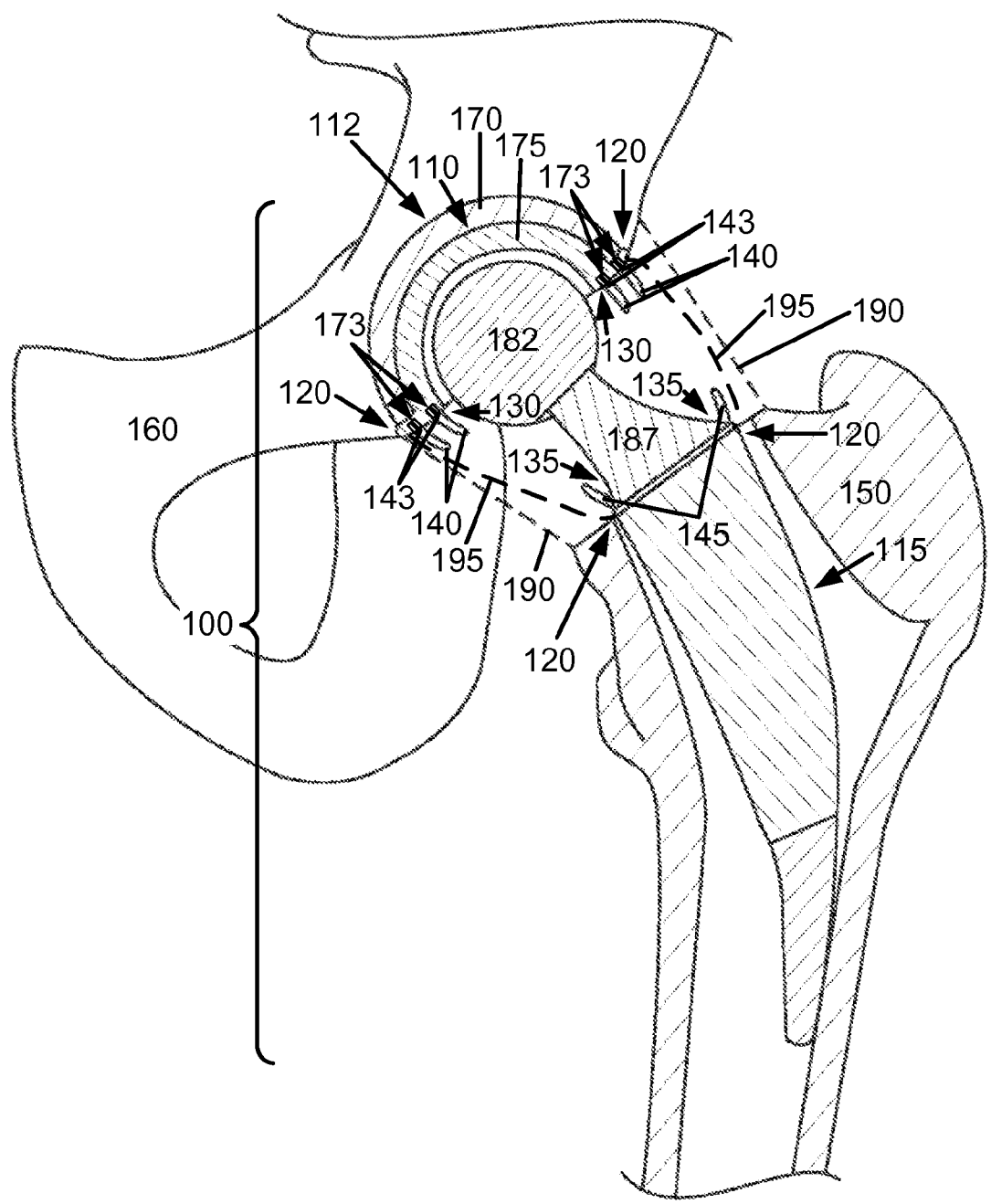
FIG. 1 illustrates a artificial hip joint in cross-section.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Artificial joint prostheses are used as a surgical therapeutic substitute for joint components that are damaged, such as due to injury or osteoarthritis. The goals of surgical implantation of artificial joint prostheses generally include improving joint function and alleviating pain. Although these surgeries have a high success rate, there is some risk over time that an artificial joint prosthesis can fail. Failure of artificial prosthetic joints can require further surgery, with associated costs and morbidity for the patient. One clinically significant type of artificial joint failure is associated with loosening of the prosthesis at the bone interface, including osteolysis and related damage to the bone.

Artificial joint prosthesis failure related to loosening of the prosthesis at the bone interface can have significant adverse clinical consequences. Patients can experience pain and reduced mobility, for example, which can pose a problem for patients who are otherwise active. In addition, artificial joint prosthesis failure related to loosening of the prosthesis can pose a particular problem in younger patients who have many years of expected lifespan ahead of them, with the associated need to preserve bone mass and joint function for the future. The negative consequences of prosthesis failure related to loosening of the prosthesis can also increase the medical burden of patients with secondary medical problems. For example, reduced mobility from prosthetic joint failure can be a significant problem for a person who uses exercise to control their high blood pressure. In some cases, surgical revision is required to address prosthesis failure related to loosening of the prosthesis, with associated costs and morbidity to the patient. Although surgical revision rates vary by the type of prosthesis used and patient subgroup, a recent study of hip prosthesis failure rates found 5 year revision rates ranging from 1.6% to 6.1% (Smith et al., "Failure rates of Stemmed Metal-on-metal Hip Replacements: Analysis of Data from the National Joint Registry of England and Wales," *The Lancet,* 379:1199-1204 (2012), which is incorporated herein by reference).

Artificial joint prosthesis failure is associated in a significant number of cases with loosening of the prosthesis at the prosthesis-joint interface or in the periprosthetic region due to loss of the adjacent bone. This is believed to be caused in part from osteolysis promoted by the body's response to debris from the artificial joint prosthesis. See, e.g. Linden, "Longer Life for Artificial Joints," Nature 487: 179-180, (2012): and U.S. Pat. No. 5,378,228 "Method and Apparatus for Joint Fluid Decompression and Filtration with Particulate Debris Collection," to Schmalzried and Jasty, which are each incorporated herein by reference. Wear debris from the prosthesis surface coming into contact with the bone-prosthesis interface has been implicated, for example, in loosening of the prosthesis and associated failure. Debris particles at the prosthesis-bone interface can contribute to osteolysis and resulting prosthesis loosening with potential failure of the prosthesis. Debris particles within the synovial fluid can include, for example, one or more of: cellular debris particles, particulates of bone and prosthesis generated during surgery, and particulates formed from wear of the artificial joint prosthesis. Some studies indicate that debris particles can enter the prosthesis-bone interface region through increased synovial fluid pressure at the prosthesis-joint interface during physiological movement. Some studies indicate that debris particles can enter the prosthesis-bone interface region through increased synovial fluid flow rate against the prosthesis joint interface during physiological movement. Studies also indicate that both fluid pressure and flow rate at the prosthesis-joint interface due to prosthesis movement during physiological activities encourage debris particles to enter the prosthesis-bone interface, contributing to osteolysis and prosthesis failure. See: Smith et al., ibid.; Fahlgren et al., "Fluid Pressure and Flow as a Cause of Bone Resorption," *Acta Orthopaedica* 81(4):508-516 (2010): Bartlett et al., "In Vitro Influence of Stem Surface Finish and Mantle Conformity on Pressure Generation in Cemented Hip Arthroplasty," *Acta Orthopaedica* 80(2): 139-143 (2009): Bartlett et al., "The Femoral Stem Pump in Cemented Hip Arthroplasty: an In Vitro Model," *Medical Engineering and Physics,* 30: 1042-1048 (2008): Agarwal, "Osteolysis—Basic Science, Incidence and Diagnosis," *Current Orthopaedics* 18: 220-231 (2004); Manley et al., "Osteolysis: a Disease of Access to Fixation Interfaces," Clinical Orthopaedics and Related Research 405:129-137 (2002); and Anthony et al., "Localized Endosteal Bone Lysis in Relation to the Femoral Components of Cemented Total Hip Arthroplasties," *British Journal of Bone and Joint Surgery,* 72-B(6): 971-979 (1990), which are each incorporated herein by reference. See also: US Patent Application No. 2003/0014122 and U.S. Pat. No. 6,569,202, each titled "Tray and Liner for Joint Replacement System," to Whiteside; US Patent Application No. 2005/0055101 "Endoprosthesis of the Knee and/or other Joints," to Sifneos; and US Patent Application No. 2004/0068322, "Reduced-Friction Artificial Joints and Components Therefor" to Ferree, which are each incorporated herein by reference.

The artificial joint prosthesis components described herein include synovial fluid deflecting structures configured to divert synovial fluid flow away from the prosthesis-bone interface. Each of the artificial joints includes at least one fluid deflecting structure that is attached to a mechanism that moves the fluid deflecting structure to direct synovial fluid away from the bone-prosthesis interface in vivo. In some embodiments, the artificial joints include fluid deflecting structures that are passive, or not attached to a mechanism that moves the fluid deflecting structure, as well as fluid deflecting structures that are active, or attached to a mechanism. Embodiments that include both active and passive fluid deflecting structures are configured for the combination of structures to act synergistically to deflect joint fluid. The artificial joint prosthesis components described herein include synovial fluid deflecting structures configured, in combination with any attached mechanisms, to divert synovial fluid and debris particles within the fluid away from the prosthesis-bone interface. The synovial fluid deflecting structures of the artificial joint prosthesis components described herein are also configured, in combination with any attached mechanisms, to decrease the transient synovial fluid pressure at the prosthesis-bone interface during physiological activities. The artificial joint prostheses described herein also include particle retaining structures configured to sequester particles from the fluid flow, thereby reducing the number of particles present in the joint fluid. The reduction of synovial fluid flow and transient pressure at the bone-prosthesis interface as well as a reduction in the number of debris particles present in the joint fluid will lead to a reduction of debris particles entering the prosthesis-bone interface during physiological movement. This will decrease the risk of osteolysis related to wear debris particles at the prosthesis-bone interface, thereby reducing the risk of prosthesis failure and the need for revision surgery with its associated costs and morbidity. In some embodiments, the prosthesis structures will include additional chemical inhibitors of osteolysis (see, e.g. Linden, ibid, and Mediero et al., "Adenosine $A_{2A}$ Receptor Activation Prevents Wear Particle-Induced Osteolysis," *Science Translational Medicine* 4 (135ra65) (2012), which are each incorporated herein by reference).

Figure 2:
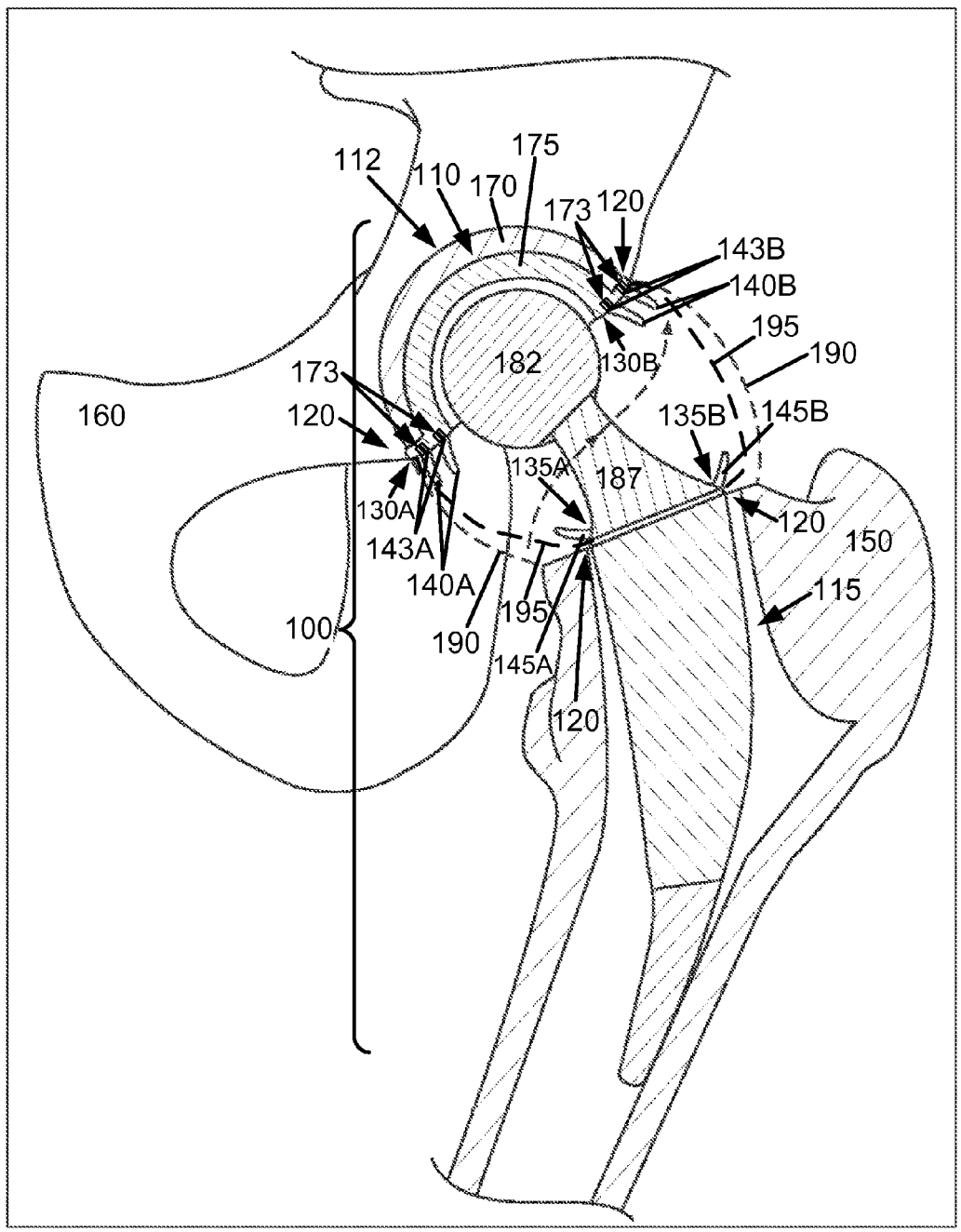
FIG. 2 depicts an artificial hip joint as in FIG. 1, with the joint bent as during physiological use.
Figure 3:
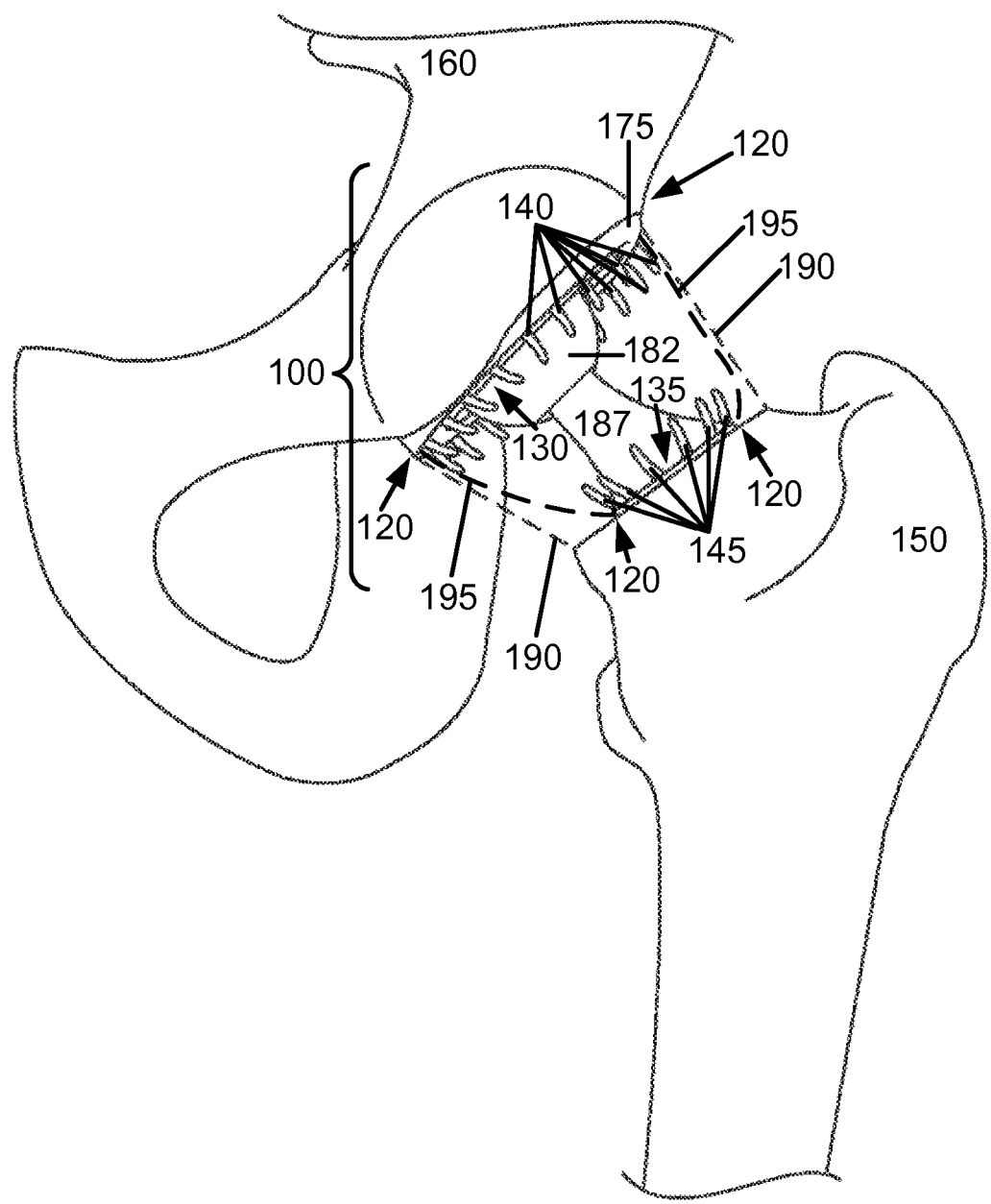
FIG. 3 shows an artificial hip joint as in FIG. 1, in an external view.
Figure 4:
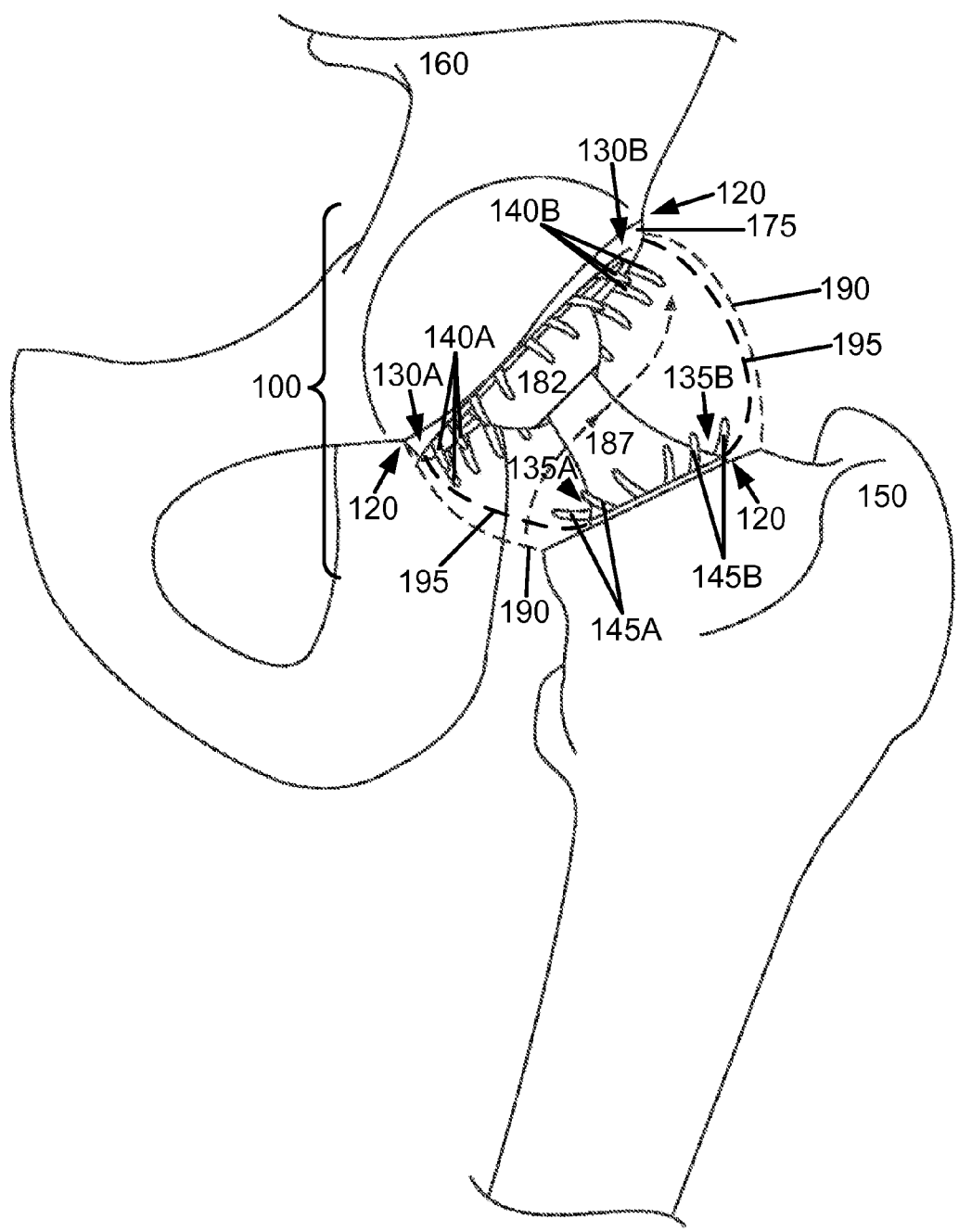
FIG. 4 illustrates an artificial hip joint as in FIG. 2, in an external view.

The artificial joint prosthesis components described herein include synovial fluid deflecting structures configured to deflect synovial fluid flow away from the bone-prosthesis interface as well as to mitigate the transient increase in synovial fluid pressure at the bone-prosthesis interface during physiological movement (see, e.g. FIGS. 2 and 4). Each of the artificial joints includes synovial fluid deflecting structures attached to a mechanism configured to move the synovial fluid deflection structure, and thus to actively direct synovial fluid away from the bone-prosthesis interface in vivo. In some embodiments, an artificial joint includes synovial fluid deflecting structures that are not attached to a mechanism configured to move the structure. Each of the synovial fluid deflecting structures is positioned adjacent to a non-contact surface of the artificial joint prosthesis. In some embodiments, there are synovial fluid deflecting structures positioned on one component of an artificial joint prosthesis. In some embodiments, there are synovial fluid deflecting structures positioned on two or more components of an artificial joint prosthesis, with the synovial fluid deflecting structures configured to deflect fluid in combination during relative motion of the two or more components of an artificial joint prosthesis during in vivo use (see, e.g. FIGS. 1-4). In embodiments with synovial fluid deflecting structures positioned on two or more components of an artificial joint prosthesis, the structures on the components can act synergistically to deflect fluid away from the prosthesis-bone interface. In some embodiments, there are synovial fluid deflecting structures with attached mechanisms configured to induce angular momentum in the synovial fluid during physiological movement. The induced angular momentum of the synovial fluid results in deflection of the synovial fluid flow away from the bone-prosthesis interface, and reduced transient pressure at the bone-prosthesis interface during physiological movement during in vivo use. In some embodiments, there are synovial fluid deflecting structures positioned on one or more of the joint components configured to convert the force from the joint motion on the synovial fluid during physiological movement into a resulting synovial fluid flow in an inclined or orthogonal direction relative to the original synovial fluid flow. The converted inclined or orthogonal direction of the synovial fluid results in deflection of the synovial fluid flow away from the bone-prosthesis interface, and reduced transient pressure at the bone-prosthesis interface during physiological movement during in vivo use. The specific positioning, size, shape and configuration of the synovial fluid deflecting structures on the artificial joint prosthesis components will vary depending on the embodiment, including the specific type of artificial joint prosthesis, its size, the size of the associated joint in vivo, and expected physiological forces on the associated synovial fluid when the artificial joint prosthesis is used in vivo. Similarly, the attached mechanisms will vary depending on the embodiment, including the specific type of artificial joint prosthesis, the size of the prosthesis, the size and configuration of the fluid deflection structures, and the expected force of the synovial fluid flow in vivo.

The artificial joint prosthesis components described herein include particle retaining structures configured to retain non-physiological particles present within the synovial fluid. The fluid deflecting structures are configured, including in size, shape and position, to operate in conjunction with the particle retaining structures in a particular embodiment. For example, a particle retaining structure can be positioned with a surface facing the expected fluid flow mediated by one or more fluid deflecting structures. The configuration of particle retaining structure(s) in conjunction with fluid deflecting structure(s) on the artificial joint will promote fluid flow past the facing surface of the particle retaining structure, increasing transfer of any particles present in the joint fluid from the fluid to the particle retaining structure. Removal of particles by the particle retaining structure will decrease those present in the synovial fluid, reducing the possibility that they will contribute to osteolysis.

The material used to fabricate a synovial fluid deflection structure and any attached mechanism will vary depending on the embodiment. Factors in the selection of materials for a fluid deflection structure and any attached mechanism include: cost of the materials, size of the fluid deflection structure, shape of the fluid deflection structure, flexibility of the fluid deflection structure under the estimated physiological pressure of synovial fluid in a given embodiment, and compatibility of the fluid deflection structure with other components of the prosthetic implant. Materials used to fabricate a fluid deflection structure and any attached mechanism will be part of the prosthetic joint, and therefore should be suitable for implantation into a body (e.g. low toxicity and non-inflammatory). Materials used to fabricate a fluid deflection structure and any attached mechanism should be expected to be durable throughout the anticipated duration of use of the prosthetic joint, for example no less than 10 years of routine physiological use in vivo. Materials suitable for fabrication of a synovial fluid deflection structure include, for example, polypropylene and silicone.

Although the artificial joint prostheses are described herein primarily in reference to humans, in some embodiments the artificial joint prostheses as described herein will also have applicability in veterinary medicine. For example, aspects of the artificial hip joint prosthesis as described herein (see, e.g. FIGS. 1-7 and associated text) have applicability in hip joint replacements in domestic animals, such as dogs and cats.

In some embodiments, an artificial joint prosthesis includes: a bone-facing surface of the artificial joint prosthesis, the bone-facing surface configured to face a bone-prosthesis interface in vivo; a non-load bearing surface of the artificial joint prosthesis, the non-load bearing surface adjacent to the bone-facing surface of the artificial joint prosthesis; at least one fluid deflection structure positioned adjacent to the non-load bearing surface; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid. As used herein, the "non-load bearing surface" of an artificial joint prosthesis is a surface expected to not bear a significant load, such as the person's mass, during routine movement utilizing normal physiological activities. For example, the edge of a acetabular liner in a hip joint prosthesis is generally expected to be non-load bearing during routine movement utilizing normal physiological activity, although the edge of an acetabular liner in a hip joint prosthesis may become load bearing during an extreme physiological event, such as hip joint dislocation. For example, the edge of a humerus component in a shoulder joint prosthesis is generally expected to be non-load bearing during routine movement utilizing normal physiological activity, although the edge of a humerus component in a shoulder joint prosthesis may become load bearing during an extreme physiological event, such as shoulder joint dislocation. The specific regions of an artificial joint prosthesis that would be expected to be a "non-load bearing surface" depend on the specific type of artificial joint, its size and position during in vivo use.

Figure 5:
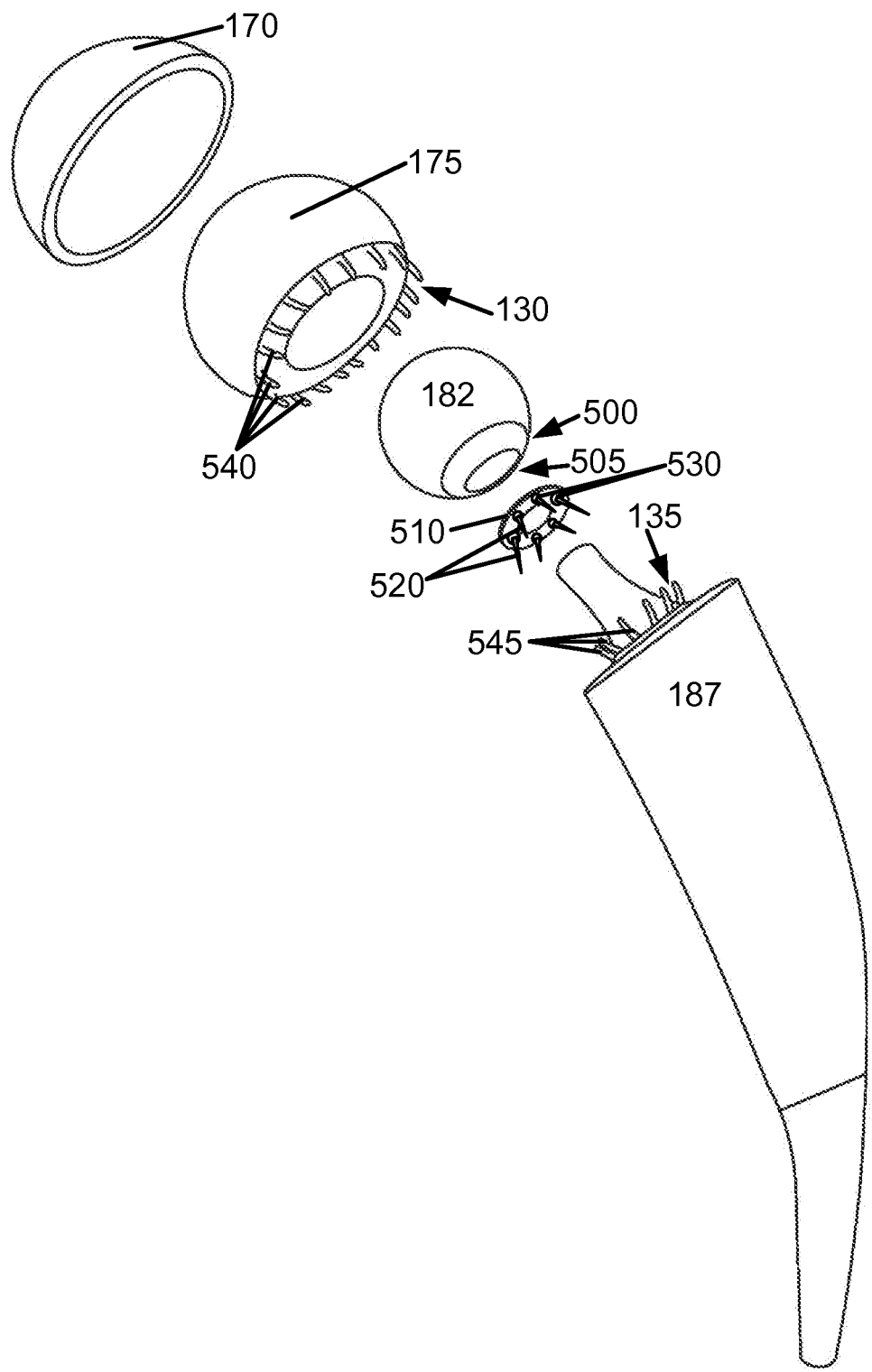
FIG. 5 depicts components of an artificial hip joint.

In some embodiments, an artificial joint prosthesis includes: a bone-facing surface of an artificial joint prosthesis, the bone-facing surface configured to face a bone-prosthesis interface in vivo; a non-contact surface of the artificial joint prosthesis, the non-contact surface adjacent to the bone-facing surface of the artificial joint prosthesis; at least one fluid deflection structure positioned adjacent to the non-contact surface, the fluid deflection structure positioned to deflect synovial fluid away from the bone-prosthesis interface in vivo; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid. As used herein, a "non-contact surface" of an artificial joint prosthesis refers to a surface of a component of the artificial joint prosthesis that is expected to not come into contact with the bone and also to not come into contact with a surface of another component of the artificial joint prosthesis during normal physiological use of the artificial joint prosthesis in vivo. Specific examples of non-contact surfaces are shown in the Figures, and discussed in the relevant text associated with each Figure. The artificial joint prosthesis can include at least one of: a hip joint prosthesis, a knee joint prosthesis, a shoulder joint prosthesis, an ankle joint prosthesis, or an elbow joint prosthesis. See, for example, FIGS. 1-10 and associated text. The non-contact surface of the artificial joint prosthesis is a surface of the prosthesis that is expected to not have contact with bone surfaces of the joint or other surfaces of the joint prosthesis during routine physiological movement in vivo. For example, FIG. 5 depicts components of a hip prosthesis including fluid deflection structures positioned adjacent to the non-contact surfaces. In some embodiments wherein the prosthesis is for a hip joint, the non-contact surface of the artificial joint prosthesis can include at least one of: a region of a shell of a acetabular component of a hip joint prosthesis; a region of a liner of a acetabular component of a hip joint prosthesis; a region of a head of a femoral component of a hip joint prosthesis, or a region of a stem of a femoral component of a hip joint prosthesis. In some embodiments wherein the prosthesis is for a knee joint, the non-contact surface of the artificial joint prosthesis can include at least one of: a region of a femoral component of a knee joint prosthesis; a region of a tibial spacer of a knee joint prosthesis; a region of a tibial component of a knee joint prosthesis; or a region of a component of a patellar component of a knee joint prosthesis. In some embodiments wherein the prosthesis is for a shoulder joint, the non-contact surface of the artificial joint prosthesis can include at least one of: a region of a humeral stem of a shoulder joint prosthesis; a region of a humeral spacer of a shoulder joint prosthesis; a region of a humeral head of a shoulder joint prosthesis; or a region of a glenoid component of a shoulder joint prosthesis.

In some embodiments, an artificial joint prosthesis includes at least one fluid deflection structure positioned adjacent to the non-contact surface with a mechanism attached to the fluid deflection structure, the mechanism operable to move the fluid deflection structure to direct synovial fluid away from the bone-prosthesis interface in vivo, wherein the at least one fluid deflection structure includes at least one flange structure positioned to extend from the non-contact surface. The fluid deflection structure is configured to deflect synovial fluid as described herein. In some embodiments, a fluid deflection structure positioned adjacent to the non-contact surface is configured as at least one flange structure positioned to extend from the non-contact surface. For example, a flange structure can be configured as a projecting rim or collar from the non-contact surface. For example, a flange structure can be configured as one or more ridges positioned adjacent to the non-contact surface. The relative size and shape of the flange structure will vary by the specific type of artificial joint (e.g. hip, knee, shoulder), the flexibility of the material used in construction of the flange structure, and the size of the artificial joint (e.g. relative to the size of the patient and the size of the implant required for therapeutic correction of their joint). In some embodiments, the flange structure can form a ring to encircle the entirety of a non-contact surface. In some embodiments, the flange structure can form a rim or collar along the entirety of a non-contact surface, or along a partial edge of a non-contact surface. In some embodiments, the flange structure can include a series of smaller structures, such as a plurality of projections.

The at least one flange structure can be positioned to extend from the non-contact surface at an angle predicted to mitigate synovial fluid flow rate and transient fluid pressure at the location of the bone-prosthesis interface. The angle of a flange structure projecting from the non-contact surface suitable to deflect synovial fluid flow and reduce transient synovial fluid pressure at the bone-prosthesis interface will depend on the configuration of the artificial joint prosthesis in a specific embodiment, including, for example, the number of flange structures, their relative positioning on the artificial joint prosthesis, the size and shape of the flange structures, the size and position of the attached mechanism, and the size of the joint in vivo. For example, in some embodiments the at least one flange structure can be positioned to extend from the non-contact surface at an angle substantially between 10 degrees and 80 degrees of a plane established by the contact surface and relative to the bone-facing surface of the artificial joint prosthesis. For example, in some embodiments the at least one flange structure can be positioned to extend from the non-contact surface at an angle substantially between 100 degrees and 170 degrees of a plane established by the contact surface and relative to the bone-facing surface of the artificial joint prosthesis. For example, in some embodiments the at least one flange structure can be positioned to extend from the mechanism at the non-contact surface at a substantially right angle from a plane established by the contact surface and relative to the bone-facing surface of the artificial joint prosthesis.

In some embodiments wherein the at least one fluid deflection structure with an attached mechanism positioned adjacent to the non-contact surface includes at least one flange structure positioned to extend from the non-contact surface, the at least one flange structure can include a first end connected to the non-contact surface by the attached mechanism and a second end distal to the non-contact surface, wherein the flange structure is widest at the first end and narrowest at the second end. See, for example, FIGS. 1-4. The at least one flange structure can include at least one flange structure with a first end connected to the non-contact surface by the attached mechanism and a second end distal to the non-contact surface, wherein the flange structure tapers from a widest point at the first end to a narrow point at the second end. See, for example, FIGS. 1-4. In some embodiments, the at least one fluid deflection structure includes at least one flange structure with a curvilinear structure. For example, the flange structure can include a thin, substantially curved structure, such as a crescent moon-shaped structure. See, for example, FIGS. 1-4. In some embodiments, the at least one fluid deflection structure includes at least one flange structure with a significantly straight structure. See, for example, FIG. 5.

In some embodiments, the at least one fluid deflection structure, with an attached mechanism, positioned adjacent to the non-contact surface includes at least one fluid deflection structure with a first end positioned adjacent to the non-contact surface and a second end distal to the non-contact surface. In some embodiments, the at least one fluid deflection structure positioned on the non-contact surface includes a plurality of linear projections. For example, the linear projections can be hair-like or ciliated. See, for example, FIG. 5. The linear projections are positioned adjacent to the non-contact surface at an angle appropriate to divert part of the flow of synovial fluid away from the bone-prosthesis interface, and to reduce synovial fluid pressure at the bone-prosthesis interface during physiological movement. The size, shape, and attachment angle of the linear projections will, therefore, vary by the specific embodiment. For example, in embodiments wherein the at least one fluid deflection structure includes a plurality of linear projections, the linear projections can be positioned to extend from the non-contact surface at an angle substantially between 10 degrees and 80 degrees of a plane established by the contact surface and relative to the bone-facing surface of the artificial joint prosthesis. For example, in embodiments wherein the at least one fluid deflection structure includes a plurality of linear projections, the plurality of linear projections can be positioned to extend from the non-contact surface at an angle substantially between 100 degrees and 170 degrees of a plane established by the contact surface and relative to the bone-facing surface of the artificial joint prosthesis. For example, in embodiments wherein the at least one fluid deflection structure includes a plurality of linear projections, the plurality of linear projections can be positioned to extend from the non-contact surface at an substantially right angle from a plane established by the contact surface and relative to the bone-facing surface of the artificial joint prosthesis.

The at least one fluid deflection structure positioned adjacent to the non-contact surface is positioned relative to the non-contact surface at an angle appropriate to divert part of the flow of synovial fluid away from the bone-prosthesis interface, and to reduce synovial fluid pressure at the bone-prosthesis interface during physiological movement. The size, shape, and attachment angle of the at least one fluid deflection structure will, therefore, vary by the specific embodiment. Some embodiments include at least one fluid deflection structure attached to a single component of the artificial joint prosthesis. Some embodiments include at least two components of the artificial joint prosthesis, each of which include at least one fluid deflection structure positioned adjacent to a non-contact surface of the artificial joint prosthesis. For example, in some embodiments the at least one fluid deflection structure includes a substantially straight fluid deflection structure. For example, in some embodiments the at least one fluid deflection structure includes a substantially curved fluid deflection structure.

Similarly, the rigidity of a synovial fluid deflection structure will vary depending on the embodiment, relative to factors such as the specific type of joint, its size, the expected flow dynamics of synovial fluid through the joint during in vivo use, the position of the synovial fluid deflection structure on the prosthesis, the type and potential force utilized by the attached mechanism, and the shape of the synovial fluid deflection structure. In some embodiments, the at least one fluid deflection structure positioned adjacent to the non-contact surface is configured to be substantially rigid at physiological conditions when the artificial joint is utilized in vivo. In some embodiments, the at least one fluid deflection structure positioned adjacent to the non-contact surface is configured to be flexible at physiological conditions when the artificial joint is utilized in vivo. In some embodiments, the at least one fluid deflection structure positioned adjacent to the non-contact surface is configured to flex to a degree sufficient to permit a larger synovial fluid flow rate away from the bone-prosthesis interface during periods of increased synovial fluid pressure in the region of the non-contact surface when the artificial joint is utilized in vivo at physiological conditions, and to permit a smaller synovial fluid flow rate away from the bone-prosthesis interface during periods of reduced synovial fluid pressure when the artificial joint is utilized in vivo at physiological conditions. In some embodiments, the at least one fluid deflection structure positioned adjacent to the non-contact surface is configured to flex to a degree sufficient to permit an increased synovial fluid flow rate away from the bone-prosthesis interface in response to increased fluid pressure in a region adjacent to the bone-prosthesis interface.

The mechanism attached to at least some of the fluid deflection structures and operable to move the fluid deflection structure to direct synovial fluid away from the bone-prosthesis interface in vivo can be configured in different forms, depending on the embodiment. For example, a mechanism can be attached to a fluid deflection structure and positioned on the surface of the prosthesis. For example, a mechanism and attached fluid deflection structure can be positioned adjacent to the non-contact surface of the prosthesis, such as with epoxy, glue, or other adhesives. For example, a mechanism with an attached fluid deflection structure can be configured to mate with a corresponding surface on the non-contact region of the prosthesis. In some embodiments, a mechanism attached to a fluid deflection structure is substantially enclosed within the artificial joint prosthesis. For example, a mechanism attached to a fluid deflection structure can be substantially enclosed within a cavity or groove in the non-contact region of the prosthesis. For example, a mechanism attached to a fluid deflection structure can be substantially enclosed within an extension of the prosthesis configured to attach the mechanism. A mechanism can be a micromachine, for example one in the size range of 100 nanometers (nm) to 100 micrometers ($\mu$m) in diameter. A mechanism can be a MEMS device, for example with a size range of 20 $\mu$m to 1 millimeter (mm) in diameter.

A mechanism attached to the fluid deflection structure and operable to move the fluid deflection structure to direct synovial fluid away from the bone-prosthesis interface in vivo can be of a variety of types, depending on the embodiment. Factors to be used in the selection of a mechanism include: the force on the fluid deflection structure desired to deflect the fluid; the size, shape and flexibility of the fluid deflection structures; the size of the mechanism; the cost of the mechanism; and the expected duration of use of the artificial joint prosthesis in vivo. In some embodiments, a mechanism attached to a fluid deflection structure includes an actuator attached to the fluid deflection structure and configured to move the fluid deflection structure. For example, an actuator can include a hydraulic piston, which can be positioned within a cavity formed in the prosthesis. In embodiments wherein a mechanism attached to a fluid deflection structure includes an actuator with a hydraulic piston, force from fluid flow against the fluid deflection structure can be transmitted to the piston, with a resulting reverse force transmitted back to the fluid deflection structure to drive later movement of the fluid deflection structure. Some embodiments include a battery configured to provide energy to the actuator. For example, the actuator can include an electric motor which is connected to an attached battery.

In some embodiments, a mechanism attached to a fluid deflection structure includes piezoelectric material, the piezoelectric material configured to drive movement of the fluid deflection structure. For example, in some embodiments a piezoelectric material attached to a fluid deflection structure can be configured to generate electrical charge from the pressure force on the fluid deflection structure, and then store the electrical charge in an attached battery. The stored charge in the battery can then be utilized to drive the same fluid deflection structure, or a second fluid deflection structure, with an attached electric motor at a later time. Instead or in addition, the stored charge in the battery can be utilized to drive the same fluid deflection structure through re-introduction of the electrical charge to the piezoelectric material at a later time, with the resulting reverse piezoelectric effect resulting in pressure force on the fluid deflection structure due to the expansion of the piezoelectric material.

In some embodiments, a mechanism attached to the fluid deflection structure and operable to move the fluid deflection structure to direct synovial fluid away from the bone-prosthesis interface in vivo includes at least one magnetic actuator, the magnetic actuator configured to drive movement of the at least one fluid deflection structure.

Some embodiments include: an aperture in the non-contact surface of the artificial joint prosthesis; a substantially round cavity in the artificial joint prosthesis adjacent to the aperture; a mechanism including a substantially round element of a size and shape to correspond to the substantially round cavity, the substantially round element positioned within the substantially round cavity and configured to move within the substantially round cavity; and the at least one fluid deflection structure attached to the substantially round element and projecting through the aperture. For example, the mechanism can be configured with a substantially round external shape, of a size and shape to reversibly mate with the internal surface of the substantially round cavity in the artificial joint prosthesis. A mechanism with a substantially round external shape within a substantially round cavity can rotate in the cavity, with the resulting movement of a fluid deflection structure attached to the mechanism and projecting through an aperture between the cavity and the external surface of the prosthesis. The mechanism can utilize the force transmitted by the joint fluid through the fluid deflection structure, such as through the operation of a piezoelectric material or hydraulic piston, to drive further movement of the attached fluid deflection structure. The mechanism can be configured as a ball-like structure to rotate within the cavity in multiple directions. The mechanism can be configured as a cylindrical structure, with a corresponding cylindrical cavity, to rotate specifically along the axis formed by the radius of the cylindrical structure.

Some embodiments of an artificial joint prosthesis include: at least one first magnet attached to the artificial joint prosthesis; and at least one second magnet attached to the fluid deflection structure, wherein the mechanism attached to the fluid deflection structure is configured to move in accord with a magnetic field established by the at least one first magnet. Some embodiments of an artificial joint prosthesis include: at least one first magnet attached to the artificial joint prosthesis; and at least one second magnet attached to the fluid deflection structure, wherein the mechanism attached to the fluid deflection structure is configured to allow the at least one second magnet to move the fluid deflection structure in accord with a magnetic field established by the at least one first magnet. The magnets can be configured as a mechanism attached to the fluid deflection structure, the mechanism operable to move the fluid deflection structure to direct synovial fluid away from the bone-prosthesis interface in vivo. The magnets can be configured to assist a mechanism attached to the fluid deflection structure, the mechanism operable to move the fluid deflection structure.

Some embodiments of an artificial joint prosthesis include at least two components, each of which include at least one fluid deflection structure, and each of which include a mechanism attached to a fluid deflection structure, the mechanisms operable to move each of the attached fluid deflection structures to direct synovial fluid away from the bone-prosthesis interface and towards a particle retaining structure in vivo. For example, an artificial hip prosthesis can include a femoral component and an acetabular component, each of which include at least one fluid deflection structure with an attached mechanism, each of the mechanisms operable to move each of the fluid deflection structures to direct synovial fluid away from the bone-prosthesis interface and towards a particle retaining structure in vivo during physiological use of the artificial hip joint.

At least one fluid deflection structure positioned on a non-contact surface of an artificial joint is positioned relative to the non-contact surface at an angle appropriate to divert part of the flow of synovial fluid away from the bone-prosthesis interface and toward a particle retaining structure, as well as to reduce synovial fluid pressure at the bone-prosthesis interface during physiological movement. Every embodiment includes at least one fluid deflection structure attached to a mechanism, the mechanism operable to move the fluid deflection structure to direct synovial fluid away from the bone-prosthesis interface in vivo. Some embodiments include fluid deflection structures that are "active," or attached to a mechanism, as well as fluid deflection structures that are "passive," or not attached to a mechanism, the two types of fluid deflection structures operating synergistically on the artificial joint to divert fluid flow towards one or more particle retaining structures. The size, shape, and attachment angle of a fluid deflection structure will, therefore, vary by the specific embodiment. Some embodiments include at least one fluid deflection structure attached to a single component of the artificial joint prosthesis. Some embodiments include at least two components of the artificial joint prosthesis, each of which include at least one fluid deflection structure positioned on a non-contact surface of the artificial joint prosthesis. For example, in some embodiments the at least one fluid deflection structure includes a substantially straight fluid deflection structure. For example, in some embodiments the at least one fluid deflection structure includes a substantially curved fluid deflection structure.

Some embodiments include a particle retaining structure that is configured as a substantially planar structure. For example, a particle retaining structure can be configured as an attachment to the prosthesis, with a surface substantially mating with another surface of the prosthesis. See, e.g. FIG. 9. Some embodiments include a particle retaining structure that includes a mesh-like structure. For example, a particle retaining structure can be configured as a membrane surrounding the joint, with the particle retaining structure including a mesh-like structure configured to allow synovial fluid flow through the membrane. Some embodiments include a particle retaining structure that includes a filter structure. For example, a particle retaining structure can be configured as a 3-dimensional filter. Some embodiments include a particle retaining structure that includes a foam structure. For example, a particle retaining structure including a foam structure can include a surface configured to mate with a surface of the prosthesis, and a surface configured to retain particles in the foam structure. For example, a particle retaining structure including a foam structure can be configured to absorb particles from fluid flow directed at the foam structure by one or more fluid deflecting structures attached to the joint.

Some embodiments include a particle retaining structure that includes a group of projections, each of the projections positioned to contact the flow of synovial fluid and configured to retain particles present within the synovial fluid. For example, a particle retaining structure that includes a group of projections can include a coating on the external surfaces of the projections, the coating configured to trap some or all debris particles present in the fluid flow around the projections. For example, a particle retaining structure that includes a group of projections can include an adhesive coating on the external surface of the projections. For example, a particle retaining structure that includes a group of projections can include a hydrophobic coating on the external surface of the projections, the hydrophobic coating configured to attract hydrophobic particles in the joint fluid, such as hydrophobic plastic particles. For example, a particle retaining structure that includes a group of projections can include at least one type of antibody affixed to the external surfaces of the projections, the antibody of a size expected to bind to particulates within the joint fluid.

Some embodiments include a particle retaining structure that includes a first end, the first end affixed to the artificial joint prosthesis; and a second end, the second end affixed to an additional artificial joint component. For example, a particle retaining structure can include one or more membrane structures, each of which include a first end affixed to the artificial joint prosthesis, such as the acetabular liner of a hip joint, and a second end affixed to an additional artificial joint component, such as the region adjacent to the prosthesis-bone interface on the femoral component of the prosthesis. Some embodiments include a particle retaining structure that is affixed to a surface of the artificial joint prosthesis. For example, a particle retaining structure can be configured to reversibly mate with a surface of one or more components of a artificial joint. Some embodiments include a particle retaining structure that is affixed to a plurality of surfaces of the artificial joint prosthesis. Some embodiments include a particle retaining structure that is affixed to a plurality of components of the artificial joint prosthesis. See, for example, FIGS. 1-4.

Some embodiments include at least one particle retaining structure including a plurality of apertures. For example, the plurality of apertures can be configured to be of a size and shape to physically entrap the expected particles in the joint fluid. For example, a particle retaining structure can include a plurality of apertures having a diameter less than approximately 0.05 millimeters (mm). See, for example, U.S. Pat. No. 5,378,228 "Method and Apparatus for Joint Fluid Decompression and Filtration with Particulate Debris Collection," to Schmalzried and Jasty, which is incorporated herein by reference. Some embodiments include at least one particle retaining structure including a structure configured to retain non-physiological particles present in the synovial fluid. For example, the structure configured to retain non-physiological particles present in the synovial fluid can include apertures of the correct size and shape to retain the expected non-physiological particles in the synovial fluid. For example, the structure configured to retain non-physiological particles present in the synovial fluid can include a coating expected to bind to non-physiological particles, such as a coating including one or more antibodies, or a coating containing one or more chemically reactive species. Some embodiments include at least one particle retaining structure including a structure configured to retain particles containing artificial materials. For example, the structure configured to retain non-physiological particles present in the synovial fluid can include a magnetic coating configured to bind ferromagnetic particles present in the fluid.

Some embodiments include a artificial joint prosthesis including at least two components, each of which include at least one fluid deflection structure positioned on a non-contact surface. See, for example, FIGS. 1-4. Some embodiments include at least two components: a first component which includes at least one fluid deflection structure affixed to a non-contact surface; and a second component which includes at least one particle retaining structure affixed to a surface. The first component and the second component are positioned, sized and fabricated from materials selected to be compatible with each other. For example, the fluid deflection structure affixed to a non-contact surface of the first component is of a size, shape and position to deflect joint fluid flow towards the particle retaining structure affixed to the surface of the second component. For example, the fluid deflection structure affixed to a non-contact surface of the first component is of a size, shape and position to deflect joint fluid flow away from an exit structure of a particle retaining structure configured for linear fluid flow and affixed to the surface of the second component. Some embodiments include a artificial joint prosthesis including at least two components, each of which include at least one fluid deflection structure, and each of which include the mechanism attached to the fluid deflection structure, each of the mechanism operable to move each of the fluid deflection structure to direct synovial fluid away from the bone-prosthesis interface in vivo in the direction of the at least one particle retaining structure.

Some embodiments include a artificial joint prosthesis including: an aperture in the non-contact surface of the artificial joint prosthesis; a substantially round cavity in the artificial joint prosthesis adjacent to the aperture; a mechanism including a substantially round element of a size and shape to correspond to the substantially round cavity, the substantially round element positioned within the substantially round cavity and configured to move within the substantially round cavity; and the at least one fluid deflection structure attached to the substantially round element and projecting through the aperture. For example, the axis of rotation of a fluid deflection structure attached to a substantially round element within a corresponding cavity can be defined by the size, shape and position of the aperture. For example, the axis of rotation of a fluid deflection structure attached to a substantially cylindrical element within a corresponding cavity can be defined by the size, shape and position of the cavity and the size, shape and position of the aperture.

Some embodiments include a artificial joint prosthesis including: at least one first magnet attached to the artificial joint prosthesis; and at least one second magnet attached to the fluid deflection structure, wherein the mechanism attached to the fluid deflection structure is configured to move in accord with a magnetic field established by the at least one first magnet. Some embodiments include a artificial joint prosthesis including: at least one first magnet attached to the artificial joint prosthesis; and least one second magnet attached to the fluid deflection structure, wherein the mechanism attached to the fluid deflection structure is configured to allow the at least one second magnet to move the fluid deflection structure in accord with a magnetic field established by the at least one first magnet.

For a more complete understanding of the embodiments, reference now is made to the following descriptions taken in connection with the accompanying drawings. The use of the same symbols in different drawings typically indicates similar or identical items, unless context indicates otherwise.

With reference now to FIG. 1, shown is an example of an artificial hip joint prosthesis depicted in vivo in cross-section that serves as a context for introducing one or more artificial joint prostheses including fluid deflecting structures as described herein. The artificial hip joint prosthesis depicted in FIG. 1 is depicted in cross-section in vivo in a resting, or not significantly physiologically flexed, position. The cross-section view depicted in FIG. 1 is a substantially planar view of a vertical cross-section through the hip joint. The embodiment illustrated in FIG. 1 depicts a hip joint prosthesis including: a bone-facing surface of a hip joint prosthesis, the bone-facing surface configured to face a bone-prosthesis interface in vivo; a non-contact surface of the hip joint prosthesis, the non-contact surface adjacent to the bone-facing surface of the hip joint prosthesis; at least one fluid deflection structure positioned adjacent to the non-contact surface, the fluid deflection structure positioned to deflect synovial fluid away from the bone-prosthesis interface in vivo; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

FIG. 1 illustrates a hip joint prosthesis 100 in vivo, with prosthetic components including an acetabular shell 170, and acetabular liner 175, and a femoral component. The femoral component includes a femoral head component 182 and a femoral stem component 187. In some contexts, an acetabular shell 170 is referred to as an acetabular cup. A synovial membrane 190 forms the boundary of the joint region that includes synovial fluid. A particle retaining structure 195 is formed as a membrane-like structure surrounding the joint, within the boundary of the synovial membrane 190. The prosthetic components 170, 175, 182, 187 are respectively attached to a pelvic bone 160 and femur 150. The acetabular liner 175 includes a bone-facing surface 110. The acetabular shell 170 includes a bone-facing surface 112. The femoral stem component 187 includes a bone-facing surface 115. The bone-facing surfaces 110, 112, 115 of the prosthetic components 170, 175, 187 in contact with the bone form bone-prosthesis interfaces 120 in vivo. The particle retaining structure 195 is attached to a surface of the femoral stem 187 at one end of the particle retaining structure 195 and to a surface of the acetabular liner 175 at the other end of the particle retaining structure 195. In some embodiments wherein the particle retaining structure 195 is attached to two components of the hip prosthesis as illustrated in FIG. 1, the particle retaining structure 195 includes one or more collapsible structures. See U.S. Pat. No. 5,514,182 "Prosthetic Joint with Semipermeable Capsule with Reinforcing Ribs," to Shea, which is incorporated herein by reference.

The hip joint prosthesis 100 depicted in FIG. 1 includes several regions with non-contact surfaces. As shown in FIG. 1, the acetabular liner 175 includes an edge region with a non-contact surface 130. The non-contact surface 130 of the acetabular liner 175 is a surface of the acetabular liner 175 that is predicted to not come in contact with the bone (e.g. the pelvis 160) or a surface of another component of the artificial hip joint (e.g. the femoral head 182) during normal physiological use in vivo. The non-contact surface 130 of the acetabular liner 175 includes synovial fluid deflecting structures 140 positioned adjacent to the surface. In some embodiments, the non-contact surface of an artificial hip prosthesis includes an edge region of a liner of a acetabular component of the hip joint prosthesis. In some embodiments, the non-contact surface of an artificial hip prosthesis includes an edge region of a shell of a acetabular component of the hip joint prosthesis. Also as shown in FIG. 1, the femoral stem 187 includes a region with a non-contact surface 135. The non-contact surface 135 of the femoral stem 187 is a surface of the femoral stem 187 that is predicted to not come in contact with the bone (e.g. the femur 150) or a surface of another component of the artificial hip joint (e.g. the acetabular liner 175) during normal physiological use in vivo. The non-contact surface 135 of the femoral stem 187 includes synovial fluid deflecting structures 145 positioned adjacent to the surface. In some embodiments, the non-contact surface of an artificial hip prosthesis includes an edge region of a head of a femoral component of the hip joint prosthesis (see, e.g. FIG. 5). In some embodiments, the non-contact surface of an artificial hip prosthesis includes an edge region of a stem of a femoral component of the hip joint prosthesis.

FIG. 1 illustrates that some embodiments include a plurality of fluid deflection structures 140, 145, with attached mechanisms, positioned on more than one non-contact surface 130, 135 of the artificial hip prosthesis. In some embodiments, only one region with a non-contact surface has adjacent one or more fluid deflection structures and associated mechanisms. For example, in some embodiments, fluid deflection structures 140 and associated mechanisms are positioned adjacent to only the non-contact surface 130 of the acetabular liner 175. For example, in some embodiments, fluid deflection structures 145 and associated mechanisms are positioned adjacent to only the non-contact surface 135 of the femoral stem 187. Some embodiments also include fluid deflection structures without attached mechanisms (e.g. passive fluid deflection structures), configured to act in combination with the fluid deflection structures 145 with associated mechanisms to divert synovial fluid flow towards the particle retaining structure 195. The fluid deflection structures 140, 145 are positioned to direct joint fluid flow toward the particle retaining structure 195.

In some embodiments, the at least one fluid deflection structure, with attached mechanisms, positioned on the non-contact surface of an artificial hip prosthesis includes at least one flange structure positioned to extend from the non-contact surface. The flange structure is of a size and shape to deflect synovial fluid flow away from one or more of the bone-prosthesis interfaces 120 in vivo and towards the particle retaining structure 195. The flange structure is of a size and shape to mitigate synovial fluid pressure at one or more of the bone-prosthesis interfaces 120 in vivo during physiological use of the joint. For example, in some embodiments, the at least one flange structure is positioned to extend from the non-contact surface at an angle substantially between 10 degrees and 80 degrees of a plane established by the contact surface and relative to the bone-facing surface of the hip joint prosthesis. For example, in some embodiments, the at least one flange structure is positioned to extend from the non-contact surface at an angle substantially between 100 degrees and 170 degrees of a plane established by the contact surface and relative to the bone-facing surface of the hip joint prosthesis. For example, in some embodiments, the at least one flange structure is positioned to extend from the non-contact surface at a substantially right angle from a plane established by the contact surface and relative to the bone-facing surface of the hip joint prosthesis. The flange structure can include a first end adjacent to the non-contact surface and a second end distal to the non-contact surface, wherein the flange structure is widest at the first end and narrowest at the second end. The flange structure can include a first end connected to the non-contact surface and a second end distal to the non-contact surface, wherein the flange structure tapers from a widest point at the first end to a narrow point at the second end. The flange structure can include at least one flange structure with a curvilinear structure. The flange structure can include at least one flange structure with a substantially flat or linear structure when not under pressure from synovial fluid, and a curvilinear structure when under pressure.

As shown in FIG. 1, a fluid deflection structure 140, 145 can include a first end adjacent to the non-contact surface and a second end distal to the non-contact surface. In some embodiments, a fluid deflection structure can include a substantially planar structure. In some embodiments, a fluid deflection structure can include a tapered or angular structure. In some embodiments, a fluid deflection structure can include a collar structure around an edge of a non-contact surface. As shown in FIG. 1, some embodiments include a plurality of fluid deflection structures 140, 145. As shown in FIG. 1, some embodiments include a plurality of fluid deflection structures 140, 145 configured to direct synovial fluid flow toward a single particle retaining structure 195. Some embodiments include at least one acetabular liner 175, wherein the acetabular liner 175 includes at least one fluid deflection structure 140 positioned adjacent to the non-contact surface 130; and at least one femoral stem 187, wherein the femoral stem 187 includes at least one fluid deflection structure 145 positioned adjacent to the non-contact surface 135.

In some embodiments, a fluid deflection structure can include a plurality of linear projections. For example, a fluid deflection structure can include one or more hair-like or ciliated structures. The plurality of linear projections are of a size and shape so that the linear projections, in the aggregate, deflect synovial fluid flow away from one or more of the bone-prosthesis interfaces 120 in vivo and direct synovial fluid flow toward the particle retaining structure 195. The specific size and number of linear projections will depend on the embodiment, relative to factors including the size of the joint, the estimated synovial fluid pressure in the joint during physiological use, and the flexibility of the material used to fabricate the fluid deflection structure including a plurality of linear projections. The specific size and number of linear projections will also depend on the size, shape and position of the one or more particle retaining structure 195 in the embodiment. In some embodiments, the plurality of linear projections are positioned to extend from the non-contact surface at an angle substantially between 10 degrees and 80 degrees of a plane established by the contact surface and relative to the bone-facing surface of the hip joint prosthesis. In some embodiments, the plurality of linear projections are positioned to extend from the non-contact surface at an angle substantially between 100 degrees and 170 degrees of a plane established by the contact surface and relative to the bone-facing surface of the hip joint prosthesis. In some embodiments, the plurality of linear projections are positioned to extend from the non-contact surface at an substantially right angle from a plane established by the contact surface and relative to the bone-facing surface of the hip joint prosthesis.

Some embodiments include at least one fluid deflection structure positioned adjacent to the non-contact surface wherein the at least one fluid deflection structure includes a substantially straight fluid deflection structure. The substantially straight fluid deflection structure can be, for example, substantially linear or substantially planar. The substantially straight fluid deflection structure can be, for example, substantially straight in the absence of synovial fluid pressure but flex or bend in the presence of synovial fluid pressure during in vivo use of the artificial hip joint. Some embodiments include at least one fluid deflection structure positioned on the non-contact surface including a substantially curved fluid deflection structure. The substantially curved fluid deflection structure can further curve or bend in the presence of synovial fluid pressure during in vivo use of the artificial hip joint.

In some embodiments, a fluid deflection structure of any initial shape can be configured to be substantially rigid at physiological conditions when the artificial joint is utilized in vivo. For example, a fluid deflection structure can be fabricated from a material in a suitable size and shape that is expected to be substantially rigid during in vivo use of the artificial hip joint prosthesis. The rigidity of a fluid deflection structure may be desirable, for example to enhance angular momentum in the synovial fluid. In some embodiments, the attached mechanism includes a projection that serves as a central stabilizing structure within the fluid deflection structure. For example, the mechanism can operate to move an attached rod, with the rod serving as a central stabilizing structure within the fluid deflection structure. The rod may be fabricated a substantially rigid material, with the remainder of the fluid deflection structure fabricated from a substantially flexible material.

In some embodiments, a fluid deflection structure of any initial shape can be configured to be flexible at physiological conditions when the artificial joint is utilized in vivo. For example, a fluid deflection structure can be fabricated from a material in a suitable size and shape that is expected to be flexible during in vivo use of the artificial hip joint prosthesis. The flexibility of a fluid deflection structure may be desirable, for example, to convert the fluid pressure resulting from joint motion in one direction into synovial fluid motion in an inclined or orthogonal direction during use of the artificial hip joint prosthesis. For example, in some embodiments the at least one fluid deflection structure positioned on the non-contact surface can be configured to flex to a degree sufficient to permit a larger synovial fluid flow rate away from the bone-prosthesis interface during periods of increased synovial fluid pressure in the region of the non-contact surface when the artificial joint is utilized in vivo at physiological conditions, and to permit a smaller synovial fluid flow rate away from the bone-prosthesis interface during periods of reduced synovial fluid pressure when the artificial joint is utilized in vivo at physiological conditions. For example, in some embodiments the at least one fluid deflection structure positioned on the non-contact surface is configured to flex to a degree sufficient to permit an increased synovial fluid flow rate away from the bone-prosthesis interface in response to increased fluid pressure in a region adjacent to the bone-prosthesis interface.

FIG. 1 illustrates a particle retaining structure 195 configured as a sheath surrounding the joint, the sheath having a first end connected to the femoral stem 187 and the second end connected to the acetabular liner 175. The particle retaining structure 195 illustrated in FIG. 1 is configured to allow synovial fluid to pass through the structure, while retaining particles from the fluid flow on the structure. Not all particles need be retained by the particle retaining structure 195. Some embodiments include particle retaining structures that are configured to only sequester some types of particles, depending on their physical properties. Some embodiments include particle retaining structures that include a plurality of apertures. For example, particle retaining structures including apertures will not sequester particles too large or too small to be sequestered within the apertures. For example, particle retaining structures including magnetic elements will sequester ferromagnetic particles, and not inhibit non-ferromagnetic particles. For example, particle retaining structures including antibodies will sequester particles with surface molecules that bind the antibodies, and not retain particles that do not include surface molecules that bind the antibodies. For example, particle retaining structures including a hydrophobic surface will sequester particles with surface molecules that interact with the hydrophobic surface, and not retain particles that do not include surface molecules that interact with the hydrophobic surface. Some embodiments include particle retaining structures that include a mesh-like structure, for example with apertures that physically entrap particles of a specific size range. Some embodiments include particle retaining structures that include a filter structure, for example with channels that physically entrap particles of a specific size range. Some embodiments include particle retaining structures that include a foam structure, for example foam with a surface adhesive configured to adhere to particles physically pressed against the foam by the deflected flow of the joint fluid. Some embodiments include particle retaining structures that include a structure configured to retain non-physiological particles present in the synovial fluid, for example through specific binding to chemical elements present on the surface of the particle retaining structure. Some embodiments include particle retaining structures that include a structure configured to retain particles including artificial materials. For example, a particle retaining structure can include one or more chemical elements configured to bind to specific artificial materials (e.g. plastics or ceramics). For example, a particle retaining structure can include a magnetized surface configured to capture ferromagnetic particles. In some embodiments, a particle retaining structure is configured to capture particles through multiple means (e.g. with a magnetized surface as well as a set of apertures configured to sequester particles of a specific size range).

Some embodiments include particle retaining structures that are configured as substantially planar structures. For example, a particle retaining structure having a first end connected to the femoral stem 187 and the second end connected to the acetabular liner 175 as illustrated in FIG. 1 can be configured with the particle retaining structure including a series of substantially planar structures, each with a connected first end and second end. As an additional example, a particle retaining structure can be configured as a substantially planar structure including a surface configured to mate with a surface of a component of the prosthesis.

Some embodiments include particle retaining structures as a group of projections. Each of the projections can be positioned to contact the flow of synovial fluid and configured to retain particles present within the synovial fluid. The group of projections can be shaped as substantially linear projections, for example as hair-like or ciliated structures. The group of projections include surfaces structured to bind and sequester particles from the joint fluid. The projections can be fabricated to bind some particles in the joint fluid based on the structure of specific particles. For example, the particle retaining structures configured as projections can include hydrophobic surfaces. For example, the particle retaining structures configured as projections can include surfaces with attached antibodies. For example, the particle retaining structures configured as projections can include magnetic surfaces. Some embodiments include particle retaining structures configured as projections with different types of surfaces. For example, a group of projections can include magnetized surfaces as well as those including specific antibodies.

In some embodiments, at least one particle retaining structure is affixed to a surface of the hip joint prosthesis. In some embodiments, at least one particle retaining structure is affixed to a plurality of surfaces of the hip joint prosthesis. In some embodiments, at least one particle retaining structure is affixed to a plurality of components of the hip joint prosthesis. See, e.g. FIGS. 1-4 as associated text.

FIG. 1 depicts each of the fluid deflection structures 140 associated with the acetabular liner 175 positioned adjacent to the non-contact surface 130 of the liner and attached to a mechanism 143. Each of the mechanisms 143 is configured to fit within a cavity 173 in the acetabular liner 175. Each cavity 173 in the acetabular liner 175 is positioned adjacent to the non-contact surface 130 of the acetabular liner 175, with an aperture connecting the cavity 173 and the non-contact surface 130. In the embodiment illustrated, no mechanisms are attached to the fluid deflecting structures 145 positioned adjacent to the non-contact surface 135 in the femoral stem component 187. The fluid deflecting structures 145 positioned adjacent to the non-contact surface 135 in the femoral stem component 187 are attached directly to the adjacent non-contact surface 135. Some embodiments include mechanisms attached to the fluid deflecting structures positioned adjacent to all of the non-contact surfaces of an artificial hip joint prosthesis. Some embodiments include mechanisms attached to the fluid deflecting structures positioned adjacent to less than all, or a subset, of the non-contact surfaces of an artificial hip joint prosthesis. The mechanisms can include, for example, electric motors, piezoresistent components, hydraulic pistons, and magnetic components as discussed herein. A particular embodiment can include mechanisms including the same or different components from each other. A particular embodiment can include mechanisms operating under the same or different principles from each other, including forces moving the attached fluid deflecting structure(s), the flexibility of the attached fluid deflecting structure(s), and the size of the attached fluid deflecting structure(s).

FIG. 2 illustrates aspects of the artificial hip joint prosthesis embodiment as shown in FIG. 1. The artificial hip joint prosthesis 100 depicted in FIG. 2 is depicted in cross-section in vivo in a flexed or bent position. As in FIG. 1, the view depicted in FIG. 2 is a substantially planar view of a vertical cross-section through the hip joint in vivo. As illustrated in FIG. 2, the artificial hip joint prosthesis 100 includes an acetabular shell 170, an acetabular liner 175 and a femoral component including a femoral head 182 and femoral stem 187. A particle retaining structure 195 is formed as a membrane-like structure surrounding the joint and attached to both the acetabular liner 175 and the femoral component. A particle retaining structure 195 as illustrated can be formed with a mesh structure including apertures of a size and shape to sequester particles of a size range (e.g. 0.05 to 0.01 mm). The particle retaining structure 195 lies within the boundary of the synovial membrane 190, and therefore within the expected flow of synovial joint fluid in vivo.

FIG. 2 depicts the joint in a flexed position, which is expected to result in a transient increase in synovial fluid pressure at the bone-prosthesis interface regions put into closer proximity during the joint repositioning. For example, FIG. 2 illustrates that regions of the non-contact surface 130A of the acetabular liner 175 and a region of the non-contact surface 135A of the femoral stem 187 are being placed in closer proximity due to the joint repositioning (e.g. relative to the joint position illustrated in FIG. 1). Correspondingly, FIG. 2 shows that regions of the non-contact surface 130B of the acetabular liner 175 and a region of the non-contact surface 135B of the femoral stem 187 are moved away from each other due to the joint repositioning (e.g. relative to the joint position illustrated in FIG. 1). The particle retaining structure 195 is configured to bend or shift in accord with the joint.

For a transient period during and immediately after the joint flexing or bending from the position illustrated in FIG. 1 to the position illustrated in FIG. 2, there is an increase in synovial fluid pressure in the region between the non-contact surface 130A of the acetabular liner 175 and a region of the non-contact surface 135A of the femoral stem 187. This results in an increased synovial fluid flow across the joint, as illustrated by the dotted arrows across the artificial joint 100 in FIG. 2. The joint bending, and the associated localized synovial fluid pressure increase, results in the flexing of the fluid deflecting structures 140A attached to the non-contact surface 130A of the acetabular liner 175. The joint bending, and the associated localized synovial fluid pressure increase, also results in the flexing of the fluid deflecting structures 145A attached to the non-contact surface 135A of the femoral stem 187. The fluid deflecting structures 140 B, 145B attached to the non-contact surfaces 130B, 135B of the acetabular liner 175 and the femoral stem 187 not subject to increased synovial fluid pressure do not bend or flex in the same manner as the fluid deflecting structures 140A, 145A subject to the localized synovial fluid pressure increase associated with the joint bending. The increased synovial fluid flow across the joint, as illustrated by the dotted arrows across the artificial joint 100 in FIG. 2, direct the flow of joint fluid toward a surface of the particle retaining structure 195. Particulates in the fluid flow coming into contact with the particle retaining structure 195 are sequestered on the surface of or within the structure of the particle retaining structure 195.

Some embodiments include mechanisms attached to the fluid deflecting structures that are configured to respond to increases in fluid pressure, such as through normal physiological joint movement. For example, some embodiments include a piezoelectric element within the mechanism, and a rod extending from the fluid deflecting structure through the mechanism, the rod configured to transmit pressure from the fluid to the piezoelectric element. The transient pressure increase in the joint at that location, transmitted from the joint fluid through the fluid deflection structure to the mechanism, will result in a localized effect on the mechanism subject to fluid pressure at a given time. Correspondingly, a transient decrease in fluid pressure will result in decreased pressure on the mechanism. The changes in joint fluid pressure during physiological movement of the joint are expected to be transient and localized within the joint, with corresponding effects on fluid deflection structures and attached mechanisms.

FIG. 2 illustrates fluid deflection structures 140A under higher transient fluid pressure than corresponding fluid deflection structures 140B in another region of the artificial joint. The mechanisms 143A attached to the fluid deflection structures 140A under increased transient fluid pressure will respond to this pressure, for example with increased opposing force on the fluid deflecting structures 140A. The fluid deflection structures 140B under a reduced or lower transient fluid pressure have attached mechanisms 143B that will, similarly, respond to the reduced or lower transient fluid pressure in that region of the joint.

FIG. 3 illustrates a hip joint prosthesis 100 in vivo, with prosthetic components including an acetabular liner 175, and a femoral stem 187. The embodiment depicted in FIG. 3 is similar to that shown in FIG. 1 from an external viewpoint. Since the viewpoint of FIG. 3 is external, the mechanisms attached to the fluid deflection structures 140 are not visible. The view illustrated in FIG. 3 is a view of the artificial hip joint prosthesis in vivo in a resting, or not significantly physiologically flexed, position. The view illustrated in FIG. 3 is a view of the artificial hip joint prosthesis in vivo without the surrounding skin, ligaments and other surrounding tissues depicted. An embodiment of an artificial hip joint prosthesis such as illustrated in FIG. 3 can include an acetabular shell, although it is not visible in the view depicted in FIG. 3.

FIG. 3 shows that the hip joint prosthesis 100 includes a visible acetabular liner 175 positioned adjacent to the pelvis 160, forming a bone-prosthesis interface 120. A particle retaining structure 195 is connected at a first end to the acetabular liner 175 and to the femoral stem 187 at a second end. The acetabular liner 175 has a plurality of associated fluid deflecting structures 140 configured to deflect joint fluid flow toward the particle retaining structure 195. The fluid deflecting structures 140 attached to the acetabular liner 175 are positioned around the circumference of the acetabular liner 175 in a region of the non-contact surface of the acetabular liner 175. In the view shown in FIG. 3, the hip joint prosthesis 100 is in a resting position and the synovial fluid flow in the joint is not under significant pressure at any particular location. The fluid deflecting structures 140 attached to the acetabular liner 175 are, therefore, positioned substantially perpendicularly relative to the surface of the acetabular liner 175 facing the interior region of the joint 100. The fluid deflecting structures 140 attached to the acetabular liner 175 are of a size, shape and material fabrication to not impede motion of the joint 100, including being predicted to not come into contact with the femoral head 182 or the femoral stem 187 during routine physiological activity. Similarly, particle retaining structure 195 is configured to not impede routine joint motion.

FIG. 3 also depicts that the hip joint prosthesis 100 includes a femoral head 182 and a femoral stem 187. A plurality of fluid deflecting structures 145 are attached to the femoral stem 187 directly, without associated mechanisms. The plurality of fluid deflecting structures 145 attached to the femoral stem 187 are positioned around the circumference of the femoral stem 187 in a region of the non-contact surface 135 of the femoral stem 187. The particle retaining structure 195 is affixed to the femoral stem 187 at a position distal to the ring formed by the plurality of fluid deflecting structures 145. The particle retaining structure 195 is affixed to the acetabular liner 175 at a position distal to the ring formed by the plurality of fluid deflecting structures 140. The particle retaining structure 195 is within the synovial membrane boundary 190 but outside of the rings formed by the fluid deflecting structures 140, 145. As noted above, in the view shown in FIG. 3, the hip joint prosthesis 100 is in a resting position and the synovial fluid flow in the joint is not under significant pressure at any particular location. The fluid deflecting structures 145 attached to the non-contact surface 135 of the femoral stem 187 are, therefore, positioned substantially perpendicularly relative to the surface of the femoral stem 187 facing the interior region of the joint 100. The fluid deflecting structures 145 attached to the femoral stem 187 are of a size, shape and material fabrication to not impede motion of the joint 100, including being predicted to not come into contact with the femoral head 182 or the acetabular liner 175 during routine physiological activity. The fluid deflecting structures 145 attached to the femoral stem 187 are configured to bend or flex in accord with synovial fluid pressure, in accord with the fluid deflecting structures 140 that are attached to mechanisms.

FIG. 4 depicts a hip joint prosthesis 100 in vivo during physiological movement of the joint 100. The view illustrated in FIG. 4 is an external view of the joint 100, similar to the view depicted in FIG. 3. As with the viewpoint shown in FIG. 3, the mechanisms attached to the fluid deflection structures 140 are not visible in FIG. 4. The artificial hip joint prosthesis 100 depicted in FIG. 4 is depicted in vivo in a flexed or bent position, similar to the view depicted in cross-section in FIG. 2. As illustrated in FIG. 4, the artificial hip joint prosthesis 100 includes an acetabular liner 175, a femoral head 182 and a femoral stem 187. A particle retaining structure 195 is connected at a first end to the acetabular liner 175 and to the femoral stem 187 at a second end. FIG. 4 depicts the joint during or immediately after moving to a flexed position, which is expected to result in a transient increase in synovial fluid pressure at the bone-prosthesis interface regions put into closer proximity during the joint repositioning. For example, FIG. 4 illustrates that regions of the non-contact surface 130A of the acetabular liner 175 and a region of the non-contact surface 135A of the femoral stem 187 are being placed in closer proximity due to the joint repositioning (e.g. relative to the joint position illustrated in FIG. 3). Correspondingly, FIG. 4 shows that regions of the non-contact surface 130B of the acetabular liner 175 and a region of the non-contact surface 135B of the femoral stem 187 are moved away from each other due to the joint repositioning (e.g. relative to the joint position illustrated in FIG. 3).

As also described above, for a transient period during and immediately after the joint flexing or bending from the position illustrated in FIG. 3 to the position illustrated in FIG. 4, there is an increase in synovial fluid pressure in the region between the non-contact surface 130A of the acetabular liner 175 and a region of the non-contact surface 135A of the femoral stem 187. This results in an increased synovial fluid flow across the joint, as illustrated by the dotted arrows across the joint 100 in FIG. 4. The joint bending, and the associated localized synovial fluid pressure increase, results in pressure transferred as force on the mechanisms attached to the fluid deflecting structures 140A adjacent to the non-contact surface 130A of the acetabular liner 175. The joint bending, and the associated localized synovial fluid pressure increase, also results in pressure transferred as force on the mechanisms attached to the fluid deflecting structures 145A attached to the non-contact surface 135A of the femoral stem 187. As shown in FIG. 4, the fluid deflecting structures 140 B, 145B attached to the non-contact surfaces 130B, 135B of the acetabular liner 175 and the femoral stem 187 are not subject to increased synovial fluid pressure. The mechanisms attached to the fluid deflecting structures 140 B, 145B not under increased transient fluid pressure will, therefore, not respond in the same manner as mechanisms attached to the fluid deflecting structures 140A, 145A subject to the localized synovial fluid pressure increase associated with the joint bending. The combination of localized synovial fluid pressure change and diversion of the fluid flow by the fluid deflecting structures 140, 145 causes fluid flow to be directed towards the inner surface of the particle retaining structure 195. In particular, joint fluid flow is directed towards the inner surface of the particle retaining structure 195 in the region of the particle retaining structure 195 adjacent to the fluid deflecting structures 140B, 145B which are not subject to increased synovial fluid pressure (e.g. as illustrated by the dotted arrow across the joint in FIG. 4).

FIG. 5 shows components of an artificial hip joint prosthesis ex-vivo. These components can be included in some embodiments of an artificial hip joint prosthesis, although not all embodiments will include all of the components depicted in FIG. 5. FIG. 5 depicts that the artificial hip joint prosthesis includes an acetabular shell 170. The acetabular shell 170 is configured to fit around an acetabular liner 175. The acetabular liner 175 includes a non-contact surface 130. A plurality of non-actuated fluid deflecting structures 540 are attached to the non-contact surface 130 of the acetabular liner 175. The non-actuated fluid deflecting structures 540 do not have attached mechanisms. The non-actuated fluid deflecting structures 540 are configured to bend or flex in response to joint fluid pressures in vivo. The artificial hip joint prosthesis also includes a femoral head 182 configured to attach to a femoral stem 187 through routine means. The femoral head 182 includes a non-contact surface 500. A actuated attachment 510 includes a surface configured to reversibly mate with the non-contact surface 500. The actuated attachment 510 includes a plurality of actuated fluid deflecting structures 520 attached to associated mechanisms 530. The mechanisms 530 are partially embedded within the structure of the actuated attachment 510. The fluid deflecting structures 520 with attached mechanisms 530 are oriented to project outward from the non-contact surface 500 when the actuated attachment 510 is positioned in place adjacent to the non-contact surface 500 of the femoral head 182. During use, the actuated attachment 510 is positioned adjacent to the non-contact surface 500 of the femoral head 182. The plurality of actuated fluid deflecting structures 520 attached to associated mechanisms 530 in the actuated attachment 510 are configured to move joint fluid in vivo through action of the mechanisms 530. The fluid deflecting structures 520 attached to associated mechanisms 530 are configured to work synergistically in vivo with the fluid deflecting structures 540 that do not have attached mechanisms and are attached to the non-contact surface 130 of the acetabular liner 175. The non-contact surfaces 130, 500, 135 depicted in FIG. 5 are each predicted to not come into direct contact with the adjacent surfaces of the artificial hip joint prosthesis during routine physiological use of the hip joint in vivo.

The femoral stem 187 includes a non-contact surface 135 with a plurality of attached particle retaining structures 545 configured as linear projections. The particle retaining structures 545 shown in FIG. 5 are configured to surround the femoral stem of the prosthesis and to project into the joint fluid surrounding the femoral stem in vivo. The particle retaining structures 545 include surfaces configured to retain particles in vivo. For example, in some embodiments, the particle retaining structures 545 can include magnetic surfaces, configured to adhere to ferromagnetic particles in the joint fluid and sequester those particles with the particle retaining structures 545. For example, in some embodiments, the particle retaining structures 545 can include attached antibodies on their surfaces, the antibodies configured to adhere to specific molecules on the surfaces of the particle retaining structures 545 and to retain those particles at the surfaces of the particle retaining structures 545. For example, in some embodiments, the particle retaining structures 545 can include adhesive on their surfaces, the adhesive configured to adhere and retain particles present in the joint fluid in vivo.

The fluid deflecting structures 520, 540 shown in FIG. 5 are depicted as substantially linear, or ciliated, structures. The dimensions of substantially linear fluid deflecting structures 520, 540 such as height and diameter, would depend on the particular embodiment. In particular, the substantially linear fluid deflecting structures 520, 540 should be constructed of a size, shape and material to not impede routine physiological use of the associated hip joint in vivo while still providing fluid deflection during joint motion (e.g. as described relative to FIGS. 2 and 4, above). Similarly, the positioning and number of the substantially linear fluid deflecting structures 520, 540 on the non-contact surfaces 130, 500 will depend on the specific embodiment. Factors to consider in the size, shape, positioning, number and material of the substantially linear fluid deflecting structures 520, 540 on the non-contact surfaces 130, 500 in various embodiments include the total size of the hip joint in vivo, the relative size of the hip joint components 170, 175, 182, 187, and the expected fluid pressures within the hip joint in vivo. The relative number, size and position of the actuated fluid deflecting structures 520 attached to mechanisms 530 to drive movement of the actuated fluid deflecting structures 520 relative to the number, size and position of non-actuated fluid deflecting structures 540 will vary by embodiment. The non-actuated fluid deflecting structures 540 will act synergistically with the actuated fluid deflecting structures 520 in vivo to deflect fluid within the joint. The position, spacing, size and shape of the non-actuated fluid deflecting structures 540 relative to the actuated fluid deflecting structures 520 on the artificial joint will determine the joint fluid flow and deflection in the entirety of the joint in vivo. The combination of the non-actuated fluid deflecting structures 540 and the actuated fluid deflecting structures 520 act in vivo to deflect joint fluid flow towards the particle retaining structures 545 and away from the prosthesis-bone interfaces.

Figure 6:
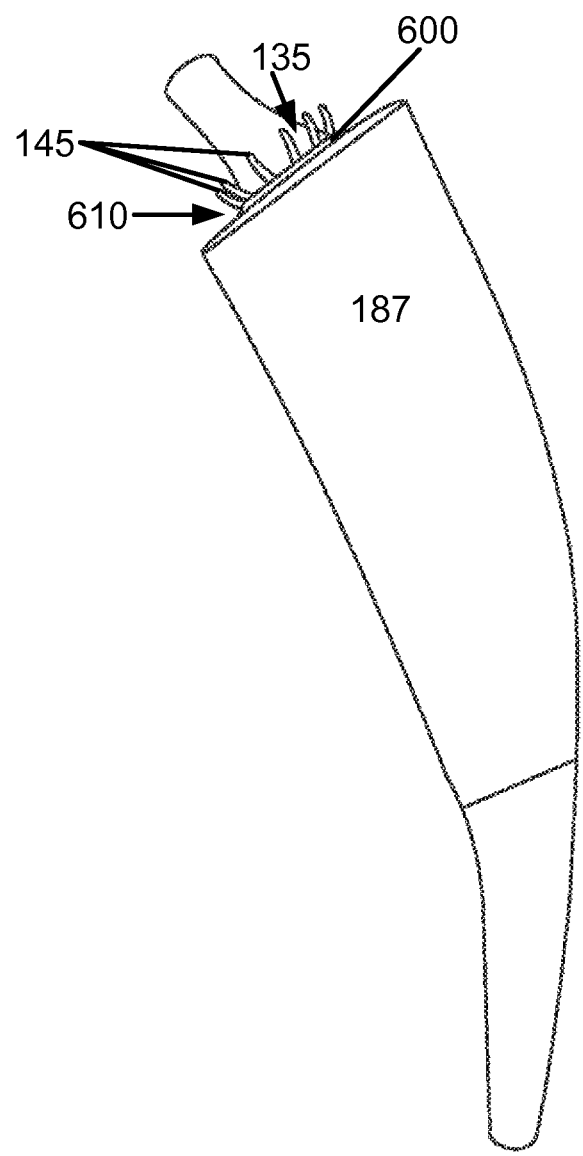
FIG. 6 shows a femoral component of an artificial hip joint.

FIG. 6 illustrates aspects of some embodiments of a femoral stem 187 with attached particle retaining structures 545 on a non-contact surface 135. As illustrated in FIG. 6, in some embodiments of a hip joint prosthesis, a non-contact surface 135 includes a plurality of particle retaining structures 545 attached to project at an angle from the non-contact surface 135. The plurality of particle retaining structures 545 are each attached to a band 600 at their terminal end closest to the non-contact surface 135. The band 600 is configured to secure each of the plurality of particle retaining structures 545 in position relative to the non-contact surface 135. The band 600 illustrated in FIG. 5 is shown as a single, unified, smooth band, but in some embodiments the band 600 can include multiple components, grooves or tabs configured to stabilize the band 600 relative to the non-contact surface 135. The band 600 is also stabilized relative to the non-contact surface 135 through placement in a groove 610 of the non-contact surface 135. The groove 610 of the non-contact surface 135 can have a single, substantially smooth surface, as shown in FIG. 6. In some embodiments, the groove 610 can include multiple channels or surfaces. For example, in some embodiments a groove 610 can include edge structures configured to mate with corresponding tab structures of a band 600 to functionally stabilize the band 600 relative to the non-contact surface 135. Although the particle retaining structures 545 shown in FIG. 6 are illustrated as substantially linear structures, some embodiments include a plurality of particle retaining structures 545 attached to a retaining band 600 wherein the particle retaining structures 545 are configured as flanges, ciliated structures, or other forms. Some embodiments include one or more particle retaining structures 545 configured as curved flanges encircling the non-contact region 135 of the femoral stem 187.

Although a band 600 and corresponding groove 610 are illustrated in FIG. 6 relative to a femoral stem 187, some embodiments include a band 600 and corresponding groove 610 on other components of an artificial joint, e.g. an acetabular cup. Although the band 600 and corresponding groove 610 are shown in FIG. 6 relative to an artificial hip joint prosthesis, some embodiments include one or more bands 600 with attached particle retaining structures 545 and corresponding grooves 610 on other types of artificial joints, e.g. an artificial knee or shoulder.

FIG. 7A shows aspects of a femoral stem 187 including a plurality of fluid deflecting structures 740 with attached mechanisms adjacent to a non-contact surface 135. A portion of the femoral stem 187 including the non-contact surface 135 is shown in an enlarged view in FIG. 7B to illustrate aspects of a fluid deflecting structure 740 and attached mechanism 730 relative to the non-contact surface 135. The non-contact surface 135 includes a series of apertures 700, with each of the plurality of fluid deflecting structures 740 projecting through a single aperture 700.

As illustrated and enlarged in FIG. 7B, a region of a fluid deflecting structure 740 traverses through a single aperture 700. Each of the apertures 700 is positioned between the external non-contact surface 135 and a cavity 710 in the femoral stem 187. The mechanism 730 attached to the fluid deflecting structure 740 is positioned entirely within the cavity 710. Each cavity 710 is of a size and shape that is larger, in particular wider, than the size of the adjacent aperture 700. Each of the fluid deflecting structures 740 includes a projection 720 at an end of the fluid deflecting structure 740 configured to fit within the cavity 710. The mechanism 730 is attached to the fluid deflecting structure 740 at the projection 720. The size and the shape of the projection 720 and associated mechanism 730 corresponds with the size and shape of the associated cavity 710 in a manner to stabilize the fluid deflecting structure 740 within the cavity 710 and associated aperture 700. The size and the shape of the projection 720 and associated mechanism 730 also corresponds with the size and shape of the associated cavity 710 so that the mechanism 530 can operate within the cavity 710 to influence movement of the fluid deflection structure 740. The size and shape of the cavity 710 can, for example, position the end of the fluid deflecting structure 740 with the projection at a particular angle relative to the non-contact surface 135. The size and shape of the cavity 710 can, for example, fix the end of the fluid deflecting structure 740 with the projection relative to the non-contact surface 135.

Figure 7:
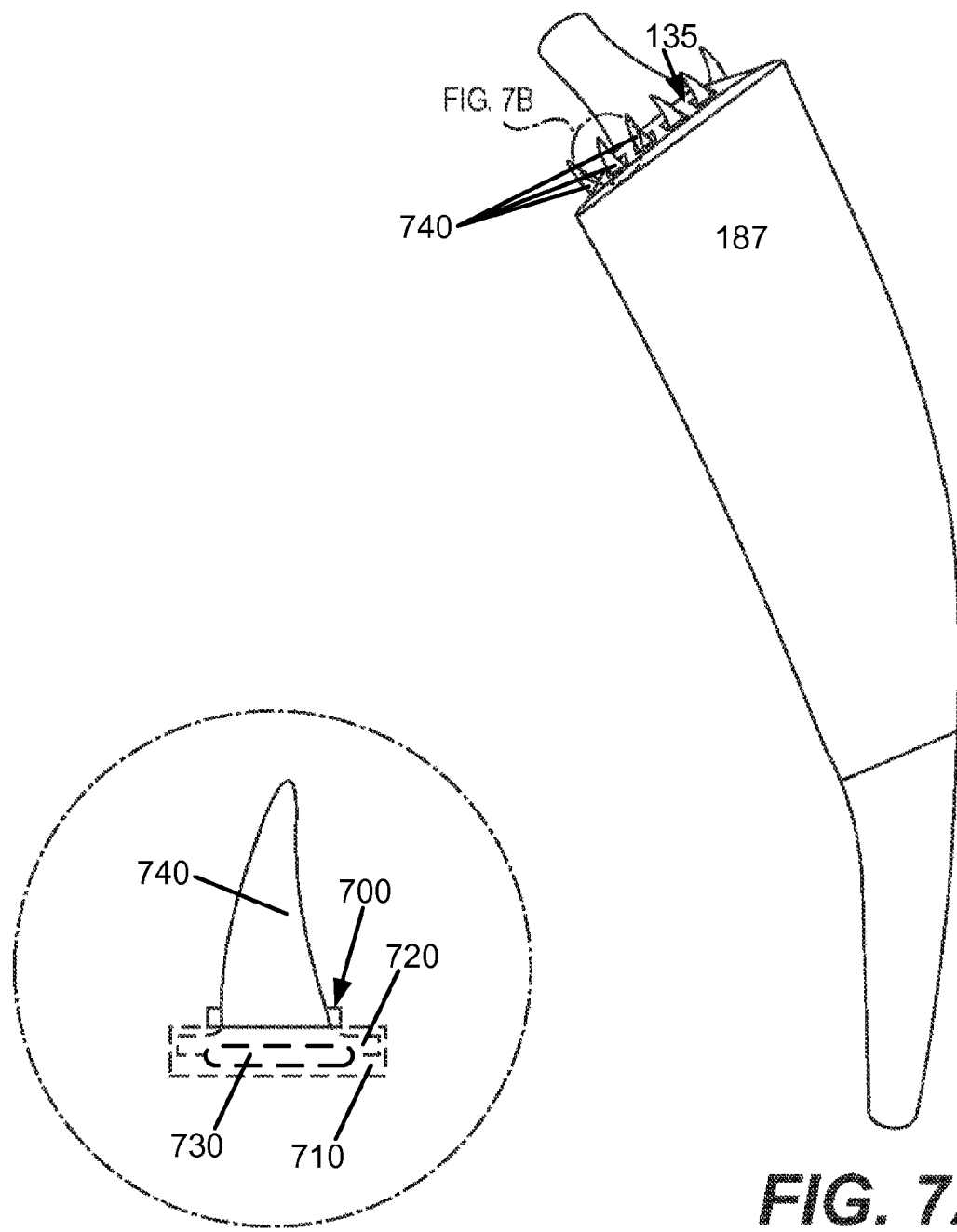
FIG. 7A illustrates a femoral component of an artificial hip joint, with a plurality of fluid deflection structures attached.
FIG. 7B shows a closer view of a fluid deflection structure attached to the femoral component of an artificial hip joint.

Although apertures 700, cavities 710 and corresponding projections 720 from the fluid deflecting structures 740 with attached mechanisms 530 are illustrated in FIG. 7 relative to a femoral stem 187, some embodiments include apertures 700, cavities 710 and corresponding projections 720 associated with the fluid deflecting structures with attached mechanisms 530 associated with non-contact regions on other components of an artificial joint, e.g. an acetabular cup or femoral head component. Although the apertures 700, cavities 710 and corresponding projections 720 from the fluid deflecting structures 740 with attached mechanisms 530 are shown in FIGS. 7A and 7B relative to an artificial hip joint prosthesis, some embodiments include one or more apertures 700, cavities 710 and corresponding projections 720 from the fluid deflecting structures 740 with attached mechanisms 530 on other types of artificial joints, e.g. an artificial knee or shoulder.

Figure 8:
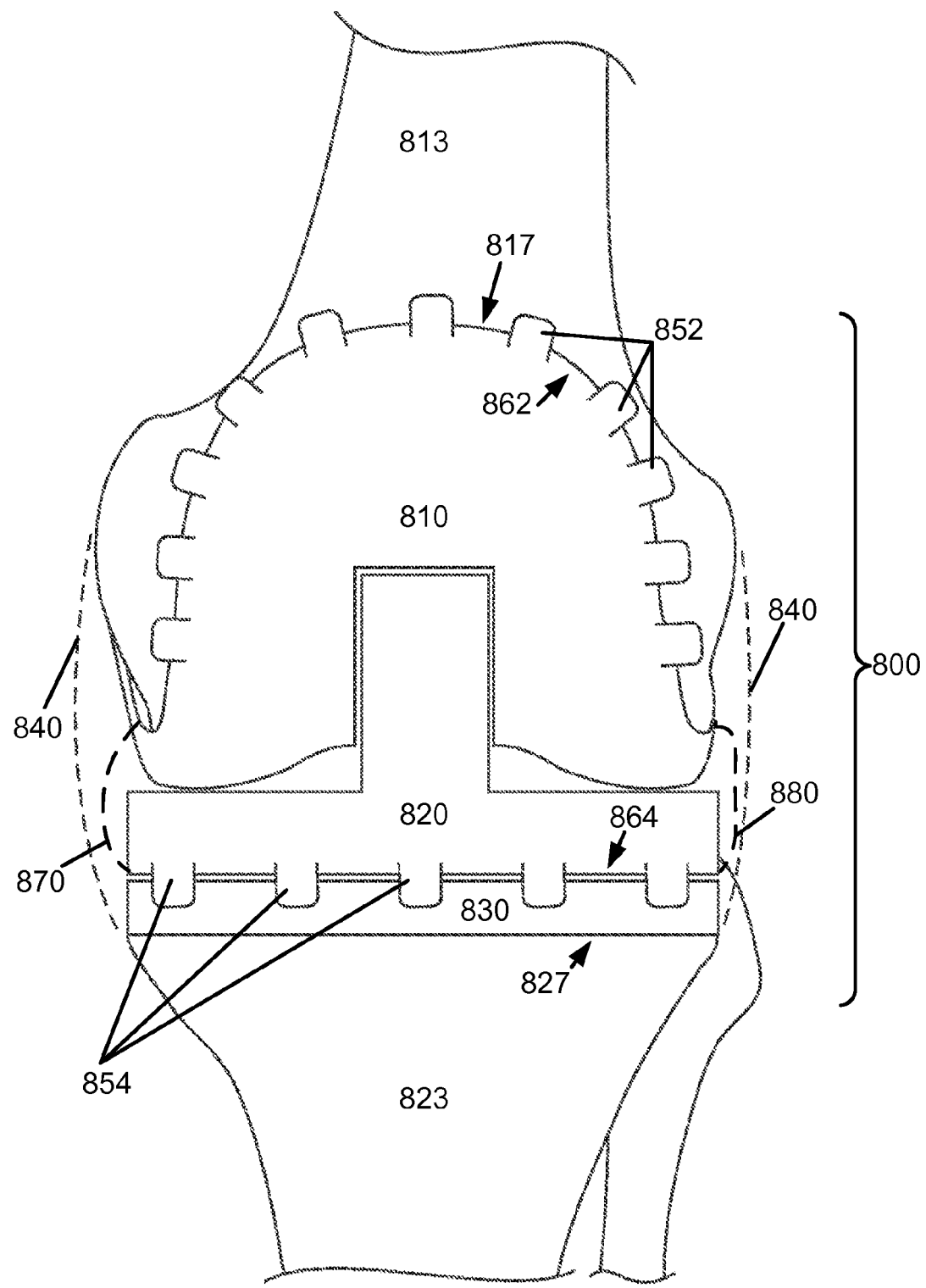
FIG. 8 depicts an external, frontal view of an artificial knee joint.

FIG. 8 illustrates aspects of an artificial knee joint 800 prosthesis in vivo. The artificial knee joint 800 prosthesis illustrated in FIG. 8 is shown in a frontal view, with the surrounding skin, ligaments and tissues removed for clarity of presentation. The artificial knee joint 800 shown in FIG. 8 includes components 830, 810 attached to both the femur 813 and the tibia 823. A synovial membrane border 840 is shown as a dotted line to roughly define the edge of the synovial fluid region of the artificial knee joint 800. In some embodiments, an artificial knee joint 800 prosthesis will be partial, i.e. not include all of the components illustrated in FIG. 8.

FIG. 8 shows a femur 813 including an attached femoral component 810 of an artificial knee joint 800 prosthesis. The femoral component 810 includes a bone-facing surface, which is positioned relative to the femur 813 in vivo to create a bone-prosthesis interface 817. The femoral component 810 also includes a non-contact surface 862. The non-contact surface 862 is a surface of the femoral component 810 that is predicted to not come into contact with other components of the artificial knee joint 800, for example the tibial spacer 820 or the tibial component 830, during normal physiological use of the artificial knee joint 800. A plurality of fluid deflecting structures 852 are positioned adjacent to the periphery of the non-contact surface 862 of the femoral component 810.

The artificial knee joint 800 shown in FIG. 8 also includes a tibial component 830 with a bone-facing surface attached to the tibia 823 in vivo to form a bone-prosthesis interface 827. The tibial component 830 is attached to a tibial spacer 820. In the embodiment illustrated in FIG. 8, the tibial spacer 820 includes a non-contact surface 864. The non-contact surface 864 is a surface of the tibial spacer 820 that is predicted to not come into contact with other components of the artificial knee joint 800, for example the femoral component 810, during normal physiological use of the artificial knee joint 800. A plurality of fluid deflecting structures 854 are positioned relative to the periphery of the non-contact surface 864 of the tibial spacer 820. Although not shown in FIG. 8, some embodiments include one or more fluid deflecting structures positioned relative to the periphery of a non-contact surface of the tibial component 830.

A plurality of fluid deflecting structures 854 are attached to the periphery of the non-contact surface 864 of the tibial spacer 820. Although not shown in FIG. 8, some embodiments include one or more fluid deflecting structures attached to a non-contact surface of the tibial component 830. A plurality of fluid deflecting structures 852 are attached to the periphery of the non-contact surface 862 of the femoral component 810. A medial particle retaining structure 870 is connected at a first end to the femoral component 810 and to the tibial spacer 820 at a second end. A lateral particle retaining structure 880 is connected at a first end to the femoral component 810 and to the tibial spacer 820 at a second end. The particle retaining structures 870, 880 are shown in a cross section view. The fluid deflecting structures 852, 854 are positioned, spaced and shaped to divert the fluid flow within the joint away from the bone-prosthesis interfaces 817, 827. The fluid deflecting structures 852, 854 are positioned, spaced and shaped to divert the fluid flow within the joint away toward the particle retaining structures 870, 880.

As shown in FIG. 8, in some embodiments the fluid deflecting structures 852, 854 can be formed as substantially flat rectangular structures with rounded edges. In some embodiments, the fluid deflecting structures 852 can be formed as flanges or linear structures. The fluid deflecting structures 852, 854 can be attached to the associated components, i.e. the femoral component 810, the tibial spacer 820 and the tibial component 830 with structures suitable for a particular embodiment. For example, the fluid deflecting structures 852, 854 can be attached to the associated components through attachment to bands inserted into corresponding grooves in the components. For example, the fluid deflecting structures 852, 854 can be attached to the associated components through stabilization in cavities in the components (e.g. as shown in FIG. 7). For example, the fluid deflecting structures 852, 854 can be attached to the associated components through adhesive, epoxy or glue. For example, the fluid deflecting structures 852, 854 can be fabricated as part of the components, for example integral to a component fabricated from a plastic material such as polyethylene. The fluid deflecting structures 852, 854 are configured, e.g. in size, shape and position, to operate synergistically to deflect joint fluid toward the particle retaining structures 870, 880 in vivo.

No mechanisms are illustrated in FIG. 8. However, embodiments include those wherein some or all of the fluid deflecting structures 852, 854 have attached mechanisms, the mechanisms configured to position the fluid deflecting structures 852, 854 to deflect joint fluid in vivo in the direction of the particle retaining structures 870, 880. In some embodiments, the mechanisms are attached to the external surface of the non-contact regions and the associated fluid deflecting structures 852, 854. In some embodiments, the mechanisms are positioned within cavities adjacent to the non-contact surfaces 862, 864 (e.g. as illustrated in FIG. 7B). The selection of which portion, or all, of the fluid deflection structures 852, 854 have attached mechanisms operable to move the fluid deflection structure to direct synovial fluid away from the bone-prosthesis interface in vivo and in the direction of the particle retaining structures 870, 880 depends on the embodiment. Factors to consider include the size, shape, and expected physiological joint pressures of the artificial knee joint. Similarly, the type of mechanism selected in a given embodiment as operable to move an attached fluid deflection structure depends on factors such as the size, mass, position and flexibility of the fluid deflection structure, as well as the expected physiological fluid pressures during in vivo use of the joint. Mechanisms attached to the external surface of the non-contact region will operate with different parameters than those situated within a cavity adjacent to the surface. The fluid deflection structures with attached mechanisms will actively divert fluid flow within the joint. Some embodiments include fluid deflection structures without attached mechanisms, the fluid deflection structures without attached mechanisms configured to assist the fluid deflection structures with attached mechanisms to deflect joint fluid away from the prosthesis-bone interface in vivo in the direction of the particle retaining structures.

The size, shape, and position of the fluid deflecting structures 852, 854 are selected relative to the size and shape of the joint, as well as the expected physiological fluid pressures during in vivo use of the joint. The size, shape, and position of the fluid deflecting structures 852, 854 are also selected relative to the requirements of any attached mechanism, for example due to the position or mode of operation of the mechanism. As shown in FIG. 8, in some embodiments the fluid deflecting structures 852, 854 can be formed as substantially flat rectangular structures with rounded edges. In some embodiments, the fluid deflecting structures 852 can be formed as flanges or linear structures.

Some embodiments include fluid deflecting structures that are not attached to a mechanism, but are directly affixed to a component of the artificial knee joint. The fluid deflecting structures 852, 854 can be attached to the associated components, i.e. the femoral component 810, the tibial spacer 820 and the tibial component 830 with structures suitable for a particular embodiment. For example, the fluid deflecting structures 852, 854 can be attached to the associated components through attachment to bands inserted into corresponding grooves in the components. For example, the fluid deflecting structures 852, 854 can be attached to the associated components through stabilization in cavities in the components (e.g. as shown in FIG. 7) with or without an associated mechanism to drive the motion of the fluid deflection structure. For example, the fluid deflecting structures 852, 854 can be attached to the associated components through adhesive, epoxy or glue. For example, the fluid deflecting structures 852, 854 can be fabricated as part of the components, for example integral to a component fabricated from a plastic material such as polyethylene.

As FIG. 8 illustrates, in some embodiments an artificial knee joint 800 prosthesis includes: a bone-facing surface of a knee joint prosthesis, the bone-facing surface configured to face a bone-prosthesis interface 817, 827 in vivo; a non-contact surface 862, 864 of the knee joint prosthesis, the non-contact surface 862, 864 adjacent to the bone-facing surface of the knee joint prosthesis; at least one fluid deflection structure 852, 854 positioned on the non-contact surface 862, 864, the fluid deflection structure 852, 854 positioned to deflect synovial fluid away from the bone-prosthesis interface 817, 827 in vivo; a mechanism attached to the fluid deflection structure, the mechanism operable to move the fluid deflection structure to direct synovial fluid away from the bone-prosthesis interface in vivo; and at least one particle retaining structure 870, 880 positioned to contact the directed flow of synovial fluid and configured to retain non-physiological particles present within the synovial fluid. In some embodiments, the bone-facing surface of the artificial knee joint 800 prosthesis includes one or more of: a bone-facing surface of a tibial spacer component of the knee joint prosthesis, a bone-facing surface of a tibial component of the knee joint prosthesis, a bone-facing surface of a femoral component of the knee joint prosthesis, or a bone-facing surface of a patellar component of the knee joint prosthesis. In some embodiments, the non-contact surface 862, 864 of the knee joint prosthesis includes one or more of: a edge region 864 of a liner of a tibial spacer component 820 of the knee joint prosthesis; a edge region 862 of a tibial component 830 of the knee joint prosthesis; and a edge region of a patellar component of the knee joint prosthesis.

A fluid deflection structure associated with the non-contact surface of an artificial knee joint can be configured in different shapes, as appropriate for the fluid deflection parameters of a specific embodiment. Some embodiments include at least one fluid deflection structure positioned adjacent to the non-contact surface including at least one flange structure positioned to extend from the non-contact surface. In some embodiments, the at least one flange structure is positioned to extend from the non-contact surface at an angle varying substantially between 10 degrees and 80 degrees of a plane established by the contact surface and relative to the bone-facing surface of the knee joint prosthesis. In some embodiments, the at least one flange structure is positioned to extend from the non-contact surface at an angle varying substantially between 100 degrees and 170 degrees of a plane established by the contact surface and relative to the bone-facing surface of the knee joint prosthesis. Some embodiments include at least one flange structure with a first end positioned adjacent to the non-contact surface and a second end distal to the non-contact surface, wherein the flange structure is widest at the first end and narrowest at the second end. Some embodiments include at least one flange structure with a first end positioned adjacent to the non-contact surface and a second end distal to the non-contact surface, wherein the flange structure tapers from a widest point at the first end to a narrow point at the second end. Some embodiments include at least one flange structure with a curvilinear structure. Some embodiments include a plurality of flange structures.

In some embodiments, one or more of the fluid deflection structures associated with a knee joint prosthesis include linear projections. Some embodiments include a plurality of linear projections. In some embodiments, the plurality of linear projections are positioned to extend from the non-contact surface at an angle varying substantially between 10 degrees and 80 degrees of a plane established by the contact surface and relative to the bone-facing surface of the knee joint prosthesis. In some embodiments, the plurality of linear projections are positioned to extend from the non-contact surface at an angle varying substantially between 100 degrees and 170 degrees of a plane established by the contact surface and relative to the bone-facing surface of the knee joint prosthesis.

Some embodiments include one or more fluid deflection structures configured as substantially straight fluid deflection structures. For example, a substantially straight fluid deflection structure can be configured as a flat, substantially rectangular plane. Some embodiments include one or more fluid deflection structures configured as substantially curved fluid deflection structures. For example, a substantially curved fluid deflection structure can be a curvilinear or "crescent" shaped structure.

In some embodiments, at least one fluid deflection structure positioned adjacent to the non-contact surface is configured to be substantially rigid at physiological conditions when the artificial joint is utilized in vivo. For example, the fluid deflection structure can be fabricated from a plastic material expected to be substantially rigid at physiological temperatures and joint fluid pressures. In some embodiments, at least one fluid deflection structure positioned adjacent to the non-contact surface is configured to be flexible at physiological conditions when the artificial joint is utilized in vivo. For example, the fluid deflection structure can be fabricated from a plastic material expected to be substantially flexible at physiological temperatures and joint fluid pressures. Fluid deflection structures can be fabricated, for example, from plastic or metal components as suitable for implantation and use in vivo.

The selection of the size and shape of the fluid deflection structures utilized in a specific embodiment is particular to the expected parameters of that embodiment. For example, in some embodiments the at least one fluid deflection structure positioned adjacent to the non-contact surface is configured to flex to a degree sufficient to permit a larger synovial fluid flow rate away from the bone-prosthesis interface during periods of increased synovial fluid pressure in the region of the non-contact surface when the artificial joint is utilized in vivo at physiological conditions, and to permit a smaller synovial fluid flow rate away from the bone-prosthesis interface during periods of reduced synovial fluid pressure when the artificial joint is utilized in vivo at physiological conditions. For example, in some embodiments the at least one fluid deflection structure positioned adjacent to the non-contact surface is configured to flex to a degree sufficient to permit an increased synovial fluid flow rate away from the bone-prosthesis interface in response to increased fluid pressure in a region adjacent to the bone-prosthesis interface.

The mechanism attached to a fluid deflection structure will similarly vary depending on the specific embodiment. Factors to consider in the selection of a mechanism include the size, shape, durability, mass, cost and force operable on an attached fluid deflection structure. Some mechanisms attached to a fluid deflection structure are configured to be attached to a non-contact surface of an artificial knee joint prosthesis component. Some mechanisms attached to a fluid deflection structure are configured to be substantially enclosed within the artificial knee joint prosthesis. For example, the mechanism and attached fluid deflection structure can be positioned adjacent to the non-contact surface of the knee prosthesis, such as with epoxy, glue, or other adhesives. For example, the mechanism with the attached fluid deflection structure can be configured to mate with a corresponding surface on the non-contact region of the knee prosthesis. In some embodiments, the mechanism attached to the fluid deflection structure is substantially enclosed within the artificial knee joint prosthesis. For example, the mechanism attached to the fluid deflection structure can be substantially enclosed within a cavity or groove in the non-contact region of the knee joint prosthesis. For example, the mechanism attached to the fluid deflection structure can be substantially enclosed within an extension of the knee joint prosthesis configured to attach the mechanism. The mechanism can be a micromachine, for example one in the size range of 100 nanometers (nm) to 100 micrometers (µm) in diameter. The mechanism can be a MEMS device, for example with a size range of 20 µm to 1 millimeter (mm) in diameter.

The mechanism attached to the fluid deflection structure and operable to move the fluid deflection structure to direct synovial fluid away from the bone-knee joint prosthesis interface and towards a particle retaining structure in vivo can be of a variety of types, depending on the embodiment. Factors to be used in the selection of a mechanism include: the force on the fluid deflection structure desired to deflect the fluid; the size, shape and flexibility of the fluid deflection structures; the size of the mechanism; the cost of the mechanism; and the expected duration of use of the artificial knee joint prosthesis in vivo. The size, shape and distance between a particle retaining structure and the fluid deflection structure is also a factor in mechanism choice. In some embodiments, the mechanism attached to the fluid deflection structure includes an actuator attached to the fluid deflection structure and configured to move the fluid deflection structure. For example, an actuator can include a hydraulic piston, which can be positioned within a cavity formed in the knee prosthesis. In embodiments wherein the mechanism attached to the fluid deflection structure includes an actuator with a hydraulic piston, force from fluid flow against the fluid deflection structure can be transmitted to the piston, with a resulting reverse force transmitted back to the fluid deflection structure to drive movement of the fluid deflection structure. Some embodiments include a battery configured to provide energy to the actuator. For example, the actuator can include an electric motor which is connected to an attached battery.

In some embodiments, the mechanism attached to the fluid deflection structure includes piezoelectric material, the piezoelectric material configured to drive movement of the at least one fluid deflection structure. For example, in some embodiments a piezoelectric material attached to a fluid deflection structure can be configured to generate electrical charge from the pressure force on the fluid deflection structure, and then store the electrical charge in an attached battery. The stored charge in the battery can then be utilized to drive the same fluid deflection structure, or a second fluid deflection structure, with an attached electric motor. Instead or in addition, the stored charge in the battery can be utilized to drive the same fluid deflection structure through re-introduction of the electrical charge to the piezoelectric material, with the resulting reverse piezoelectric effect resulting in pressure force on the fluid deflection structure due to the expansion of the piezoelectric material.

In some embodiments, the mechanism attached to the fluid deflection structure and operable to move the fluid deflection structure to direct synovial fluid away from the bone-knee joint prosthesis interface in vivo includes at least one magnetic actuator, the magnetic actuator configured to drive movement of the at least one fluid deflection structure.

Some embodiments include: an aperture in the non-contact surface of the artificial knee joint prosthesis; a substantially round cavity in the artificial knee joint prosthesis adjacent to the aperture; the mechanism including a substantially round element of a size and shape to correspond to the substantially round cavity, the substantially round element positioned within the substantially round cavity and configured to move within the substantially round cavity; and the at least one fluid deflection structure attached to the substantially round element and projecting through the aperture. For example, the mechanism can be configured with a substantially round external shape, of a size and shape to reversibly mate with the internal surface of the substantially round cavity in the artificial knee joint prosthesis. A mechanism with a substantially round external shape within a substantially round cavity can rotate in the cavity, with the resulting movement of a fluid deflection structure attached to the mechanism and projecting through an aperture between the cavity and the external surface of the knee prosthesis. The mechanism can utilize the force transmitted by the joint fluid through the fluid deflection structure, such as through the operation of a piezoelectric material or hydraulic piston, to drive further movement of the attached fluid deflection structure. The mechanism can be configured as a ball-like structure to rotate within the cavity in multiple directions. The mechanism can be configured as a cylindrical structure, with a corresponding cylindrical cavity, to rotate specifically along the axis formed by the radius of the cylindrical structure.

Some embodiments of an artificial knee joint prosthesis include: at least one first magnet attached to the artificial knee joint prosthesis; and at least one second magnet attached to the fluid deflection structure, wherein the mechanism attached to the fluid deflection structure is configured to move in accord with a magnetic field established by the at least one first magnet. Some embodiments of an artificial joint prosthesis include: at least one first magnet attached to the artificial knee joint prosthesis; and at least one second magnet attached to the fluid deflection structure, wherein the mechanism attached to the fluid deflection structure is configured to allow the at least one second magnet to move the fluid deflection structure in accord with a magnetic field established by the at least one first magnet. The magnets can be configured as a mechanism attached to the fluid deflection structure, the mechanism operable to move the fluid deflection structure to direct synovial fluid away from the bone-knee joint prosthesis interface in vivo. The magnets can be configured to assist a mechanism attached to the fluid deflection structure, the mechanism operable to move the fluid deflection structure.

Some embodiments of an artificial knee joint prosthesis include at least two components, each of which include at least one fluid deflection structure, and each of which include the mechanism attached to the fluid deflection structure, each of the mechanisms operable to move each of the fluid deflection structures to direct synovial fluid away from the bone-knee joint prosthesis interface in vivo. For example, an artificial knee prosthesis can include a femoral component and a tibial component, each of which include at least one fluid deflection structure with an attached mechanism, each of the mechanisms operable to move each of the fluid deflection structures to direct synovial fluid away from the bone-prosthesis interface in vivo during physiological use of the artificial knee joint. Some embodiments of an artificial knee joint prosthesis include: at least one femoral component, wherein the femoral component includes at least one fluid deflection structure positioned adjacent to the non-contact surface and at least one mechanism attached to the at least one fluid deflection structure; and at least one tibial component, wherein the tibial component includes at least one fluid deflection structure positioned adjacent to the non-contact surface and at least one mechanism attached to the at least one fluid deflection structure.

Figure 9:
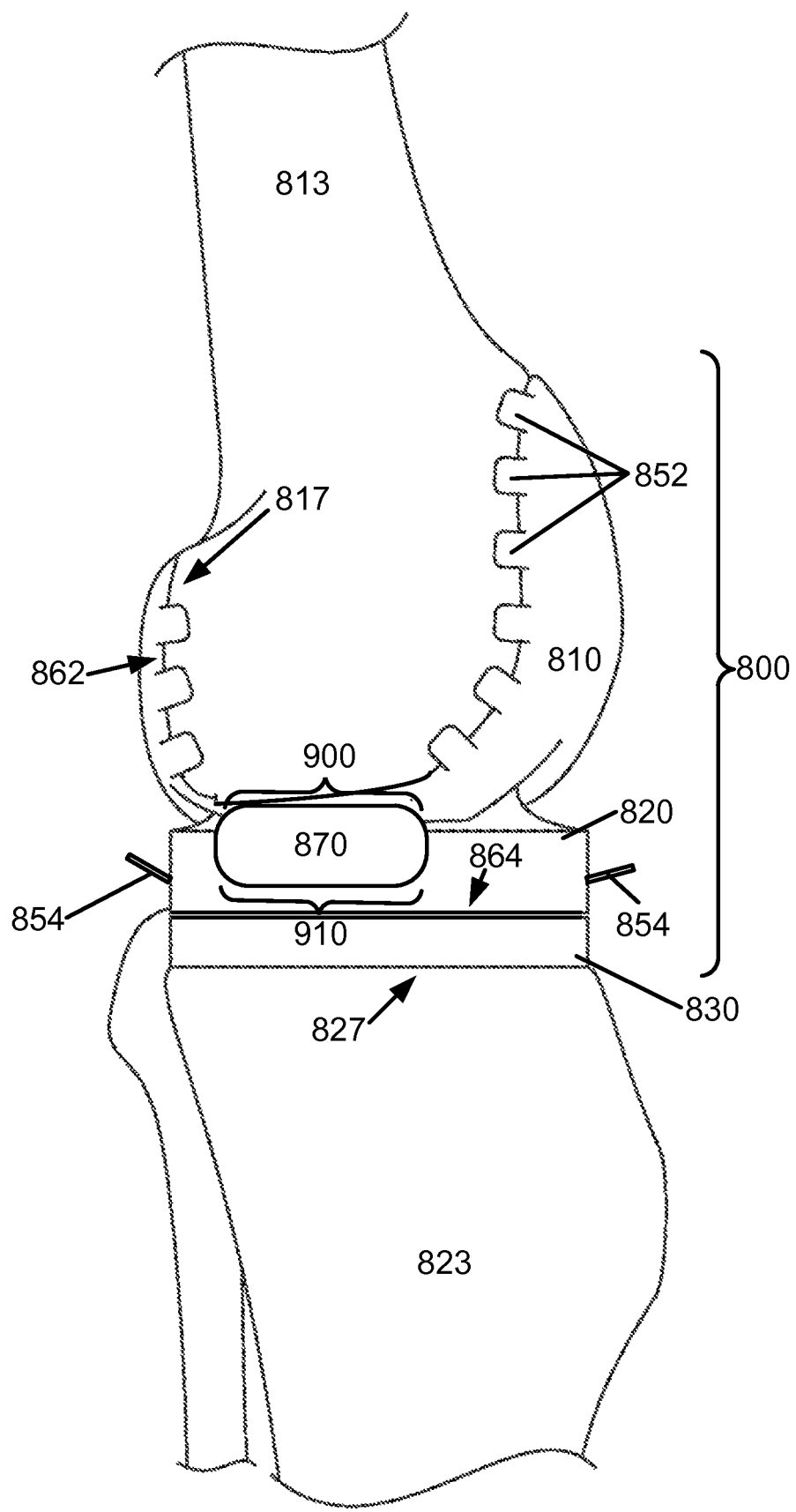
FIG. 9 shows a side view of an artificial knee joint as in FIG. 8.

FIG. 9 shows a view of an embodiment similar to that shown in FIG. 8, from a side-facing view relative to the individual. The embodiment illustrated in FIG. 9 is shown in a side view, with the surrounding skin, ligaments and tissues removed for clarity of presentation. The artificial knee joint 800 shown in FIG. 9 includes artificial joint components 830, 810 attached to both the femur 813 and the tibia 823. A patella is not depicted, although some embodiments include an artificial patella that is part of the artificial knee joint 800.

As shown in FIG. 9, the femur 813 has an attached femoral component 810. The femoral component 810 includes a region with a non-contact surface 862. Associated with the non-contact surface 862 of the femoral component 810 are a series of fluid deflecting structures 852. The fluid deflecting structures 852 are configured to reduce synovial fluid flow at the bone-implant interface 817 in vivo. The fluid deflecting structures 852 are configured to reduce synovial fluid pressure at the bone-implant interface 817 in vivo during physiological use of the knee joint. Although not illustrated in FIG. 9, some or all of the fluid deflecting structures 852 are attached to a mechanism operable to move the fluid deflection structure to direct synovial fluid away from the bone-prosthesis interface in vivo. Depending on the embodiment, some of the fluid deflecting structures 852 can be attached directly to the non-contact surface 862 without attached mechanisms.

FIG. 9 also shows that a tibial component 830 and a tibial spacer 820 of the artificial knee joint 800 are attached to the tibia 823. The tibial component 830 has a bone-facing surface configured to form a bone-implant interface 827 in vivo. The tibial spacer 820 includes a region with a non-contact surface 864. Attached to the non-contact surface 864 of the tibial spacer 820 are a series of fluid deflecting structures 854. The fluid deflecting structures 854 are configured to reduce synovial fluid flow at the bone-implant interface 827 in vivo. The fluid deflecting structures 854 are configured to reduce synovial fluid pressure at the bone-implant interface 827 in vivo and deflect fluid flow to the particle retaining structures 870 during physiological use of the knee joint. Although not illustrated in FIG. 9, some or all of the fluid deflecting structures 854 are attached to a mechanism operable to move the fluid deflection structure to direct synovial fluid away from the bone-prosthesis interface in vivo. Depending on the embodiment, some of the fluid deflecting structures 854 can be attached directly to the non-contact surface 864 without attached mechanisms.

The exact placement, size, shape and positioning of the fluid deflecting structures 852, 854 attached to an artificial knee joint 800 prosthesis will vary depending on the embodiment. For example, the size, shape, positioning, placement and fabrication of the fluid deflecting structures 852, 854 will vary depending on the expected synovial fluid flow during physiological movement in vivo and the size and shape of the artificial knee joint 800. The particular fluid deflecting structures 852, 854 for an embodiment will be configured to mitigate synovial fluid flow rates at the bone-implant interfaces 817, 827 in vivo, including with their attached mechanisms operable to move the fluid deflection structure to direct synovial fluid away from the bone-prosthesis interface in vivo and deflect fluid flow to the particle retaining structures 870. The particular fluid deflecting structures 852, 854 for an embodiment and any attached mechanisms will be configured to reduce transient synovial fluid pressure at the bone-implant interfaces 817, 827 during physiological use in vivo and deflect fluid flow to the particle retaining structures 870.

As shown in situ in FIGS. 8 and 9, a knee joint prosthesis includes: at least one bone-facing surface of a knee joint prosthesis, the bone-facing surface configured to face a bone-prosthesis interface 817, 827 in vivo; a non-contact surface 862, 864 of the knee joint prosthesis, the non-contact surface 862, 864 adjacent to the bone-facing surface 817, 827 of the knee joint prosthesis; at least one fluid deflection structure 852, 854 positioned on the non-contact surface 862, 864, the fluid deflection structure 852, 854 positioned to deflect synovial fluid away from the bone-prosthesis interface 817, 827 in vivo; a mechanism operable to move the fluid deflection structure to direct synovial fluid away from the bone-prosthesis interface in vivo; and at least one particle retaining structure 870, 880 positioned to contact the directed flow of synovial fluid and configured to retain non-physiological particles present within the synovial fluid. In some embodiments, the bone-facing surface of the knee joint prosthesis includes a bone-facing surface of a tibial spacer 820 component of the knee joint prosthesis. In some embodiments, the bone-facing surface of the knee joint prosthesis includes a bone-facing surface of a tibial component 830 of the knee joint prosthesis. In some embodiments, the bone-facing surface of the knee joint prosthesis includes bone-facing surface of a femoral component 810 of the knee joint prosthesis. In some embodiments, the bone-facing surface of the knee joint prosthesis includes bone-facing surface of a patellar component of the knee joint prosthesis.

As shown in FIG. 9, in some embodiments at least one particle retaining structure 870 is configured as a substantially planar structure. The particle retaining structure 870 shown in FIG. 9 is configured as a planar structure that is attached to the femoral component 810 along one edge 900 and attached to the tibial spacer 820 along a second edge 910. In some embodiments, at least one particle retaining structure 870 includes a mesh-like structure. For example, a mesh-like structure can include apertures of an appropriate size range to sequester particles from the fluid flow (e.g. apertures in the 0.05 to 0.01 mm range). In some embodiments, at least one particle retaining structure 870 includes a filter structure. In some embodiments, at least one particle retaining structure 870 includes a foam structure. For example, a particle retaining structure 870 such as that illustrated in FIG. 9 can be fabricated from a substantially planar foam structure.

Some embodiments include at least one particle retaining structure configured as a group of projections, each of the projections positioned to contact the flow of synovial fluid and configured to retain particles present within the synovial fluid. For example, the projections can be configured with a size, shape, flexibility and positioning to contact the flow of synovial fluid. The projections can also include a surface coating configured to retain particulate structures from the fluid flow, for example a surface coating including antibodies configured to bind proteins on the surface of the particles. In some embodiments, at least one particle retaining structure includes a hydrophobic surface. In some embodiments, at least one particle retaining structure includes a structure configured to retain non-physiological particles present in the synovial fluid, for example a chemical configured to bind to non-physiological materials (e.g. plastic or ceramic). In some embodiments, at least one particle retaining structure includes a structure configured to retain particles including artificial materials, for example a magnet configured to bind ferromagnetic particles.

Figure 10:
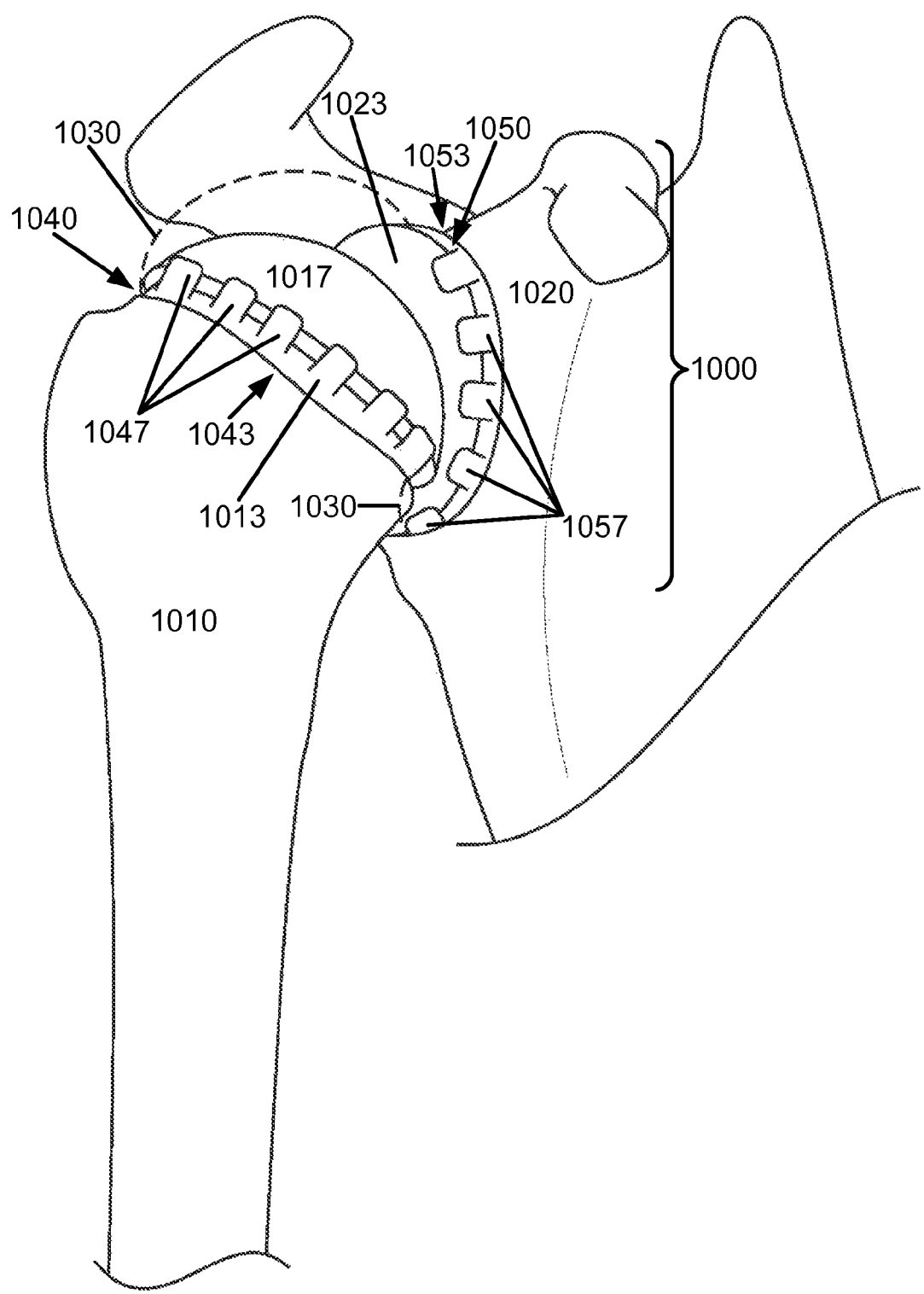
FIG. 10 illustrates an artificial shoulder joint.

FIG. 10 illustrates a shoulder joint prosthesis 1000 in vivo, including a humerus bone 1010 with an attached humerus spacer 1013 and humerus cap 1017 of the prosthesis. There is a humerus bone-prosthesis interface 1043 between the humerus bone 1010 and the humerus spacer 1013. The shoulder joint prosthesis 1000 shown in FIG. 10 also includes a glenoid component 1023 attached to a glenoid cavity 1020 of the scapula bone. A particle retaining structure 1030 is configured as a sheath surrounding the shoulder joint. The embodiment illustrated in FIG. 10 is a conventional shoulder joint prosthesis, however some embodiments include a shoulder joint prosthesis that is a reverse shoulder joint prosthesis.

Some embodiments include a shoulder joint prosthesis including: a bone-facing surface of a shoulder joint prosthesis, the bone-facing surface configured to face a bone-prosthesis interface in vivo; a non-contact surface of the shoulder joint prosthesis, the non-contact surface adjacent to the bone-facing surface of the shoulder joint prosthesis; at least one fluid deflection structure positioned adjacent to the non-contact surface, the fluid deflection structure positioned to deflect synovial fluid away from the bone-prosthesis interface in vivo; a mechanism attached to the fluid deflection structure, the mechanism operable to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

For example, FIG. 10 illustrates a shoulder joint prosthesis 1000 in vivo, including a humerus bone 1010 with an attached humerus spacer 1013 and humerus cap 1017 of the prosthesis. There is a humerus bone-prosthesis interface 1043 between the humerus bone 1010 and the humerus spacer 1013. The shoulder joint prosthesis 1000 shown in FIG. 10 also includes a glenoid component 1023 attached to a glenoid cavity 1020 of the scapula bone. A synovial membrane 1030 is illustrated to roughly define the area within the joint that will contain synovial fluid in vivo. The embodiment illustrated in FIG. 10 is a conventional shoulder joint prosthesis, however some embodiments include a shoulder joint prosthesis that is a reverse shoulder joint prosthesis.

Each of the individual components of the shoulder joint prosthesis 1000 shown in FIG. 10 includes a bone-facing surface. The bone-facing surfaces of the components are not visible in FIG. 10 as the shoulder joint prosthesis 1000 is illustrated in vivo, with the bone-facing surfaces obscured by the bone-prosthesis interfaces and the prosthesis-prosthesis interfaces. There is a scapula bone-prosthesis interface 1053 between the glenoid component 1023 of the prosthesis and the glenoid cavity 1020 of the scapula bone, with the region of the glenoid component 1023 facing the glenoid cavity 1020 of the scapula bone forming a bone-facing surface. There is a bone-prosthesis interface 1043 between the humerus 1010 and the humerus spacer 1013, with the region of the humerus spacer 1013 facing the humerus 1010 forming a bone-facing surface. There is a prosthesis-prosthesis interface between the humerus cap 1017 and the humerus spacer 1013, with a region of the humerus cap 1017 forming a bone-facing surface. The bone-facing surface of the humerus cap 1017 does not contact the bone, however it faces the humerus 1010 and thus forms a bone-facing surface. In some embodiments, the bone-facing surface of the shoulder joint prosthesis includes a bone-facing surface of a liner of a glenoid component of the shoulder joint prosthesis. In some embodiments, the bone-facing surface of the shoulder joint prosthesis includes a bone-facing surface of a glenoid fixation component of the shoulder joint prosthesis. In some embodiments, the bone-facing surface of the shoulder joint prosthesis includes a bone-facing surface of a humeral head component of the shoulder joint prosthesis. In some embodiments, the bone-facing surface of the shoulder joint prosthesis includes a bone-facing surface of a stem of a humeral component of the shoulder joint prosthesis.

A non-contact surface 1040, 1050 of a shoulder joint prosthesis 1000 is a surface of a region of the shoulder joint prosthesis 1000 that is predicted to not come into contact with another component of the shoulder joint during normal physiological movement of the joint. As shown in FIG. 10, the humerus spacer 1013 has a non-contact surface 1040 around the edge surrounding the bone-prosthesis interface 1043. Some embodiments of a shoulder joint prosthesis include a non-contact surface that is a edge region of a humeral head component of the shoulder joint prosthesis. Some embodiments of a shoulder joint prosthesis include a non-contact surface that is a edge region of a stem of a humeral component of the shoulder joint prosthesis. The glenoid component 1023 also has a non-contact surface 1050 surrounding the edge of the glenoid component 1023 adjacent to the scapula bone-prosthesis interface 1053. Some embodiments of a shoulder joint prosthesis include a non-contact surface that is a edge region of a glenoid component of the shoulder joint prosthesis. Some embodiments of a shoulder joint prosthesis include a non-contact surface that is a edge region of a glenoid fixation component of the shoulder joint prosthesis.

The shoulder joint prosthesis 1000 shown in FIG. 10 includes a plurality of fluid deflecting structures 1047 associated with the non-contact surface 1040 of the humerus spacer 1013. The shoulder joint prosthesis 1000 shown in FIG. 10 also includes a plurality of fluid deflecting structures 1057 associated with the non-contact surface 1050 surrounding the edge of the glenoid component 1023. A fluid deflection structure 1047, 1057 of a shoulder joint prosthesis 1000 is a structure associated with a non-contact surface 1040, 1050 and configured to mitigate fluid flow and reduce transient fluid pressure at a bone-prosthesis interface 1043, 1053 during physiological use of the shoulder joint in vivo. A fluid deflecting structure can be positioned adjacent to a non-contact surface of a shoulder joint prosthesis by a variety of means, depending on the embodiment. For example, a fluid deflecting structure can be attached to a mechanism, the mechanism attached to the non-contact surface. For example, a fluid deflecting structure can include an end region configured to stabilize the fluid deflecting structure within a cavity in a prosthesis component, with an attached mechanism within the cavity (see, e.g. FIG. 7). For example, a passive, or non-actuated, fluid deflecting structure without an attached mechanism can be attached to a non-contact surface directly. For example, a fluid deflecting structure can be attached to a non-contact surface of a shoulder joint prosthesis by glue, adhesive or epoxy. For example, a fluid deflecting structure can be attached to a band, which is then stabilized in a groove in a non-contact surface of a shoulder joint.

In some embodiments, the at least one fluid deflection structure positioned on the non-contact surface includes at least one flange structure positioned to extend from the non-contact surface. For example, in some embodiments the at least one flange structure is positioned to extend from the non-contact surface at an angle substantially between 10 degrees and 80 degrees of a plane established by the contact surface and relative to the bone-facing surface of the shoulder joint prosthesis. Some embodiments include at least one flange structure positioned to extend from the non-contact surface at an angle substantially between 100 degrees and 170 degrees of a plane established by the contact surface and relative to the bone-facing surface of the shoulder joint prosthesis. Some embodiments include at least one flange structure positioned to extend from the non-contact surface at a substantially right angle from a plane established by the contact surface and relative to the bone-facing surface of the shoulder joint prosthesis. A flange structure can include at least one flange structure with a first end adjacent to the non-contact surface and a second end distal to the non-contact surface, wherein the flange structure is widest at the first end and narrowest at the second end. A flange structure can include at least one flange structure with a first end positioned adjacent to the non-contact surface and a second end distal to the non-contact surface, wherein the flange structure tapers from a widest point at the first end to a narrow point at the second end. A flange structure can include at least one flange structure with a curvilinear structure. A flange structure can include at least one flange structure with a substantially straight structure.

As shown in FIG. 10, in some embodiments a shoulder joint prosthesis 1000 includes at least one fluid deflection structure with a first end associated with the non-contact surface and a second end distal to the non-contact surface. Also as shown in FIG. 10, some embodiments include a plurality of fluid deflection structures associated with one or more non-contact surfaces. For example, some embodiments include at least one scapular component, wherein the scapular component includes at least one fluid deflection structure positioned on the non-contact surface, and at least one humeral component, wherein the humeral component includes at least one fluid deflection structure positioned on the non-contact surface. Some embodiments include a single fluid deflection structure, for example a fluid deflection structure encircling the edge of a non-contact surface.

In some embodiments, a shoulder joint prosthesis 1000 includes at least one fluid deflection structure including a plurality of linear projections. For example, the plurality of linear projections can be shaped as rods or cilia, for example as hair-like projections. See, e.g. FIG. 5. Fluid deflection structures configured as linear projections can be positioned to extend from the non-contact surface at an angle substantially between 10 degrees and 80 degrees of a plane established by the contact surface and relative to the bone-facing surface of the shoulder joint prosthesis. Fluid deflection structures configured as linear projections can be positioned to extend from the non-contact surface at an angle substantially between 100 degrees and 170 degrees of a plane established by the contact surface and relative to the bone-facing surface of the shoulder joint prosthesis. Fluid deflection structures configured as linear projections can be positioned to extend from the non-contact surface at an substantially right angle from a plane established by the contact surface and relative to the bone-facing surface of the shoulder joint prosthesis.

Depending on the embodiment, a fluid deflection structure associated with a non-contact surface of a shoulder joint prosthesis can be configured in a variety of forms to mitigate synovial fluid flow and pressure at the bone-prosthesis interface. The specific size, shape and configuration of a fluid deflection structure depends on the embodiment, including the size, shape, and expected physiological stresses on a shoulder joint during routine use. Some embodiments include at least one fluid deflection structure positioned on the non-contact surface wherein the at least one fluid deflection structure is configured as a substantially straight fluid deflection structure. Some embodiments include at least one fluid deflection structure positioned on the non-contact surface wherein the at least one fluid deflection structure is configured as a substantially curved fluid deflection structure. In some embodiments, at least one fluid deflection structure positioned on a non-contact surface of an artificial shoulder joint prosthesis is configured to be flexible at physiological conditions when the artificial joint is utilized in vivo. In some embodiments, at least one fluid deflection structure positioned on a non-contact surface of an artificial shoulder joint prosthesis is configured to flex to a degree sufficient to permit a larger synovial fluid flow rate away from the bone-prosthesis interface during periods of increased synovial fluid pressure in the region of the non-contact surface when the artificial joint is utilized in vivo at physiological conditions, and to permit a smaller synovial fluid flow rate away from the bone-prosthesis interface during periods of reduced synovial fluid pressure when the artificial joint is utilized in vivo at physiological conditions. In some embodiments, at least one fluid deflection structure positioned on a non-contact surface of an artificial shoulder joint is configured to flex to a degree sufficient to permit an increased synovial fluid flow rate away from the bone-prosthesis interface in response to increased fluid pressure in a region adjacent to the bone-prosthesis interface.

The mechanism attached to a fluid deflection structure of a shoulder joint prosthesis will similarly vary depending on the specific embodiment. Factors to consider in the selection of a mechanism include the size, shape, durability, mass, cost and force operable on an attached fluid deflection structure. Some embodiments include fluid deflection structures without attached mechanisms, and in those embodiments the mechanisms that are attached to fluid deflection structures should be forceful enough to move the attached fluid deflection structures and divert synovial fluid flow through the shoulder joint in combination with the fluid deflection structures without attached mechanisms. Some mechanisms attached to a fluid deflection structure are configured to be attached to a non-contact surface of an artificial shoulder joint prosthesis component. Some mechanisms attached to a fluid deflection structure are configured to be substantially enclosed within the artificial shoulder joint prosthesis. For example, the mechanism and attached fluid deflection structure can be positioned adjacent to the non-contact surface of the shoulder prosthesis, such as with epoxy, glue, or other adhesives. For example, the mechanism with the attached fluid deflection structure can be configured to mate with a corresponding surface on the non-contact region of the shoulder prosthesis. In some embodiments, the mechanism attached to the fluid deflection structure is substantially enclosed within the artificial shoulder joint prosthesis. For example, the mechanism attached to the fluid deflection structure can be substantially enclosed within a cavity or groove in the non-contact region of the shoulder joint prosthesis. For example, the mechanism attached to the fluid deflection structure can be substantially enclosed within an extension of the shoulder joint prosthesis configured to attach the mechanism. The mechanism can be a micromachine, for example one in the size range of 100 nanometers (nm) to 100 micrometers (µm) in diameter. The mechanism can be a MEMS device, for example with a size range of 20 µm to 1 millimeter (mm) in diameter.

A mechanism attached to a fluid deflection structure and operable to move the fluid deflection structure to direct synovial fluid away from the bone-shoulder joint prosthesis interface and toward a particle retaining structure in vivo can be of a variety of types, depending on the embodiment. Factors to be used in the selection of a mechanism include: the force on the fluid deflection structure desired to deflect the fluid; the size, shape and flexibility of the fluid deflection structures; the size of the mechanism; the cost of the mechanism; and the expected duration of use of the artificial shoulder joint prosthesis in vivo. The size, shape and position of the particle retaining structures are also relevant to the selection of mechanism. In some embodiments, the mechanism attached to the fluid deflection structure includes an actuator attached to the fluid deflection structure and configured to move the fluid deflection structure. For example, an actuator can include a hydraulic piston, which can be positioned within a cavity formed in the shoulder prosthesis. In embodiments wherein the mechanism attached to the fluid deflection structure includes an actuator with a hydraulic piston, force from fluid flow against the fluid deflection structure can be transmitted to the piston, with a resulting reverse force transmitted back to the fluid deflection structure to drive movement of the fluid deflection structure. Some embodiments include a battery configured to provide energy to the actuator. For example, the actuator can include an electric motor which is connected to an attached battery.

In some embodiments, the mechanism attached to the fluid deflection structure includes piezoelectric material, the piezoelectric material configured to drive movement of the at least one fluid deflection structure. For example, in some embodiments a piezoelectric material attached to a fluid deflection structure can be configured to generate electrical charge from the pressure force on the fluid deflection structure, and then store the electrical charge in an attached battery. The stored charge in the battery can then be utilized to drive the same fluid deflection structure, or a second fluid deflection structure, with an attached electric motor. Instead or in addition, the stored charge in the battery can be utilized to drive the same fluid deflection structure through re-introduction of the electrical charge to the piezoelectric material, with the resulting reverse piezoelectric effect resulting in pressure force on the fluid deflection structure due to the expansion of the piezoelectric material.

In some embodiments, the mechanism attached to the fluid deflection structure and operable to move the fluid deflection structure to direct synovial fluid away from the bone-shoulder joint prosthesis interface in vivo includes at least one magnetic actuator, the magnetic actuator configured to drive movement of the at least one fluid deflection structure.

Some embodiments include: an aperture in the non-contact surface of the artificial shoulder joint prosthesis; a substantially round cavity in the artificial shoulder joint prosthesis adjacent to the aperture; the mechanism including a substantially round element of a size and shape to correspond to the substantially round cavity, the substantially round element positioned within the substantially round cavity and configured to move within the substantially round cavity; and the at least one fluid deflection structure attached to the substantially round element and projecting through the aperture. For example, the mechanism can be configured with a substantially round external shape, of a size and shape to reversibly mate with the internal surface of the substantially round cavity in the artificial shoulder joint prosthesis. A mechanism with a substantially round external shape within a substantially round cavity can rotate in the cavity, with the resulting movement of a fluid deflection structure attached to the mechanism and projecting through an aperture between the cavity and the external surface of the shoulder prosthesis. The mechanism can utilize the force transmitted by the joint fluid through the fluid deflection structure, such as through the operation of a piezoelectric material or hydraulic piston, to drive further movement of the attached fluid deflection structure. The mechanism can be configured as a ball-like structure to rotate within the cavity in multiple directions. The mechanism can be configured as a cylindrical structure, with a corresponding cylindrical cavity, to rotate specifically along the axis formed by the radius of the cylindrical structure.

Some embodiments of an artificial shoulder joint prosthesis include: at least one first magnet attached to the artificial shoulder joint prosthesis; and at least one second magnet attached to the fluid deflection structure, wherein the mechanism attached to the fluid deflection structure is configured to move in accord with a magnetic field established by the at least one first magnet. Some embodiments of an artificial shoulder joint prosthesis include: at least one first magnet attached to the artificial shoulder joint prosthesis; and at least one second magnet attached to the fluid deflection structure, wherein the mechanism attached to the fluid deflection structure is configured to allow the at least one second magnet to move the fluid deflection structure in accord with a magnetic field established by the at least one first magnet. The magnets can be configured as a mechanism attached to the fluid deflection structure, the mechanism operable to move the fluid deflection structure to direct synovial fluid away from the bone-shoulder joint prosthesis interface in vivo. The magnets can be configured to assist a mechanism attached to the fluid deflection structure, the mechanism operable to move the fluid deflection structure.

Some embodiments of an artificial shoulder joint prosthesis include at least two components, each of which include at least one fluid deflection structure, and each of which include the mechanism attached to the fluid deflection structure, each of the mechanisms operable to move each of the fluid deflection structures to direct synovial fluid away from the bone-shoulder joint prosthesis interface in vivo. For example, an artificial shoulder prosthesis can include a glenoid component and a humeral component, each of which include at least one fluid deflection structure with an attached mechanism, each of the mechanisms operable to move each of the fluid deflection structures to direct synovial fluid away from the bone-prosthesis interface in vivo during physiological use of the artificial shoulder joint. Some embodiments of an artificial shoulder joint prosthesis include: at least one glenoid component, wherein the glenoid component includes at least one fluid deflection structure positioned adjacent to the non-contact surface and at least one mechanism attached to the at least one fluid deflection structure; and at least one humeral component, wherein the humeral component includes at least one fluid deflection structure positioned adjacent to the non-contact surface and at least one mechanism attached to the at least one fluid deflection structure. Some embodiments of an artificial shoulder joint prosthesis include: at least one humeral component, wherein the humeral component includes at least one fluid deflection structure adjacent to the non-contact surface and at least one mechanism attached to the at least one fluid deflection structure; and at least one scapular component, wherein the scapular component includes at least one fluid deflection structure adjacent to the non-contact surface and at least one mechanism attached to the at least one fluid deflection structure.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components, devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components. In some instances, one or more components may be similarly referred to herein as "configured to," "configured by," "configurable to," "operable/operative to," "adapted/adaptable," "able to," "conformable/conformed to," etc.

This application may make reference to one or more trademarks, e.g., a word, letter, symbol, or device adopted by one manufacturer or merchant and used to identify and/or distinguish his or her product from those of others. Trademark names used herein are set forth in such language that makes clear their identity, that distinguishes them from common descriptive nouns, that have fixed and definite meanings, or, in many if not all cases, are accompanied by other specific identification using terms not covered by trademark. In addition, trademark names used herein have meanings that are well-known and defined in the literature, or do not refer to products or compounds for which knowledge of one or more trade secrets is required in order to divine their meaning. All trademarks referenced in this application are the property of their respective owners, and the appearance of one or more trademarks in this application does not diminish or otherwise adversely affect the validity of the one or more trademarks. All trademarks, registered or unregistered, that appear in this application are assumed to include a proper trademark symbol, e.g., the circle R or bracketed capitalization (e.g., [trademark name]), even when such trademark symbol does not explicitly appear next to the trademark. To the extent a trademark is used in a descriptive manner to refer to a product or process, that trademark should be interpreted to represent the corresponding product or process as of the date of the filing of this patent application.

EXAMPLES

Example 1

An Artificial Hip Joint Including Fluid Deflector Structures Configured to Divert and Diffuse Synovial Fluid Flow A hip joint prosthesis is fabricated with fluid deflector structures on select non-contact surfaces of the device. The fluid deflector structures are designed to divert joint fluids away from interfaces between the artificial device and the patient's bone, and to reduce the velocity of fluid flow in the artificial joint, thereby reducing the likelihood of aseptic loosening of the prosthetic implant. The fluid deflector structures are also configured to minimally impede joint function and mobility in vivo. The hip joint prosthesis includes a femoral component which includes a head (or ball), a neck attached to the head, and a stem which is configured to be implanted in the medullary canal of the femur. See, e.g. FIG. 1. The hip joint prosthesis also includes an acetabular component which forms a socket. The socket of the acetabular component includes an outer and inner cup, with the outer cup configured to be attached to pelvic bone and the inner cup configured to bear the head of the femoral component. See, e.g. FIGS. 1 and 2.

The neck and stem of the femoral component are made from titanium (see e.g., U.S. Pat. No. 6,761,741, "Prosthetic Joint," to Iesaka and US Patent Application No. 2003/0229398 "Prosthetic Joint," to Iesaka, which are each incorporated herein by reference). The femoral component of the artificial joint is fabricated by processes of investment casting and milling. For example, a solid model comprised of a thermally labile material (e.g., wax) is made by injection molding and then a ceramic shell is created by coating the solid wax model. The ceramic shell is recovered after melting the solid model and used as a mold to cast the femoral component of the prosthesis. See e.g., U.S. Pat. No. 5,665,118, "Bone Prostheses with Direct Cast Macrotextured Surface Regions and Method for Manufacturing the Same," to LaSalle et al., which is incorporated herein by reference.

At the base of the femoral component neck and the top of the femoral component stem, a row of fluid deflector structures (see e.g. FIG. 5) are attached. The fluid deflector structures are positioned and shaped in a manner predicted to deflect synovial fluids away from the interface between the femur and the implanted stem, and to diffuse the fluid pressure at the interface, thus reducing the possibility of periprosthetic bone resorption (see e.g., Fahlgren et al., "Fluid Pressure and Flow as a Cause of Bone Resorption," *Acta Orthopaedica* 81: 508-516, 2010 which is incorporated herein by reference). The fluid deflector structures are fabricated from polyethylene and include a band linking an edge of each of a series of the fluid deflector structures at a set orientation relative to the circumference of the band. The base of the femoral component neck and the top of the femoral component stem are machined to include small surface grooves positioned to stabilize the fluid deflection structures. Each groove corresponds to the size and shape of the band linking a series of the fluid deflector structures (see, e.g. FIG. 6).

Fluid deflector structures are created from polyethylene in suitable shapes and sizes to line the border between the titanium stem and the femur and configured to deflect synovial fluid away from the stem-bone interface in vivo. Compression molding is used to form the polymeric fluid deflector structures directly onto the metallic stem at the site of the groove. See e.g., U.S. Pat. No. 5,879,404, "Acetabular Cups and Methods of their Manufacture," issued to Bateman et al. and U.S. Pat. No. 6,368,354, "Acetabular Bearing Assembly for Total Hip Joints," issued to Burstein, which are each incorporated herein by reference. Fluid deflector structures approximately 1 cm long and 0.5 cm in width are cast to protrude around the circumference of the femoral stem in a configuration predicted to divert synovial fluid away from the bone-stem interface and to reduce the transient synovial fluid pressure during physiological use of the joint. The fluid deflector structures are flexible, but firm enough to remain extended above the surface of the prosthesis and positioned to guide synovial fluid flow away from the stem-bone interface in vivo. See FIGS. 2 and 4. For example, a model hip joint subjected to axial and torsional forces displays high and low pressure in the proximal posterior and proximal anterior areas respectively of the femoral stem (see e.g., Bartlett et al., "In Vitro Influence of Stem Surface Finish and Mantle Conformity on Pressure Generation in Cemented Hip Arthroplasty," *Acta Orthopaedica* 80: 139-143, 2009 which is incorporated herein by reference). Fluid pressure differentials drive high estimated synovial fluid flow rates (e.g., 20 mm/s) and promote osteolysis that is observed in vivo in animal models of bone resorption (see e.g., Fahlgren et al., ibid., which is incorporated herein by reference). Fluid deflector structures are constructed to occlude the interface between the prosthesis stem and femoral bone and to reduce the transient pressure and divert the flow of joint fluid during physiological movement (see FIGS. 2 and 4).

The acetabular component of the artificial joint is constructed using a process of investment casting that employs titanium in the outer cup and titanium and polyethylene in the inner cup (see e.g., U.S. Pat. No. 5,665,118 ibid. which is incorporated herein by reference). During the casing process, fluid deflector structures are constructed from polyethylene and integrally formed at the margin of the outer cup. These fluid deflection structures are fabricated of a size and shape expected to divert synovial fluid away from the interface between the pelvic bone and the outer cup during in vivo use. See, e.g. FIGS. 1-4. Manufacture of acetabular cups with titanium and polyethylene components is described (see e.g., U.S. Pat. No. 5,879,404, ibid. which is incorporated herein by reference).

If desired, a hip joint prosthesis can be surgically implanted that includes both a femoral component with fluid deflection structures attached and an acetabular cup with fluid deflection structures attached, as described above. A medical caregiver can also select a hip joint prosthesis that has fluid deflection structures attached to either the femoral component or the acetabular component. In this situation, the corresponding components without fluid deflection structures can be obtained for implantation in conjunction with the component with fluid deflection structures attached. For example, a femoral component with a titanium stem and a cobalt chromium alloy head is available from Stryker Orthopaedics, Mahwah, N.J. A acetabular component with a titanium shell and polyethylene bearings is available from Stryker Orthopaedics, Mahwah, N.J.

Example 2

An Artificial Knee Joint Including Fluid Deflector Structures and an Encapsulation/Filtration Membrane Configured to Retain Particulates A knee joint prosthesis is fabricated with fluid deflector structures on select non-contact surfaces of the device. The fluid deflector structures are of a size, shape and position expected to divert joint fluids away from the interfaces of the device and the patient's bone, thereby reducing the likelihood of aseptic loosening of the prosthetic implant. The knee joint prosthesis is fabricated including a filter membrane configured to capture debris particles arising in the joint that can be present in the joint fluid. The fluid deflector structures are configured to divert fluid flow through the filter, promoting removal of debris particles from the joint fluid. Polyethylene and metal debris particles in joint fluid, for example, are generally associated with osteolysis and loosening of artificial knee implants (see e.g., Collier et al., "Osteolysis After Total Knee Arthroplasty: Influence of Tibial Baseplate Surface Finish and Sterilization of Polyethylene Insert, Findings at Five to Ten Years Postoperatively," *J. Bone Joint Surg.* 87-A: 2702-2708, 2005 which is incorporated herein by reference).

The knee joint prosthesis comprises a femoral component and a tibial part including a tibial spacer, and a tibial tray component. The tibial spacer is fabricated from polyethylene. See e.g., U.S. Patent Application No. 2005/0055101 to Silheos, "Endoprosthesis of the Knee and/or Other Joints," which is incorporated herein by reference. For example, total knee replacement prostheses are commonly available including polyethylene components. See, e.g., Xie, "A Systematic Review on Performance of the Vanguard® Complete Knee System," Form No. BOI0500.0, REV083111, dated Jun. 30, 2011 and available from Biomet Inc., Warsaw, Ind., which is incorporated by reference. Other components are metallic, preferably fabricated from titanium.

Fluid deflector structures are created from polyethylene and attached to the knee prosthesis at non-contact surfaces of the prosthesis components. The fluid deflector structures are of a size and shape expected to deflect synovial fluid away from the prosthesis-bone interface. Compression molding methods are used to form the polymeric fluid deflector structures directly onto the metallic femoral component and tibial tray component (see e.g., U.S. Pat. No. 5,879,404, ibid. and U.S. Pat. No. 6,368,354, ibid, which are each incorporated by reference herein). Fluid deflector structures approximately 1 cm long and 0.5 cm in width are molded to protrude over the boundary of the femoral component and around the circumference of the tibial tray component. See FIGS. 8 and 9.

At the margin of the femoral component adjacent to the prosthesis-bone interface a row of fluid deflector structures (see FIGS. 8 and 9) fabricated from polyethylene. The fluid deflector structures are configured to deflect synovial fluids away from the interface between the femur and the implanted femoral component, and to reduce the velocity of fluid flow in the joint, thus reducing periprosthetic bone resorption (see e.g., Fahlgren et al., ibid., which is incorporated herein by reference). A row of polyethylene fluid deflector structures is also attached to one or more of the tibial components and configured to divert and impede fluid flows away from the interface between the tibial component and bone (see FIGS. 8 and 9).

The tibial tray component of the artificial joint is constructed using a process of investment casting (see e.g., U.S. Pat. No. 5,665,118 ibid., which is incorporated by reference herein) that employs titanium alloys. Fluid deflector structures constructed from polyethylene are formed on the margin of the tibial tray component to prevent synovial fluid from entering the interface between the tibial tray baseplate and the tibia. See FIGS. 8-9 and Xie, ibid, which is incorporated by reference herein. Manufacture of prostheses with titanium and polyethylene components is as described (see e.g., U.S. Pat. No. 5,879,404, ibid, which is incorporated by reference herein).

The fluid deflector structures are flexible but firm enough to remain extended above the surface of the prosthesis and positioned to guide synovial fluid flow from transient regions of high fluid pressure to transient regions of low fluid pressure. For example, a model joint subjected to physiological axial and torsional forces displays relatively high and low pressure in the proximal posterior and proximal anterior areas respectively of a femoral stem (see e.g., Bartlett et al., 2009, ibid., which is incorporated by reference herein). Fluid pressure differentials result in high estimated fluid flow rates (e.g., 20 mm/s) which are associated with osteolysis and bone resorption (see e.g., Fahlgren et al., ibid., which is incorporated by reference herein). Fluid deflector structures are configured and attached so as to occlude the interface of the femoral component and bone where they divert and diffuse the flow of joint fluid (see FIG. 9). Fluid deflector structures are also of a size, shape and position to direct joint fluid flow toward a filter in the artificial joint. The combination of joint fluid flow diversion away from the bone-implant interface and toward a filter have synergetic effects to reduce the possible occurrence of osteolysis and implant loosening.

To remove debris particles in the joint, a membrane filter is fabricated to surround the artificial knee joint and trap particles present in the synovial joint fluid. Particles can, for example, arise from wear on the polyethylene or metal components of the joint. Particles can, for example, arise from debris remaining after the implantation surgery. Particulate debris arising from the articulating surfaces or elsewhere in the artificial joint are trapped by a membrane surrounding the joint components. The membrane surrounding the joint components is configured to trap debris particles while allowing joint fluid to pass through. A membrane filter comprised of silicone, hydroxyl-ethyl-methacrylate and polyvinylpirrolidone is fabricated to filter and trap particulates which may arise in the artificial joint (see U.S. Patent Application No. 2005/0055101, ibid., which is incorporated by reference herein). A membrane filter is constructed as a tube which attaches at one end to the bone adjacent to the tibial tray-tibia bone interface, while the distal end of the tube attaches to the femoral bone adjacent to the femoral component interface. Membrane filters are composed of laminates of polytetrafluoroethylene (PTFE) of different fibril lengths to trap particles less than 0.2 microns in diameter while allowing fluids to pass. See e.g.: U.S. Pat. No. 6,132,470, "Apparatus and Method for Protecting Prosthetic Joint Assembly from Wear," to Berman; U.S. Pat. No. 5,879,406 "Artificial Joint Bioprosthesis for Mitigation of Wear," to Lilley; U.S. Pat. No. 6,432, 141 "Joint Prosthesis Assembly and Method for Installing Same," to Stocks; US Patent Application No. 2003/0130740 "Joint Prosthesis Assembly and Method for Installing Same," to Stocks; U.S. Pat. No. 7,144,427 "Apparatus and Method for Advancing Synovial Fluid in a Prosthetic Joint," to Southworth; US Patent Application No. 2004/0111162 "Apparatus and Method for Advancing Synovial Fluid in a Prosthetic Joint," to Southworth; US Patent Application No. 2005/0055101 "Endoprosthesis of the Knee and/or other Joints," to Sifneos; and U.S. Pat. No. 5,571,195 "Prosthesis for an Artificial Joint Having Wear Particle Collection Capability," to Johnson, which are each incorporated herein by reference. Methods to attach a membrane filter to the bone adjacent to an artificial joint are described (see e.g.: U.S. Patent Application No. 2005/0055101, ibid.; U.S. Pat. No. 4,731,088, "Enclosure Member for Prosthetic Joint" to Collier; and U.S. Pat. No. 6,132,470, ibid., which are each incorporated by reference herein). The membrane filter can, in some embodiments, include one or more stay rings to minimize the possibility of mechanical entrapment of the membrane filter. See U.S. Pat. No. 5,514,182 "Prosthetic Joint with Semipermeable Capsule with Reinforcing Ribs," to Shea, which is incorporated herein by reference.

Example 3

An Artificial Hip Joint Including Actuated Fluid Deflector Structures Configured to Divert Synovial Fluid and Associated Debris Particles Away from Prosthesis-Bone Interface An artificial hip joint prosthesis is fabricated with actuated fluid deflector structures attached to select non-contact surfaces of the device. The fluid deflector structures are configured to divert joint fluid and associated debris particles away from interfaces between the artificial joint and the patient's bones and to reduce the transient fluid pressure at the interfaces during physiological use of the joint. The fluid deflector structures are attached to mechanisms that move the fluid deflection structures and thereby alter fluid flow in the joint. The altered fluid flow is configured to reduce the likelihood of osteolysis and aseptic loosening of the prosthetic implant.

The hip joint prosthesis includes a femoral component which includes a head (or ball), a neck and a stem which is implanted in the medullary canal of the femur. There is also an acetabular component that includes an outer and inner cup with the outer cup attached to pelvic bone and the inner cup forming a socket bearing the head of the femoral component. The neck and stem of the femoral component are fabricated from titanium (see e.g., U.S. Pat. No. 6,761,741, ibid., which is incorporated herein by reference). Actuated fluid deflector structures are attached to non-contact surfaces on the edge regions of the femoral component and the acetabular component. The fluid deflector structures are configured to deflect synovial fluids and debris particles away from the interfaces between the prosthesis components and bone, and to mitigate the pressure of fluid flow on the prosthesis-bone interfaces, thus reducing the likelihood of periprosthetic bone resorption and artificial joint loosening (see e.g., Fahlgren et al., et al., ibid., which is incorporated herein by reference).

The artificial joint is fabricated using processes of investment casting and milling. For example, a solid model comprised of a thermally labile material (e.g., wax) is made by injection molding and then a ceramic shell is created by coating the solid wax model. The ceramic shell is recovered after melting the solid model and used as a mold to cast the components of the prosthesis. See e.g., U.S. Pat. No. 5,665, ibid., which is incorporated herein by reference. A groove is milled around the circumference of the femoral component at the base of the neck to stabilize attached actuated fluid deflector structures. A groove is also milled around the circumference of the acetabular component in the outer cup to stabilize attached actuated fluid deflector structures.

Actuated fluid deflector structures are constructed from polydimethylsiloxane (PDMS, available from Dow Corning Corp., Midland, Mich.) containing permanently magnetic nanoparticles. Carbon coated iron particles approximately 70 nm in diameter (available from M K Impex Corp., Missisauga, ON, Canada) are dispersed in PDMS and spin cast to obtain fluid deflector structures approximately 1 cm long and 3 mm wide. See e.g., Willem van Engen, Master's Thesis: "Artificial cilia for microfluidics exploring the use of a horizontally microstructured ferromagnetic PDMS composite," Eindhoven University of Technology, 2008, Eindhoven, Netherlands, which is incorporated herein by reference. The fluid deflector structures are magnetized by repeated movement of a permanent magnet with a magnetic field of about 500 mTesla along the long axis of the fluid deflector structures. The fluid deflector structures are attached to a polymeric band by adhesion and the bands, containing approximately 2 fluid deflector structures per centimeter, are inserted in the grooves of the femoral and acetabular components.

Magnetic fluid deflector structures approximately 1 cm long and 3 mm in width are positioned around the circumference of the femoral stem and the acetabular cup in positions predicted to divert synovial fluid away from the bone-stem interface and to mitigate transient high pressure in the joint fluid due to physiological movement of the joint. The fluid deflector structures are flexible but firm enough to remain extended above the surface of the prosthesis and positioned to guide synovial fluid flow. For example, a model hip joint subjected to axial and torsional forces displays high and low pressure in the proximal posterior and proximal anterior areas respectively of the femoral stem (see e.g., Bartlett et al., 2009, ibid., which is incorporated herein by reference). Fluid pressure differentials and high estimated fluid flow rates (e.g., 20 mm/s) promote osteolysis and bone resorption (see e.g., Fahlgren et al., ibid., which is incorporated herein by reference). Magnetic fluid deflector structures are configured to mitigate fluid flow and pressure at the interface of the prosthesis and bone in vivo. The magnetic fluid deflector structures can be fabricated from polyethylene including magnetic nanoparticles. See: Chatterjee et al., "Synthesis of Polyethylene Magnetic Nanoparticles," *European Cells and Materials* 3(2): 98-101 (2002); Wang et al., "Novel Magnetic Polyethylene Nanocomposites Produced by Supported Nanometer Magentic Ziegler-Natta Catalyst," *Polymer International* 49: 184-188 (2000); Millan et al., "Magnetic Polymer Nanocomposites," chapter 17 in Polymer Nanocomposites, Mai and Yu, eds. CRC Press, 2006; and Killeya, "First Plastic Magnets Created," *New Scientist* (30 Aug. 2004), which are each incorporated herein by reference.

A permanent magnet is constructed within the femoral component and configured to actuate the magnetic deflectors. A permanent magnet with a magnetic field of approximately 500 mTesla is placed in the stem region of the femoral component to form a magnetic field configured to interact with the magnetic fluid deflector structures on the femoral and acetabular components as the hip joint moves. The permanent magnet within the femoral component has a size, shape and position expected to create a magnetic field that is roughly perpendicular to the fluid deflector structures. For example, a magnetic field of approximately 50 mTesla applied perpendicular to the magnetic deflectors causes a deflection of approximately 0.5 millimeter in an artificial cilia (see van Engen, ibid., which is incorporated herein by reference).

Alternatively, an electromagnet can be used to actuate the fluid deflector structures. See US Patent Application No. 2008/0306324 "Magnetic Joint Implant," to Bonutti and Beyers, which is incorporated herein by reference. Reversing the direction of electrical current in the electromagnet switches the magnetic field direction by 180 degrees and reverses the direction of movement of the magnetic fluid deflector structures. An electromagnet can be used to create a magnetic field of approximately 500 mTesla, increasing the deflection of the magnetic fluid deflector structures by 10 fold relative to a 50 mTesla magnetic field. Moreover, rapid switching of the direction of the magnetic field will result in "beating" of the magnetic fluid deflector structures to actively divert synovial fluid flow away from prosthesis-bone interfaces. The electromagnet can be empowered by a battery or piezoelectric elements in the artificial hip prosthesis. Piezoelectric devices suitable to capture and store energy from the movement of an artificial joint are known (see e.g., Keawboonchuay et al., "Maximum Power Generation in a Piezoelectric Pulse Generator," *IEEE Transactions On Plasma Science,* 31: 123-128, 2003, which is incorporated herein by reference).

Example 4

An Artificial Hip Joint Including Actuated Fluid Deflector Structures Configured to Capture Debris Particles A hip joint prosthesis is fabricated with actuated fluid deflector structures on select non-contact surfaces of the device. The actuated fluid deflector structures are configured to divert joint fluid and debris particles away from the interface regions between the implanted artificial joint and the patient's bones. Also the actuated fluid deflector structures include distal edge regions with adhesive tips. The adhesive regions of the actuated fluid deflector structures are configured to capture and sequester debris particles in the joint fluid. Debris particles within the joint fluid are associated with an increased likelihood of osteolysis and aseptic loosening of the prosthetic implant.

The hip joint prosthesis includes a femoral component which includes a head (or ball), a neck, and a stem which is configured to be implanted in the medullary canal of the femur. The hip joint prosthesis also includes an acetabular component that includes an outer and inner cup, with the outer cup configured to be attached to pelvic bone and the inner cup forming a socket that bears the head of the femoral component in vivo. The neck and stem of the femoral component are made from titanium (see e.g., U.S. Pat. No. 6,761, 741, ibid., which is incorporated herein by reference).

Actuated fluid deflector structures are formed at the boundaries of the femoral component and the acetabular component. The fluid deflector structures are configured to deflect synovial fluid flow and associated debris particles away from the interfaces between the prosthesis components and bone and to mitigate transient joint fluid pressure on the prosthesis-bone interfaces during physiological use of the joint. The fluid deflector structures are also configured to capture debris particles in the joint fluid, thus reducing the likelihood of periprosthetic bone resorption and artificial joint loosening (see e.g., Fahlgren et al., ibid., which is incorporated herein by reference).

The artificial joint is fabricated using processes of investment casting, milling and compression molding. For example, a solid model comprised of a thermally labile material (e.g., wax) is made by injection molding and then a ceramic shell is created by coating the solid wax model. The ceramic shell is recovered after melting the solid model and used as a mold to cast the components of the prosthesis. See e.g., U.S. Pat. No. 5,665,118, ibid., which is incorporated herein by reference. A series of cavities are cast around the circumference of the femoral component and at the base of the neck of the acetabular component, with associated apertures within non-contact surfaces of the prosthesis. These cavities are configured to contain actuated fluid deflector structures with size, shape, number and position as required by the specific prosthesis design.

Magnetic actuated fluid deflector structures are constructed from polydimethylsiloxane (PDMS, available from Dow Corning Corp., Midland, Mich.) containing permanently magnetic nanoparticles. Carbon coated iron particles approximately 70 nm in diameter (available from M K Impex Corp., Missisauga, ON, Canada) are dispersed in PDMS to form a composite. This composite is then cast in the cavities of the femoral and acetabular components to form fluid deflector structures approximately 1 cm long and 3 mm wide protruding from the cavities (see e.g., van Engen, ibid., which is incorporated herein by reference). Each fluid deflector structure includes a proximal end that is positioned within the associated cavity, the proximal end of a size and shape to be blocked from leaving the cavity by the size and shape of the associated aperture. Each fluid deflector structure includes a region traversing the aperture. Each fluid deflector structure also includes a functional region approximately 1 cm long and 3 mm wide external to the cavity and aperture. The fluid deflector structures are magnetized by repeated movement of a permanent magnet along the long axis of the deflectors with a magnetic field of about 500 mTesla. The fluid deflector structures also include distal edge regions which contain adhesive tips configured to capture and retain debris particles. Artificial actuated cilia which adhere to particles and are used for propelling particles (antifouling) and trapping particles (filtration) are described (see e.g., Bhattacharya et al., "Propulsion and Trapping of Microparticles by Active Cilia Arrays," *Langmuir* 28: 3217-3226, (2012) which is incorporated herein by reference).

A permanent magnet is constructed in the neck of the femoral component to actuate the magnetic fluid deflector structures with a magnetic field that is oriented substantially perpendicular to the deflectors. A permanent magnet with a magnetic field of approximately 500 mTesla is placed in the neck region of the femoral component to actuate the magnetic fluid deflector structures on the femoral and acetabular components as the hip joint moves. For example, a magnetic field of approximately 50 mTesla applied perpendicular to magnetic cilia has been shown to cause a deflection of approximately 0.5 millimeter (see van Engen, ibid., which is incorporated herein by reference). See also US Patent Application No. 2006/0149386, "Joint Prosthesis," to Clarke and Lee, which is incorporated by reference herein.

Magnetic fluid deflector structures with distal edge regions that contain adhesive tips are positioned around the circumference of the femoral stem and the acetabular cup. The position, size, shape, number and orientation of the fluid deflector structures on each prosthesis component is configured to divert synovial joint fluid and associated debris particles away from the bone-prosthesis interfaces. Each of the fluid deflector structures is also configured to trap debris particles from synovial joint fluid with the adhesive tips attached to the distal edge regions of the fluid deflector structures. Models to calculate the optimal adhesive force and stiffness for the fluid deflector structures to trap particles are described (see Bhattacharya et al., ibid., which is incorporated herein by reference). Actuated magnetic fluid deflector structures with distal edge regions that contain adhesive tips are configured to move in response to the motion of a magnet positioned within the femoral component. Physiological movement of the artificial hip joint moves the magnet within the femoral stem into proximity of the fluid deflector structures and causes the fluid deflector structures to bend or flex in response to the magnetic field. Movement of the fluid deflector structures promotes directed fluid flow and trapping of debris particles (see e.g., van Engen, ibid. and Bhattacharya et al., ibid., which are each incorporated herein by reference). Repeated "beating" of the fluid deflector structures during regular activities, e.g., walking, running, sitting, reclining, or sleeping, acts to divert the flow of synovial fluid away from the prosthesis-bone interfaces and traps debris particles within the fluid with the adhesive tips at the distal edge regions of the fluid deflector structures. Thus, the artificial hip joint with actuated adhesive fluid deflector structures reduces the likelihood of osteolysis, periprosthetic bone resorption and prosthesis loosening in vivo.

Example 5

An Artificial Hip Joint Including Fluid Deflector Structures Configured to Respond to a Magnetic Field A hip joint prosthesis is fabricated with actuated fluid deflector structures on select non-contact surfaces of the device. The actuated fluid deflector structures are configured to divert joint fluid and debris particles away from the interface regions between the implanted artificial joint and the patient's bones. Debris particles within the joint fluid are associated with an increased likelihood of osteolysis and aseptic loosening of the prosthetic implant.

The hip joint prosthesis includes a femoral component which includes a head (or ball), a neck, and a stem which is configured to be implanted in the medullary canal of the femur. The hip joint prosthesis also includes an acetabular component that includes an outer and inner cup, with the outer cup configured to be attached to pelvic bone and the inner cup forming a socket that bears the head of the femoral component in vivo. The neck and stem of the femoral component are predominately fabricated from titanium (see e.g., U.S. Pat. No. 6,761,741, ibid., which is incorporated herein by reference).

The artificial joint is fabricated using processes of investment casting, milling and compression molding. For example, a solid model comprised of a thermally labile material (e.g., wax) is made by injection molding and then a ceramic shell is created by coating the solid wax model. The ceramic shell is recovered after melting the solid model and used as a mold to cast the components of the prosthesis. See e.g., U.S. Pat. No. 5,665,118, ibid., which is incorporated herein by reference. A series of cavities are cast around the circumference of the acetabular cup, with associated apertures within non-contact surfaces of the prosthesis. The cavities in the acetabular cup are configured with substantially circular sides, to contain substantially circular mechanisms attached to fluid deflector structures, of size, shape, number and position as required by the specific prosthesis design.

Figure 11:
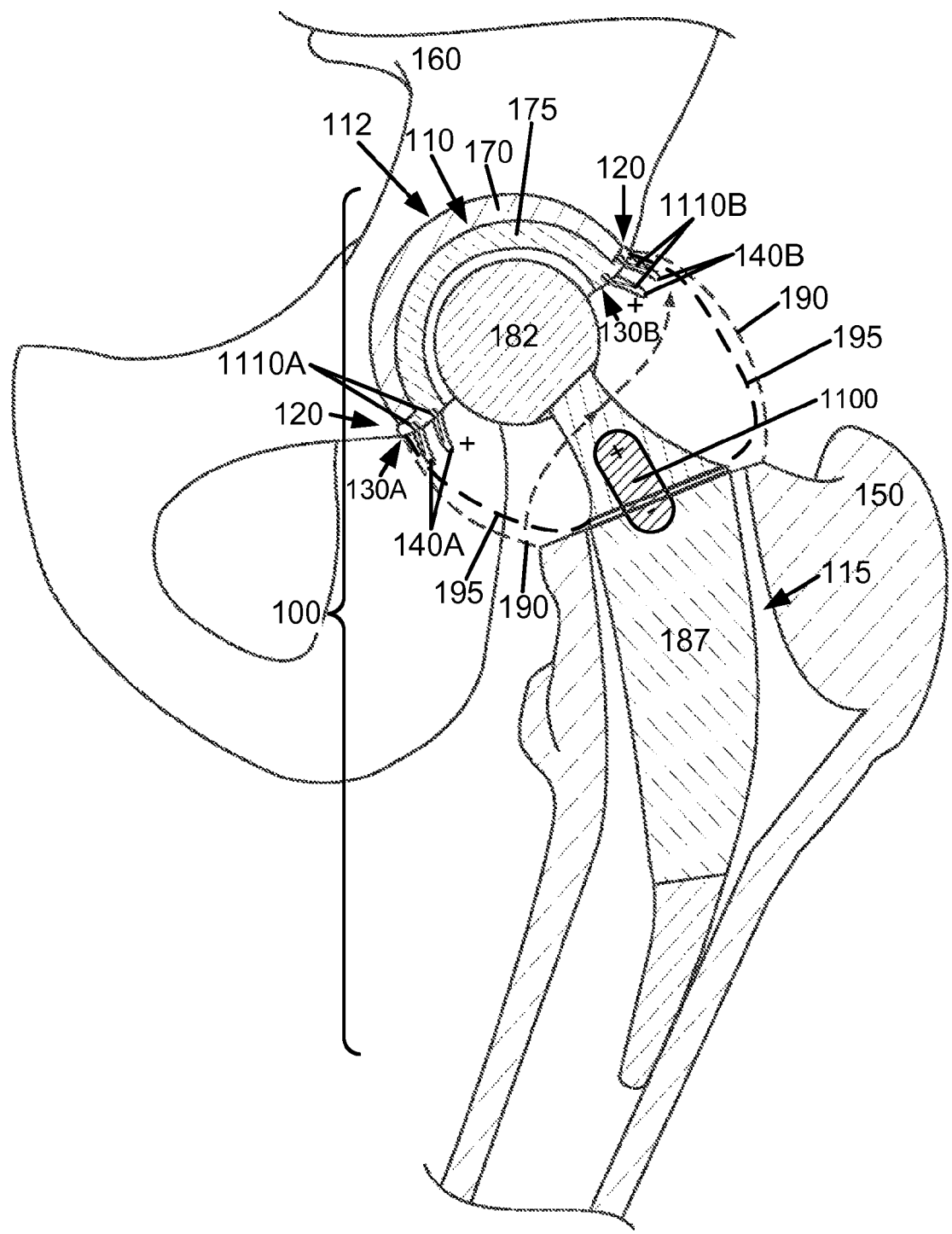
FIG. 11 depicts an artificial hip joint in cross-section.

A permanent magnet is constructed in the neck of the femoral component, with a magnetic field that is oriented substantially along the long axis of the neck of the femoral component. FIG. 11 illustrates the permanent magnet 1100 embedded within the femoral stem component 187, with the axis of polarity of the magnet (represented as + and − in the Figure) oriented substantially along the long axis of the femoral stem component 187. A permanent magnet with a magnetic field of approximately 500 mTesla is placed in the neck region of the femoral component to actuate the magnetic fluid deflector structures on the acetabular cup that approach the permanent magnet 1100 as the hip joint moves. For example, a magnetic field of approximately 50 mTesla applied perpendicular to magnetic cilia has been shown to cause a deflection of approximately 0.5 millimeter (see van Engen, ibid., which is incorporated herein by reference). See also US Patent Application No. 2006/0149386, "Joint Prosthesis," to Clarke and Lee, which is incorporated by reference herein.

As illustrated in FIG. 11, each of the fluid deflecting structures 140A, 140B is attached to a mechanism 1110A, 1110B that includes a ball-like end configured to fit within the cavities in the acetabular cup, and an attached rod projecting away from the non-contact surface of the prosthesis along the long axis of the fluid deflecting structures 140A, 140B. The ball-like end of the mechanism 1110A, 1110B is of a size and shape configured to fit within a corresponding cavity in the femoral stem component 187, and to rotate within the cavity. Each of the rod structures of the mechanism 1110A, 1110B is a permanent magnet, with an axis of polarity along the long axis of the rod. The polarity of the distal end of the rod structure of a mechanism 1110A, 1110B is the same as the polarity of the closer end of the permanent magnet 1100 embedded within the femoral stem component 187. For example, FIG. 11 illustrates a permanent magnet 1100 embedded within the femoral stem component 187 with a "north" polar end ("+") at the end of the permanent magnet 1100 adjacent to the femoral ball 182. Correspondingly, FIG. 11 shows the distal ends of the rod structures of the mechanisms 1110A, 1110B as including a "north" polar end ("+"). Although the instant illustration shows these ends as including a "north" polar end ("+"), embodiments also include those with corresponding "south" polar ends ("−") on the end of the permanent magnet 1100 adjacent to the femoral ball 182 and the distal ends of the rod structures of the mechanisms 1110A, 1110B.

Actuated fluid deflector structures 140A, 140B are formed at the edge region of the acetabular liner. The fluid deflector structures are configured to deflect synovial fluid flow and associated debris particles away from the interfaces between the prosthesis components and bone and to mitigate transient joint fluid pressure on the prosthesis-bone interfaces during physiological use of the joint. Magnetic actuated fluid deflector structures are constructed from polydimethylsiloxane (PDMS, available from Dow Corning Corp., Midland, Mich.) around the core rods of the mechanism 1110A, 1110B. The PDMS is cast around the rod structures of the mechanisms 1110A, 1110B to form fluid deflector structures approximately 10 mm long and 3 mm wide protruding from the cavities (see e.g., van Engen, ibid., which is incorporated herein by reference). Each fluid deflector structure 140A, 140B includes a mechanism 1110A, 1110B including a rod structure with a proximal end that is positioned within the associated cavity, the proximal end of a size and shape to be blocked from leaving the cavity by the size and shape of the associated aperture while allowing for rotation within the cavity. Each fluid deflector structure 140A, 140B includes a region traversing the aperture. Each fluid deflector structure 140A, 140B also includes a functional deflector region approximately 10 mm long and 3 mm wide external to the cavity and aperture.

Magnetic fluid deflector structures 140A, 140B are positioned around the circumference of the acetabular cup 175.

The position, size, shape, number and orientation of the fluid deflector structures 140A, 140B is configured to divert synovial joint fluid and associated debris particles away from the bone-prosthesis interfaces. Actuated magnetic fluid deflector structures 140A, 140B are configured to move in response to the motion of the magnet 1100 positioned within the femoral stem component 187. Physiological movement of the artificial hip joint moves the magnet 1100 within the femoral stem 187 into proximity of the fluid deflector structures 140A on the adjacent edge of the acetabular cup 175. The proximity of the same-polarity magnetic fields causes the fluid deflector structures 140A to bend or flex in response to the magnetic field in a direction away from the femoral stem 187. Movement of the fluid deflector structures 140A promotes directed fluid flow away from the bone-prosthesis interface. Repeated "beating" of the fluid deflector structures 140A, 140 B in response to the relative re-positioning of the fluid deflector structures 140A, 140 B and the magnet 1100 positioned within the femoral stem component 187 during regular activities, e.g., walking, running, sitting, reclining, or sleeping, acts to divert the flow of synovial fluid away from the prosthesis-bone interfaces. Thus, the artificial hip joint with embedded magnet 1100 and actuated fluid deflector structures 140 A, 140 B reduces the likelihood of osteolysis, periprosthetic bone resorption and prosthesis loosening in vivo.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An artificial joint prosthesis, comprising:
    a bone-facing surface of an artificial joint prosthesis, the bone-facing surface configured to face a bone-prosthesis interface in vivo;
    a non-load bearing surface of the artificial joint prosthesis, the non-load bearing surface adjacent to the bone-facing surface of the artificial joint prosthesis;
    an aperture in the non-contact surface of the artificial joint prosthesis;
    a substantially round cavity in the artificial joint prosthesis adjacent to the aperture;
    a mechanism including a substantially round element of a size and shape to correspond to the substantially round cavity, the substantially round element positioned to move within the substantially round cavity;
    at least one fluid deflection structure attached to the substantially round element and projecting through the aperture; and
    at least one particle retaining structure positioned to contact the directed flow of synovial fluid and configured to retain non-physiological particles present within the synovial fluid.

2. An artificial joint prosthesis, comprising:
    a bone-facing surface of an artificial joint prosthesis, the bone-facing surface configured to face a bone-prosthesis interface in vivo;
    a non-contact surface of the artificial joint prosthesis, the non-contact surface adjacent to the bone-facing surface of the artificial joint prosthesis;
    at least one fluid deflection structure positioned adjacent to the non-contact surface, the fluid deflection structure positioned to deflect synovial fluid away from the bone-prosthesis interface in vivo;
    a mechanism attached to the fluid deflection structure, the mechanism including piezoelectric material configured to move the fluid deflection structure to direct synovial fluid away from the bone-prosthesis interface in vivo; and
    at least one particle retaining structure positioned to contact the directed flow of synovial fluid and configured to retain non-physiological particles present within the synovial fluid.

3. The artificial joint prosthesis of claim 2, wherein the at least one fluid deflection structure attached to the non-contact surface comprises:
    at least one flange structure with a first end connected to the non-contact surface and a second end distal to the non-contact surface.

4. The artificial joint prosthesis of claim 2, wherein the at least one fluid deflection structure attached to the non-contact surface comprises:
    a plurality of flange structures.

5. The artificial joint prosthesis of claim 2, wherein the at least one fluid deflection structure attached to the non-contact surface comprises:
    a plurality of linear projections.

6. The artificial joint prosthesis of claim 2, wherein the mechanism attached to the fluid deflection structure is substantially enclosed within the artificial joint prosthesis.

7. The artificial joint prosthesis of claim 2, wherein the mechanism attached to the fluid deflection structure comprises:
    a battery configured to provide energy to the mechanism.

8. The artificial joint prosthesis of claim 2, comprising:
    an aperture in the non-contact surface of the artificial joint prosthesis;
    a substantially round cavity in the artificial joint prosthesis adjacent to the aperture;
    the mechanism including a substantially round element of a size and shape to correspond to the substantially round cavity, the substantially round element positioned within the substantially round cavity and configured to move within the substantially round cavity; and
    the at least one fluid deflection structure attached to the substantially round element and projecting through the aperture.

9. The artificial joint prosthesis of claim 2, comprising:
    at least two components, each of which include at least one fluid deflection structure, and each of which include the mechanism attached to the fluid deflection structure, each of the mechanism operable to move each of the fluid deflection structure to direct synovial fluid away from the bone-prosthesis interface in vivo in the direction of the at least one particle retaining structure.

10. A hip joint prosthesis, comprising:
    a bone-facing surface of a hip joint prosthesis, the bone-facing surface configured to face a bone-prosthesis interface in vivo;
    a non-contact surface of the hip joint prosthesis, the non-contact surface adjacent to the bone-facing surface of the hip joint prosthesis;
    at least one fluid deflection structure positioned adjacent to the non-contact surface, the fluid deflection structure positioned to deflect synovial fluid away from the bone-prosthesis interface in vivo;

a mechanism attached to the fluid deflection structure, the mechanism including piezoelectric material configured to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

11. The hip joint prosthesis of claim 10, wherein the at least one fluid deflection structure adjacent to the non-contact surface comprises:
at least one flange structure with a first end connected to the non-contact surface and a second end distal to the non-contact surface.

12. The hip joint prosthesis of claim 10, wherein the at least one fluid deflection structure adjacent to the non-contact surface comprises:
a plurality of flange structures.

13. The hip joint prosthesis of claim 10, wherein the at least one fluid deflection structure adjacent to the non-contact surface comprises:
a plurality of linear projections.

14. The hip joint prosthesis of claim 10, wherein the mechanism attached to the fluid deflection structure is substantially enclosed within the hip joint prosthesis.

15. The hip joint prosthesis of claim 10, wherein the mechanism attached to the fluid deflection structure comprises:
a battery configured to provide energy to the mechanism.

16. The hip joint prosthesis of claim 10, comprising:
an aperture in the non-contact surface of the hip joint prosthesis;
a substantially round cavity in the hip joint prosthesis adjacent to the aperture;
the mechanism including a substantially round element of a size and shape to correspond to the substantially round cavity, the substantially round element positioned within the substantially round cavity and configured to move within the substantially round cavity; and
the at least one fluid deflection structure attached to the substantially round element and projecting through the aperture.

17. The hip joint prosthesis of claim 10, comprising:
at least one acetabular component, wherein the acetabular component includes at least one fluid deflection structure adjacent to the non-contact surface and at least one mechanism attached to the at least one fluid deflection structure; and
at least one femoral component, wherein the femoral component includes at least one fluid deflection structure adjacent to the non-contact surface and at least one mechanism attached to the at least one fluid deflection structure.

18. A knee joint prosthesis, comprising:
a bone-facing surface of a knee joint prosthesis, the bone-facing surface configured to face a bone-prosthesis interface in vivo;
a non-contact surface of the knee joint prosthesis, the non-contact surface adjacent to the bone-facing surface of the knee joint prosthesis;
at least one fluid deflection structure positioned adjacent to the non-contact surface, the fluid deflection structure positioned to deflect synovial fluid away from the bone-prosthesis interface in vivo;
a mechanism attached to the fluid deflection structure, the mechanism including piezoelectric material configured to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

19. The knee joint prosthesis of claim 18, wherein the at least one fluid deflection structure adjacent to the non-contact surface comprises:
at least one flange structure with a first end adjacent to the non-contact surface and a second end distal to the non-contact surface.

20. The knee joint prosthesis of claim 18, wherein the at least one fluid deflection structure adjacent to the non-contact surface comprises:
a plurality of flange structures.

21. The knee joint prosthesis of claim 18, wherein the at least one fluid deflection structure adjacent to the non-contact surface comprises:
a plurality of linear projections.

22. The knee joint prosthesis of claim 18, wherein the mechanism attached to the fluid deflection structure is substantially enclosed within the artificial joint prosthesis.

23. The knee joint prosthesis of claim 18, wherein the mechanism attached to the fluid deflection structure comprises:
a battery configured to provide energy to the mechanism.

24. The knee joint prosthesis of claim 18, comprising:
an aperture in the non-contact surface of the knee joint prosthesis;
a substantially round cavity in the knee joint prosthesis adjacent to the aperture;
the mechanism including a substantially round element of a size and shape to correspond to the substantially round cavity, the substantially round element positioned within the substantially round cavity and configured to move within the substantially round cavity; and
the at least one fluid deflection structure attached to the substantially round element and projecting through the aperture.

25. The knee joint prosthesis of claim 18, comprising:
at least one femoral component, wherein the femoral component includes at least one fluid deflection structure adjacent to the non-contact surface and at least one mechanism attached to the at least one fluid deflection structure; and
at least one tibial component, wherein the tibial component includes at least one fluid deflection structure adjacent to the non-contact surface and at least one mechanism attached to the at least one fluid deflection structure.

26. A shoulder joint prosthesis, comprising:
a bone-facing surface of a shoulder joint prosthesis, the bone-facing surface configured to face a bone-prosthesis interface in vivo;
a non-contact surface of the shoulder joint prosthesis, the non-contact surface adjacent to the bone-facing surface of the shoulder joint prosthesis;
at least one fluid deflection structure positioned adjacent to the non-contact surface, the fluid deflection structure positioned to deflect synovial fluid away from the bone-prosthesis interface in vivo;
a mechanism attached to the fluid deflection structure, the mechanism including piezoelectric material configured to move the fluid deflection structure to direct synovial fluid away from the bone-prosthesis interface in vivo; and at least one particle retaining structure positioned to contact the directed flow of synovial fluid and configured to retain non-physiological particles present within the synovial fluid.

27. The shoulder joint prosthesis of claim 26, wherein the at least one fluid deflection structure adjacent to the non-contact surface comprises:

at least one flange structure with a first end connected to the non-contact surface and a second end distal to the non-contact surface.

28. The shoulder joint prosthesis of claim 26, wherein the at least one fluid deflection structure adjacent to the non-contact surface comprises:

a plurality of flange structures.

29. The shoulder joint prosthesis of claim 26, wherein the at least one fluid deflection structure adjacent to the non-contact surface comprises:

a plurality of linear projections.

30. The shoulder joint prosthesis of claim 26, wherein the mechanism attached to the fluid deflection structure is substantially enclosed within the shoulder joint prosthesis.

31. The shoulder joint prosthesis of claim 26, wherein the mechanism attached to the fluid deflection structure comprises:

a battery configured to provide energy to the mechanism.

32. The shoulder joint prosthesis of claim 26, comprising:
an aperture in the non-contact surface of the artificial joint prosthesis;
a substantially round cavity in the shoulder joint prosthesis adjacent to the aperture;
the mechanism including a substantially round element of a size and shape to correspond to the substantially round cavity, the substantially round element positioned within the substantially round cavity and configured to move within the substantially round cavity; and
the at least one fluid deflection structure attached to the substantially round element and projecting through the aperture.

33. The shoulder joint prosthesis of claim 26, comprising:
at least one humeral component, wherein the humeral component includes at least one fluid deflection structure adjacent to the non-contact surface and at least one mechanism attached to the at least one fluid deflection structure; and
at least one scapular component, wherein the scapular component includes at least one fluid deflection structure adjacent to the non-contact surface and at least one mechanism attached to the at least one fluid deflection structure.

* * * * *